(12) United States Patent
You et al.

(10) Patent No.: US 9,133,524 B2
(45) Date of Patent: Sep. 15, 2015

(54) PROTEIN KINASE CK2 GENE MUTATIONS, AMPLIFICATIONS AND POLYMORPHISMS IN HUMAN CANCERS AND METHODS OF USE

(75) Inventors: Liang You, San Francisco, CA (US); Zhidong Xu, San Francisco, CA (US); Biao He, Foster City, CA (US); David Jablons, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 105 days.

(21) Appl. No.: 13/806,093

(22) PCT Filed: Jul. 1, 2011

(86) PCT No.: PCT/US2011/042876
§ 371 (c)(1),
(2), (4) Date: May 9, 2013

(87) PCT Pub. No.: WO2012/003493
PCT Pub. Date: Jan. 5, 2012

(65) Prior Publication Data
US 2013/0230852 A1   Sep. 5, 2013

Related U.S. Application Data

(60) Provisional application No. 61/360,876, filed on Jul. 1, 2010.

(51) Int. Cl.
| | | |
|---|---|---|
| *C12Q 1/68* | (2006.01) |
| *C07H 21/02* | (2006.01) |
| *C07H 21/04* | (2006.01) |
| *C12N 9/12* | (2006.01) |
| *G01N 33/68* | (2006.01) |

(52) U.S. Cl.
CPC ............ *C12Q 1/6886* (2013.01); *C12N 9/1205* (2013.01); *C12Y 207/11001* (2013.01); *G01N 33/6893* (2013.01); *C12Q 2600/118* (2013.01); *C12Q 2600/136* (2013.01); *C12Q 2600/156* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 4,676,980 A | 6/1987 | Segal et al. |
| 4,816,567 A | 3/1989 | Cabilly et al. |
| 4,946,778 A | 8/1990 | Ladner et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,837,821 A | 11/1998 | Wu |
| 5,882,864 A | 3/1999 | An et al. |
| 6,019,944 A | 2/2000 | Buechler |
| 2005/0163782 A1 | 7/2005 | Glasser et al. |
| 2007/0196274 A1 | 8/2007 | Sun |

FOREIGN PATENT DOCUMENTS

| | | |
|---|---|---|
| WO | 91/00360 A1 | 1/1991 |
| WO | 91/02805 A2 | 3/1991 |
| WO | 91/02805 A3 | 4/1991 |
| WO | 92/20373 A1 | 11/1992 |
| WO | 93/08829 A1 | 5/1993 |
| WO | 95/21944 A1 | 8/1995 |

OTHER PUBLICATIONS

The Free Dictionary, definition for "determining", printed on Mar. 4, 2014, available via url: <thefreedictionary.com/determining>.*
Garber et al. PNAS. 2001. 98: 13784-13789.*
Bhattacharjee et al. PNAS. 2001. 98:13790-13794.*
Schmidt et al. Blood. 1998. 91: 22-29.*
Ito et al AntiCancer Research. 2002. 22(4):2385-2389.*
Liu et al Clinical Immunology. 2004. 112: 225-230.*
Coleman. R. Drug Discovery Today. 2003. 8: 233-235.*
Hanke et al. Clinical Chemistry. 2007. 53: 2070-2077.*
Palmer et al. BMC Genomics. 2006. 7:115.*
Dermer, G.B. Bio/Technology (1994) 12: 320.*
Altschul et al., "Basic Local Alignment Search Tool", Journal of Molecular Biology, vol. 215, 1990, pp. 403-410.
Altschul et al., Gapped BLAST and PSI-BLAST: A New Generation of Protein Database Search Programs, Nucleic Acids Research, vol. 25, No. 17, 1997, pp. 3389-3402.
De Andres et al., "BioTechniques", The Journal of Laboratory Technology for Bioresearch, vol. 18, No. 1, Jan. 1995, 6 pages.
Bao, James J., "Capillary Electrophoretic Immunoassays", Journal of Chromatography B, vol. 699, 1997, pp. 463-480.
Batzer et al., "Enhanced Evolutionar PCR Using Oligonucleotides with Inosine at the 3'-Terminus", Nucleic Acids Research, vol. 19, No. 18, 1991, p. 5081.
Cole et al., "The EBV-Hybridoma Technique and its Application to Human Lung Cancer", Monoclonal Antibodies and Cancer Therapy, 1985, pp. 77-96.
Dieffenbach et al., "General Concepts for PCR Primer Design", PCR Primer, A Laboratory Manual, 1995, pp. 133-142.
EBI Accession No. Q5R823, "Full=Putative Uuncharacterized Protein DKFZp469K1920", available online at <www. uniprot.org/uniprot/Q5R823.txt>, accessed on Sep. 25, 2014, Dec. 21, 2004, 1 page.
Eisenberg et al., "Human Housekeeping Genes are Compact", Trends in Genetics, vol. 19, No. 7, Jul. 2003, pp. 362-365.
Fink et al., "Measurement of Proteins with the Behring Nephelometer A Multicentre Evaluation", Journal of Clinical Chemistry and Clinical Biochemistry, vol. 27, No. 4, 1989, pp. 261-276.

(Continued)

*Primary Examiner* — Carla Myers
(74) *Attorney, Agent, or Firm* — Morrison & Foerster LLP

(57) ABSTRACT

The present disclosure provides methods and compositions for diagnosis and for providing a prognosis of a cancer patient by assessing CK2 alpha 1 pseudogene (CSNK2A1P) status. The present disclosure also provides polypeptide, polynucleotide, host cell, and transgenic animal compositions associated with CSNK2A1P.

14 Claims, 20 Drawing Sheets

(56) References Cited

OTHER PUBLICATIONS

Fishwild et al., "High-Avidity Human IgGK Monoclonal Antibodies from a Novel Strain of Minilocus Transgenic Mice", Nature Biotechnology, vol. 14, Jul. 1996, pp. 845-851.
Heid et al., "Real Time Quantitative PCR", Genome Research, 1996, pp. 986-994.
Henikoff et al., "Amino Acid Substitution Matrices From Protein Blocks", Proceedings of the National Academy of Sciences, vol. 89, Nov. 1992, pp. 10915-10919.
Innis et al., "Optimization of PCRs", PCR Protocols: A Guide to Methods and Applications, 1990, pp. 3-12.
Jones et al., Replacing the Complementarity-Determining Regions in a Human Antibody with Those from a Mouse, Nature, vol. 321, May 29, 1986, pp. 522-525.
Kohler et al., "Continuous Cultures of Fused Cells Secreting Antibody of Predefined Specificity", Nature, vol. 256, Aug. 7, 1975, pp. 495-497.
Kozbor et al., "The Production of Human Monoclonal Antibodies from Human Lymphocytes", Immunology Today vol. 4, 1983, pp. 72-79.
Li et al., "Effects of Protein Kinase CK2α on the Proliferation and Invasion of Human Nasopharyngeal Carcinoma", Chin J. Pathol, vol. 38, No. 8, Aug. 2009, pp. 529-531 (English Abstract Submitted).
Lonberg et al., "Antigen-Specific Human Antibodies from Mice Comprising four Distinct Genetic Modifications", Nature, vol. 368, Apr. 28, 1994, pp. 856-859.
Lonberg et al., "Human Antibodies from Transgenic Mice", International Reviews of Immunology. vol. 13, 1995, pp. 65-93.
Marks et al., "By-Passing Immunization: Building High Affinity Human Antibodies by Chain Shuffling", Biotechnology, vol. 10, Jul. 1992, pp. 779-783.
McCafferty et al., "Phage Antibodies: Filamentous Phage Displaying Antibody Variable Domains", Nature, vol. 348, Dec. 6, 1990, pp. 552-554.
Meggio et al., "One-Thousand-and-One Substrates of Protein Kinese CK2?", The Faseb Journal, vol. 17, Mar. 2003, pp. 349-368.
Morrison, Sherie L., "Success in Specification", Nature, vol. 368, Apr. 28, 1994, pp. 812-813.
Needleman et al., "A General Method Applicable to the Search for Similarities in the Amino Acid Sequence of Two Proteins", Journal of Molecular Biology, vol. 48, 1970, pp. 443-453.
Neuberger, Michael, "Generating High-avidity Human Mabs in Mice", Nature Biotechnology, vol. 14, Jul. 1996, 1 page.
Ng et al., "Biomedical Applications of Protein Chips", J. Cell. Mol. Med., vol. 6, No. 3, 2002, pp. 329-340.
Ohtsuka et al., "An Alternative Approach to Deoxyoligonucleotides as Hybridization Probes by Insertion of Deoxyinosine at Ambiguous Codon Positions", The Journal of Biological Chemistry, vol. 260, No. 5, 1985, pp. 2605-2608.
Pearson et al., "Improved Tools for Biological Sequence Comparison", Proceedings of the National Academy of Sciences, vol. 85, Apr. 1988, pp. 2444-2448.
Plasterer, Thomas N., "Primerselect", Methods in Molecular Biology, vol. 70, 1997, pp. 291-302.
Presta, Leonard G., "Antibody Engineering", Current Opinion in Structural Biology, vol. 2, 1992, pp. 593-596.
Riechmann et al., "Reshaping Human Antibodies for Therapy", Nature, vol. 332, Mar. 24, 1988, pp. 323-327.
Rongen et al., "Liposomes and Immunoassays", Journal of Immunological Methods, vol. 204, 1997, pp. 105-133.
Rossolini et al., "Use of Deoxyinosine-Containing Primers vs Degenerate Primers for Polymerase Chain Reaction Based on Ambiguous Sequence Information", Molecular and Cellular Probes, vol. 8, 1994, pp. 91-98.
Ruan et al., "Expression of Protein Kinase CK2 Subunits in Non-Small-Cell Lung Cancer Tissues and its Significance", Tumor, vol. 28, No. 12, Dec. 2008, pp. 1090-1094 (English abstract Submitted).
Rupp et al., "Purification and Analysis of RNA from Paraffinembedded Tissues", Laboratory Investigation, vol. 56, No. 1, 1987, p. 67A.
Schmalzing et al., "Capillary Electrophoresis Based Immunoassays: A Critical Review", Electrophoresis, vol. 18, 1997, pp. 2184-2193.
Schreiber et al., "Chemical Genetics Resulting from a Passion for Synthetic Organic Chemistry", Bioorganic & Medicinal Chemistry, vol. 6, 1998, pp. 1127-1152.
Schreiber, Stuart L., "Target-Oriented and Diversity-Oriented Organic Synthesis in Drug Discovery", Science, vol. 287, Mar. 17, 2000, pp. 1964-1969.
Self et al., "Advances in Immunoassay Technology", Current Opinion in Biotechnology, vol. 7, 1996, pp. 60-65.
Smith et al., "Comparison of Biosequences", Advances in Applied Mathematics, vol. 2, 1981, pp. 482-489.
Suresh et al., "Bispecific Monoclonal Antibodies from Hybrid Hybridomas", Methods in Enztmology, vol. 121, 1986, pp. 210-228.
Traunecker et al., "Bispecific Single Chain Molecules (Janusins) Target Cytotoxic Lymphocytes on HIV Infected Cells", The EMBO Journal, vol. 10, No. 12, 1991, pp. 3655-3659.
Uematsu et al., "Wnt Pathway Activation in Mesothelioma: Evidence of Dishevelled Overexpression and Transcriptional Activity of β-Catenin", Cancer Research, vol. 63, Aug. 1, 2003, pp. 4547-4551.
Verhoeyen et al., "Reshaping Human Antibodies: Grafting an Antilysozyme Activity", Science, vol. 239, 1988, pp. 1534-1536.
Kasper et al., "Harrison's Principles of Internal Medicine", 16th Edition, 2005, 39 pages.
Devilat, I. et al. (Jan. 25, 1993). "Structure and Sequence of an Intronless Gene for Human Casein Kinase II-α Subunit," *FEBS Letters*. 316(2):114-118.
Hung, M. S. et al (Jul. 2010). "Functional Polymorphism of the CK2α Intronless Gene Plays Oncogenic Roles in Lung Cancer," *PLoS One* 5(7)(e11418):1-10.
International Search Report mailed Feb. 23, 2012, for PCT Application No. PCT/US2011/042876, filed on Jul. 1, 2011, three pages.
Kim, J.S. et al. (Feb. 1, 2007, e-pub. Feb. 8, 2007). "Protein Kinase CK2α as an Unfavorable Prognostic Marker and Novel Therapeutic Target in Acute Myeloid Leukemia," *Clinical Cancer Research* 13(3):1019-1028.
O-Charoenrat, P. et al. (Sep. 1, 2004, e-published Sep. 8, 2004). "Casein Kinase II Alpha Subunit and C1-Inhibitor are Independent Predictors of Outcome in Patients With Squamous Cell Carcinoma of the Lung," *Clinical Cancer Research* 10(17):5792-5803.
Singh, L.S. et al. (Jul. 16, 2002, e-pub. Jun. 14, 2002). "Sequencing of Full-Length cDNA Encoding the α and β Subunits of Human Casein Kinase II From Human Platelets and Megakaryocytic Cells. Expression of the Casein Kinase IIα Intronless Gene in a Megakaryocytic Cell Line," *Biochemistry* 41(28):8935-8940.
ATCC Accession No. 201178 *Saccharomyces cerevisiae* or *Pichia pastoris*, 2013.
GenBank Accession No. NM 002046, Nov. 14, 2014.
Yap et al. (1991). Nucl. Acids. Res. 19:4294.

* cited by examiner

FIG. 1a

| | A427 | A549 | Hela | Jurkat | WI-38 | CCL-211 | "-"ve |
|---|---|---|---|---|---|---|---|
| RT | - + | - + | - + | - + | - + | - + | - + |

CK2P Expression in Mesothelioma Tumors

Indicator of CSNK2A1P Gene | Wild-Type

Indicator of CSNK2A1P Gene | T→C Transition I133T

1: 398C
2: 398T

Dual Luciferase assay of CK2P SiRNA inhibition in HCT 116 Cells

Dual Luciferase assay of CK2P SiRNA inhibition in A549 Cells

Time (months)

SEQUENCE LISTING

<160> NUMBER OF SEQ ID NOS: 35

<210> SEQ ID NO 1
<211> LENGTH: 1176
<212> TYPE: DNA
<213> ORGANISM: Homo sapien

<400> SEQUENCE: 1

```
atgtcgggac ccgtgccaag cagggccaga gtttacacag atgttaatac acacagacct      60
cgagaatact gggattacga gtcacatgtg gtggaatggg gaaatcaaga tgactaccag     120
ctggttcgaa aattaggccg aggtaaatac agtgaagtat ttgaagccat caacatcaca     180
aataatgaaa aagttgttgt taaaattctc aagccagtaa aaaagaagaa aattaagcgt     240
gaaataaaga ttttggagaa tttgagagga ggtcccaaca tcatcacact ggcagacatt     300
gtaaaagacc ctgtgtcacg aaccccgcc ttggttttg aacacgtaaa caacacagac      360
ttcaagcaat tgtaccagac gttaacagac tatgatattc gattttacat gtatgagatt     420
ctgaaggccc tggattattg tcacagcatg ggaattatgc acagagatgt caagccccat     480
aatgtcatga ttgatcatga gcacagaaag ctacgactaa tagactgggg tttggctgag     540
ttttatcatc ctggccaaga atataatgtc cgagttgctt cccgatactt caaaggtcct     600
gagctacttg tagactatca gatgtacgat tatagtttgg atatgtggag tttgggttgt     660
atgctggcaa gtatgatctt tcggaaggag ccattttcc atggacatga caattatgat      720
cagttggtga ggatagccaa ggttctgggg acagaagatt tatatgacta tattgacaaa     780
```

-continued

```
tacaacattg aattagatcc acgtttcaat gatatcttgg gcagacactc tcgaaagcga      840
tgggaacgct ttgtccacag tgaaaatcag caccttgtca gccctgaggc cttggatttc      900
ctggacaaac tgctgcgata tgaccaccag tcacggctta ctgcaagaga ggcaatggag      960
cacccctatt tctacactgt tgtgaaggac caggctcgaa tgggttcatc tagcatgcca     1020 ggggcagta cgcccgtcag cagcgccaat atgatgtcag ggatttcttc agtgccaacc     1080
ccttcacccc ttggacctct ggcaggctca ccagtgattg ctgctgccaa ccccccttggg     1140 atgcctgttc cagctgccgc tggcgctcag cagtaa                               1176
```

<210> SEQ ID NO 2
<211> LENGTH: 391
<212> TYPE: PRT
<213> ORGANISM: Homo sapien

<400> SEQUENCE: 2

```
Met Ser Gly Pro Val Pro Ser Arg Ala Arg Val Tyr Thr Asp Val Asn
 1               5                  10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
           100                 105                 110

Phe Glu His Val Asn Asn Thr Asp Phe Lys Gln Leu Tyr Gln Thr Leu
       115                 120                 125

Thr Asp Tyr Asp Ile Arg Phe Tyr Met Tyr Glu Ile Leu Lys Ala Leu
   130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
               165                 170                 175

Gly Leu Ala Glu Phe Tyr His Pro Gly Gln Glu Tyr Asn Val Arg Val
           180                 185                 190

Ala Ser Arg Tyr Phe Lys Gly Pro Glu Leu Leu Val Asp Tyr Gln Met
       195                 200                 205

Tyr Asp Tyr Ser Leu Asp Met Trp Ser Leu Gly Cys Met Leu Ala Ser
   210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
               245                 250                 255

Tyr Ile Asp Lys Tyr Asn Ile Glu Leu Asp Pro Arg Phe Asn Asp Ile
           260                 265                 270

Leu Gly Arg His Ser Arg Lys Arg Trp Glu Arg Phe Val His Ser Glu
       275                 280                 285

Asn Gln His Leu Val Ser Pro Glu Ala Leu Asp Phe Leu Asp Lys Leu
   290                 295                 300
```

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
            325                 330                 335

Ser Ser Met Pro Gly Gly Ser Thr Pro Val Ser Ser Ala Asn Met Met
        340                 345                 350

Ser Gly Ile Ser Ser Val Pro Thr Pro Ser Pro Leu Gly Pro Leu Ala
            355                 360                 365

Gly Ser Pro Val Ile Ala Ala Ala Asn Pro Leu Gly Met Pro Val Pro
        370                 375                 380

Ala Ala Ala Gly Ala Gln Gln
385                 390

<210> SEQ ID NO 3
<211> LENGTH: 1176
<212> TYPE: DNA
<213> ORGANISM: Homo sapien

<400> SEQUENCE: 3
atgtcgggac cgtgccaag cagggccaga gtttacacag atgttaatac acacagacct      60
cgagaatact gggattacga gtcacatgtg gtggaatggg gaaatcaaga tgactaccag    120
ctggttcgaa attaggccg aggtaaatac agtgaagtat ttgaagccat caacatcaca    180
aataatgaaa aagttgttgt taaaattctc aagccagtaa aaagaagaa aattaagcgt    240 gaaataaaga ttttggagaa tttgagagga ggtcccaaca tcatcacact ggcagacatt    300
gtaaaagacc ctgtgtcacg aaccccgcc ttggttttg aacacgtaaa caacacagac    360
ttcaagcaat tgtaccagac gttcacagac tatgatattc gattttacat gtatgagatt    420
ctgaaggccc tggattattg tcacagcatg ggaattatgc acagagatgt caagccccat    480
aatgtcatga ttgatcatga gcacagaaag ctacgactaa tagactgggg tttggctgag    540 tttatcatc ctggccaaga atataatgtc cgagttgctt cccgatactt caaaggtcct    600
gagctacttg tagactatca gatgtacgat tatagtttgg atatgtggag tttgggttgt    660
atgctggcaa gtatgatctt tcggaaggag ccattttttcc atggacatga caattatgat    720
cagttggtga ggatagccaa ggttctgggg acagaagatt tatatggcta tattgacaaa    780
tacaacattg aattagatcc acgtttcaat gatatcttgg gcagacactc tcgaaagcga    840
tgggaacgct ttgtccaccg tgaaaatcag caccttgtca gccctgaggc cttggatttc    900
ctggacaaac tgctgcgata tgaccaccag tcacggctta ctgcaagaga ggccatggag    960 caccctatt tctacactgt tgtgaaggac caggctcgaa tgggttcatc tagcatgcca   1020 ggggggcagta cacccgtcag cagcgccaat gtgatgtcag ggatttcttc agtgccaacc   1080
ccttcacccc ttggacctct ggcaggctca ccagtgattg ctgctgccaa ccccttggg    1140 atgcctgttc cagctgccgc tggcgctcag cagtaa                            1176

<210> SEQ ID NO 4
<211> LENGTH: 391
<212> TYPE: PRT
<213> ORGANISM: Homo sapien

<400> SEQUENCE: 4

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu

```
                    20                  25                  30
    Trp Gly Asn Gln Asp Asp Tyr Gln Leu Val Arg Lys Leu Gly Arg Gly
                35                  40                  45

Lys Tyr Ser Glu Val Phe Glu Ala Ile Asn Ile Thr Asn Asn Glu Lys
     50                  55                  60

Val Val Val Lys Ile Leu Lys Pro Val Lys Lys Lys Ile Lys Arg
     65                  70                  75                  80

Glu Ile Lys Ile Leu Glu Asn Leu Arg Gly Gly Pro Asn Ile Ile Thr
                    85                  90                  95

Leu Ala Asp Ile Val Lys Asp Pro Val Ser Arg Thr Pro Ala Leu Val
                    100                 105                 110

Phe Glu His Val Asn Asn Thr Asp Phe Lys Gln Leu Tyr Gln Thr Phe
                115                 120                 125

Thr Asp Tyr Asp Ile Arg Phe Tyr Met Tyr Glu Ile Leu Lys Ala Leu
                130                 135                 140

Asp Tyr Cys His Ser Met Gly Ile Met His Arg Asp Val Lys Pro His
    145                 150                 155                 160

Asn Val Met Ile Asp His Glu His Arg Lys Leu Arg Leu Ile Asp Trp
                    165                 170                 175

Gly Leu Ala Glu Phe Tyr His Pro Gly Gln Glu Tyr Asn Val Arg Val
                    180                 185                 190

Ala Ser Arg Tyr Phe Lys Gly Pro Glu Leu Leu Val Asp Tyr Gln Met
                    195                 200                 205

Tyr Asp Tyr Ser Leu Asp Met Trp Ser Leu Gly Cys Met Leu Ala Ser
                    210                 215                 220

Met Ile Phe Arg Lys Glu Pro Phe Phe His Gly Arg Asp Asn Tyr Asp
    225                 230                 235                 240

Gln Leu Val Arg Ile Ala Lys Val Leu Gly Thr Glu Asp Leu Tyr Gly
                    245                 250                 255

Tyr Ile Asp Lys Tyr Asn Ile Glu Leu Asp Pro Arg Phe Asn Asp Ile
                    260                 265                 270

Leu Gly Arg His Ser Arg Lys Arg Trp Glu Arg Phe Val His Arg Glu
                    275                 280                 285

Asn Gln His Leu Val Ser Pro Glu Ala Leu Asp Phe Leu Asp Lys Leu
                    290                 295                 300

Leu Arg Tyr Asp His Gln Ser Arg Leu Thr Ala Arg Glu Ala Met Glu
    305                 310                 315                 320

His Pro Tyr Phe Tyr Thr Val Val Lys Asp Gln Ala Arg Met Gly Ser
                    325                 330                 335

Ser Ser Met Pro Gly Gly Ser Thr Pro Val Ser Ser Ala Asn Val Met
                    340                 345                 350

Ser Gly Ile Ser Ser Val Pro Thr Pro Ser Pro Leu Gly Pro Leu Ala
                    355                 360                 365

Gly Ser Pro Val Ile Ala Ala Asn Pro Leu Gly Met Pro Val Pro
                    370                 375                 380

Ala Ala Ala Gly Ala Gln Gln
    385                 390

<210> SEQ ID NO 5
<211> LENGTH: 1176
<212> TYPE: DNA
<213> ORGANISM: Homo sapien

<400> SEQUENCE: 5
```

-continued

```
atgtcgggac ccgtgccaag cagggccaga gtttacacag atgttaatac acacagacct      60
cgagaatact gggattacga gtcacatgtg gtggaatggg gaaatcaaga tgactaccag     120
ctggttcgaa aattaggccg aggtaaatac agtgaagtat ttgaagccat caacatcaca     180
aataatgaaa aagttgttgt taaaattctc aagccagtaa aaagaagaa  attaagcgt      240
gaaataaaga ttttggagaa tttgagagga ggtcccaaca tcatcacact ggcagacatt     300
gtaaaagacc ctgtgtcacg aaccccccgcc ttggttttg aacacgtaaa caacacagac     360
ttcaagcaat tgtaccagac gttcacagac tatgatactc gattttacat gtatgagatt     420
ctgaaggccc tggattattg tcacagcatg gaattatgc acagagatgt caagccccat      480
aatgtcatga ttgatcatga gcacagaaag ctacgactaa tagactgggg tttggctgag     540
ttttatcatc ctggccaaga atataatgtc cgagttgctt cccgatactt caaaggtcct     600
gagctacttg tagactatca gatgtacgat tatagtttgg atatgtggag tttgggttgt     660
atgctggcaa gtatgatctt tcggaaggag ccatttttcc atggacatga caattatgat     720
cagttggtga ggatagccaa ggttctgggg acagaagatt tatatggcta tattgacaaa     780
tacaacattg aattagatcc acgtttcaat gatatcttgg gcagacactc tcgaaagcga     840
tgggaacgct ttgtccaccg tgaaaatcag caccttgtca gccctgaggc cttggatttc     900
ctggacaaac tgctgcgata tgaccaccag tcacggctta ctgcaagaga ggccatggag     960
caccccatt tctacactgt tgtgaaggac caggctcgaa tgggttcatc tagcatgcca    1020
gggggcagta cacccgtcag cagcgccaat gtgatgtcag ggatttcttc agtgccaacc    1080
ccttcacccc ttggacctct ggcaggctca ccagtgattg ctgctgccaa ccccttggg    1140
atgcctgttc agctgccgc tggcgctcag cagtaa                              1176
```

<210> SEQ ID NO 6
<211> LENGTH: 391
<212> TYPE: PRT
<213> ORGANISM: Homo sapien

<400> SEQUENCE: 6

```
Met Ser Gly Pro Val Pro Ser Arg Ala Arg Val Tyr Thr Asp Val Asn
  1               5                  10                  15

Thr His Arg Pro Arg Glu Tyr Trp Asp Tyr Glu Ser His Val Val Glu
                 20                  25                  30

Trp Gly Asn Gln Asp Asp Tyr Gln Leu Val Arg Lys Leu Gly Arg Gly
             35                  40                  45

Lys Tyr Ser Glu Val Phe Glu Ala Ile Asn Ile Thr Asn Asn Glu Lys
         50                  55                  60

Val Val Val Lys Ile Leu Lys Pro Val Lys Lys Lys Ile Lys Arg
 65                  70                  75                  80

Glu Ile Lys Ile Leu Glu Asn Leu Arg Gly Gly Pro Asn Ile Ile Thr
                 85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Phe
        115                 120                 125

Thr Asp Tyr Asp Thr Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
```

```
                    165                 170                 175
Gly Leu Ala Glu Phe Tyr His Pro Gly Gln Glu Tyr Asn Val Arg Val
                180                 185                 190

Ala Ser Arg Tyr Phe Lys Gly Pro Glu Leu Leu Val Asp Tyr Gln Met
            195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly Arg Asp Asn Tyr Asp
225                 230                 235                 240

Gln Leu Val Arg Ile Ala Lys Val Leu Gly Thr Glu Asp Leu Tyr Gly
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Arg Glu
        275                 280                 285

Asn Gln His Leu Val Ser Pro Glu Ala Leu Asp Phe Leu Asp Lys Leu
    290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Val Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Ala Asn Pro Leu Gly Met Pro Val Pro
    370                 375                 380

Ala Ala Ala Gly Ala Gln Gln
385                 390

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
agaaaattgc tccccactcc                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gtgctgccag agaatgacaa                                                   20

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
gaaaattgct ccccactcca t                                                 21
```

```
<210> SEQ ID NO 10
<211> LENGTH: 18
<212> TYPE: DNA
<213> ORGANISM: Artificial Sequence
<220> FEATURE:
<223> OTHER INFORMATION: Synthetic Construct

<400> SEQUENCE: 10
gtggccgctc tcccttct                                                       18

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct

<400> SEQUENCE: 11
ccgccgtctc tcccttct                                                       18

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
aaaccuuccc aucucuaauc ugaga                                               25

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
agaaaattgc tccccactcc                                                     20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
gtgctgccag agaatgacaa                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
agaaaattgc tccccactcc                                                     20

<210> SEQ ID NO 16
<211> LENGTH: 20
<212> TYPE: DNA
<213> ORGANISM: Artificial Sequence
<220> FEATURE:
```

<223> OTHER INFORMATION: Synthetic Construct

<400> SEQUENCE: 16
gtgctgccag agaatgacaa                                           20

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
tggggacaga agatttatat ga                                        22

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
ctgaagaaat ccctgacatc at                                        22

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
caggtccctc actaccgaca                                           20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
cagctggtag gccatcggat                                           20

<210> SEQ ID NO 21
<211> LENGTH: 36
<212> TYPE: DNA
<213> ORGANISM: Artificial Sequence
<220> FEATURE:
<223> OTHER INFORMATION: Synthetic Construct

<400> SEQUENCE: 21
ccttaaaagc ttgaccatgt cgggacccgt gccaag                         36

<210> SEQ ID NO 22
<211> LENGTH: 34
<212> TYPE: DNA
<213> ORGANISM: Artificial Sequence
<220> FEATURE:
<223> OTHER INFORMATION: Synthetic Construct

<400> SEQUENCE: 22
ccttaaggat ccgactgctg agcgccagcg gcag                           34

```
<210> SEQ ID NO 23
<211> LENGTH: 38
<212> TYPE: DNA
<213> ORGANISM: Artificial Sequence
<220> FEATURE:
<223> OTHER INFORMATION: Synthetic Construct

<400> SEQUENCE: 23
ggctagttta cgtagaccat gtcgggaccc gtgccaag                              38

<210> SEQ ID NO 24
<211> LENGTH: 37
<212> TYPE: DNA
<213> ORGANISM: Artificial Sequence
<220> FEATURE:
<223> OTHER INFORMATION: Synthetic Construct

<400> SEQUENCE: 24
aaggcacagt cgacgctgat cagcgggttt aaactca                               37

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
ccgccttggt ttttgaacac                                                  20

<210> SEQ ID NO 26
<211> LENGTH: 26
<212> TYPE: DNA
<213> ORGANISM: Artificial Sequence
<220> FEATURE:
<223> OTHER INFORMATION: Synthetic Construct

<400> SEQUENCE: 26
ggccttcaga atctcataca tgtaaa                                           26

<210> SEQ ID NO 27
<211> LENGTH: 15
<212> TYPE: DNA
<213> ORGANISM: Artificial Sequence
<220> FEATURE:
<223> OTHER INFORMATION: Synthetic Construct

<400> SEQUENCE: 27
cacagactat gactc                                                       15

<210> SEQ ID NO 28
<211> LENGTH: 16
<212> TYPE: DNA
<213> ORGANISM: Artificial Sequence
<220> FEATURE:
<223> OTHER INFORMATION: Synthetic Construct

<400> SEQUENCE: 28
tcacagacta tgattc                                                      16

<210> SEQ ID NO 29
<211> LENGTH: 40
<212> TYPE: DNA
<213> ORGANISM: Artificial Sequence
<220> FEATURE:
<223> OTHER INFORMATION: Synthetic Construct
```

<400> SEQUENCE: 29
taccagacgt tcacagacta tgatattcga ttttacatgt           40

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct

<400> SEQUENCE: 30
taccagacgt tcacagacta tgatactcga ttttacatgt           40

<210> SEQ ID NO 31
<211> LENGTH: 67
<212> TYPE: DNA
<213> ORGANISM: Artificial Sequence
<220> FEATURE:
<223> OTHER INFORMATION: Synthetic Construct

<400> SEQUENCE: 31
tgtaccagac gttcacagac tatgatattc gattttacat gtatgagatt ctgaacgccc    60
tggatta                                                              67

<210> SEQ ID NO 32
<211> LENGTH: 67
<212> TYPE: DNA
<213> ORGANISM: Artificial Sequence
<220> FEATURE:
<223> OTHER INFORMATION: Synthetic Construct

<400> SEQUENCE: 32
tgtaccagac gttcacagac tatgatattc gattttacat gtatgagatt ctgaaggccc    60
tggatta                                                              67

<210> SEQ ID NO 33
<211> LENGTH: 66
<212> TYPE: DNA
<213> ORGANISM: Artificial Sequence
<220> FEATURE:
<223> OTHER INFORMATION: Synthetic Construct

<400> SEQUENCE: 33
gtaccagacg ttcacagact atgatattcg attttacatg tatgagattc tgaaggccct    60
ggatta                                                               66

<210> SEQ ID NO 34
<211> LENGTH: 68
<212> TYPE: DNA
<213> ORGANISM: Artificial Sequence
<220> FEATURE:
<223> OTHER INFORMATION: Synthetic Construct

<400> SEQUENCE: 34
ttgtaccaga cgttcacaga ctatgatatt cgattttaca tgtatgagat tctgaaggcc    60
ctggatta                                                             68

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Arg Arg Arg Asp Asp Asp Ser Asp Asp Asp
1               5                   10

PROTEIN KINASE CK2 GENE MUTATIONS, AMPLIFICATIONS AND POLYMORPHISMS IN HUMAN CANCERS AND METHODS OF USE

CROSS-REFERENCES TO RELATED APPLICATIONS

This application is a National Phase application under 35 U.S.C. §371 of International Application No. PCT/US2011/0042876, filed Jul. 1, 2011, which claims priority to U.S. provisional application No. 61/360,876, filed Jul. 1, 2010.

STATEMENT AS TO RIGHTS TO INVENTIONS MADE UNDER FEDERALLY SPONSORED RESEARCH AND DEVELOPMENT

Not applicable

BACKGROUND OF THE INVENTION

Cancer is a disease marked by the uncontrolled growth of abnormal cells. Cancer cells have overcome the barriers imposed on normal cells, which have a finite lifespan, to grow indefinitely. As cancerous cell growth continues, genetic alterations may mount until a cancerous cell has achieved a more aggressive growth phenotype. If left untreated, metastasis, which is the spread of cancer cells to distant areas of the body by way of the lymph system or bloodstream, may ensue. Metastasis can result in the destruction of healthy organs and tissues when cancerous cells infiltrate different areas of the body and continue growing to form new tumors.

According to a recent American Cancer Society study, approximately 1,437,180 new cancer cases are expected to be diagnosed in the United States in the year 2008 alone. Despite the availability of numerous chemotherapeutic agents and diagnostic tools, additional diagnostic methods are needed to investigate the mechanisms and pathways that lead to cancerous cell growth. Such methods may lead to the discovery of new drugs that can be used effectively against various types of cancers.

BRIEF SUMMARY OF THE INVENTION

The present disclosure provides methods and compositions for assessing prognosis of a cancer patient by assessing a CK2 alpha 1 pseudogene (CSNK2A1P) status.

The present disclosure arises from the discovery that expression of the CK2Alpha 1 pseudogene (CSNK2A1P) is indicative of the prognosis of a cancer patient. As shown herein, CSNK2A1P expression is inversely correlated with the likelihood of survival, as well as the average survival time, of a cancer patient. In particular, a cancer patient having colon cancer, cervical cancer, lymphatic cancer, skin cancer, or lung cancer, which includes but is not limited to, non-small cell lung cancer (NSCLC). Accordingly, the lower the CSNK2A1P expression level in a biological sample from a patient with cancer or who is likely to develop a cancer, the greater the likelihood of long-term survival. CSNK2A1P expression level can be assessed by assaying CSNK2A1P RNA transcripts or expression products thereof, as well as by assaying the copy number of the CSNK2A1P gene in a cell. In addition, the invention disclosure also arises from the discovery of a CSNK2A1P polymorphism ("I133T") which is associated with elevated expression and/or biological activity of CSNK2A1P. Accordingly, this polymorphism serves as a diagnostic and prognostic marker for cancer and cancer survival.

In some embodiments, assessing CSNK2A1P expression can include assessing expression or DNA (gene) copy number of wild-type CSNK2A1P, the I133T CSNK2A1P polymorphism, a CSNK2A1P variant or mutant, or two or more of the above.

The present disclosure provides methods, kits, and compositions for diagnosing and providing a prognosis for subjects having or suspected of having cancer and for subjects that are at risk of developing cancer. In certain embodiments, these methods comprise assaying "CSNK2A1P status," where CSNK2A1P status can include one or more of expression levels of a CSNK2A1P RNA transcript of expression product thereof, copy number of CSNK2A1P-encoding genes in a cell, and detection of the presence or absence of a CSNK2A1P I133T polymorphism. The present disclosure also features methods and compositions relating to screening for agents that modulate CSNK2A1P expression or activity, and can be designed to particularly assess CSNK2A1P I133T expression or activity.

In one aspect, CSNK2A1P polypeptides are provided herein. In certain embodiments, the CSNK2A1P polypeptides provided herein have amino acid homology to an amino acid sequence of SEQ ID NO:4 or SEQ ID NO:6. In other embodiments, the CSNK2A1P polypeptides comprise polymorphisms and/or amino acid mutations. CSNK2A1P fusion proteins are also provided herein.

In another aspect, polynucleotides that encode CSNK2A1P proteins are provided. In certain embodiments the polynucleotides provided herein encode for a CSNK2A1P protein comprising an amino acid sequence of SEQ ID NO:4 or SEQ ID NO:6. In other embodiments, the polynucleotides encode for CSNK2A1P proteins further comprising a polymorphism and/or amino acid mutation. In some embodiments, the polynucleotides provided herein comprise expression vectors.

In another aspect, host cells harboring a polynucleotide of the disclosure are provided. In certain embodiments, the host cells provided herein express a CSNK2A1P protein comprising an amino acid sequence of SEQ ID NO:4, SEQ ID NO:6, or a mutant thereof. In some embodiments, the host cells provided find use in the screening of compounds for the treatment of CSNK2A1P-associated cancers.

In another aspect, transgenic animals that express a heterologous CSNK2A1P protein are provided. In certain embodiments, the provided transgenic animals express a CSNK2A1P protein comprising an amino acid sequence of SEQ ID NO:4, SEQ ID NO:6, or a mutant thereof. In some embodiments, the transgenic animals provided are useful as a model of CSNK2A1P-associated cancer. In other embodiments, the transgenic animals provided find use in methods of assessing the efficacy of a cancer treatment.

In another aspect, antibodies are provided which specifically bind to a polynucleotide or polypeptide provided herein. In certain embodiments, the antibodies provided herein bind specifically to a CSNK2A1P protein comprising an amino acid sequence of SEQ ID NO:4, SEQ ID NO:6, or a mutant thereof. In some embodiments, the antibodies provided bind specifically to a CSNK2A1P polypeptide, but not to a CK2 polypeptide. In other embodiments, the antibodies provided bind to a specific CSNK2A1P polypeptide, for example a CSNK2A1P polypeptide having an amino acid sequence of SEQ ID NO:4, but not to a second CSNK2A1P polypeptide, for example a CSNK2A1P polypeptide having an amino acid sequence of SEQ ID NO:6.

In another aspect, methods of diagnosing and providing a prognosis for cancer in a subject are provided. In certain embodiments, the methods comprise determining the expression level of CSNK2A1P in a biological sample from the subject, thereby diagnosing or providing a prognosis for cancer in the subject. In some embodiments of the methods provided herein, an increased level of CSNK2A1P is indicative of cancer, an increased risk of developing cancer, an increased risk of cancer recurrence, a reduced likelihood of long term survival, or a reduced likelihood of long term disease free survival in the subject.

In other embodiments, the methods provided herein comprise determining the CSNK2A1P gene copy number in a biological sample from the subject, thereby diagnosing or providing a prognosis for cancer in the subject. In some embodiments of the methods provided herein, an increased copy number of the CSNK2A1P gene is indicative of cancer, an increased risk of developing cancer, an increased risk of cancer recurrence, a reduced likelihood of long term survival, or a reduced likelihood of long term disease free survival in the subject.

In yet other embodiments, the methods provided herein comprise detecting a mutant or polymorphic CSNK2A1P gene in a biological sample from the subject, thereby diagnosing or providing a prognosis for cancer in the subject. In some embodiments of the methods provided herein, a mutant or polymorphic CSNK2A1P gene is indicative of cancer, an increased risk of developing cancer, an increased risk of cancer recurrence, a reduced likelihood of long term survival, or a reduced likelihood of long term disease free survival in the subject.

In another embodiment, methods of assessing the efficacy of a therapeutic treatment for a CSNK2A1P-associated cancer are provided. In certain embodiments, the methods comprise expressing a heterologous CSNK2A1P protein in a mammal, administering a therapeutic treatment to the mammal, and determining an effect of the treatment on the mammal, thereby assessing the efficacy of the therapeutic treatment.

In another embodiment, methods of assessing effects of compounds on cells expressing a CSNK2A1P protein are provided. In certain embodiments, the methods comprise expressing a heterologous CSNK2A1P protein in a cell, administering a compound to the cell, and determining an effect of the compound, thereby assessing the effect of the compound on a cell expressing a CSNK2A1P protein.

BRIEF DESCRIPTION OF THE DRAWINGS

The invention is best understood from the following detailed description when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 1. FIG. 1a shows mRNA expression of the CSNK2A1P gene in cancer cell lines, measured by semi-quantitative RT-PCR.

FIG. 2.

FIG. 3.

FIG. 4.

FIG. 5.

FIG. 6.

FIG. 7. In FIG. 7b, NSCLC patients having high CSNK2A1P mRNA levels at various stages were compared with NSCLC patients having low CSNK2A1P mRNA levels at various stages for their disease free survival for a period of 100 months. In FIG. 7c, NSCLC patients having high CSNK2A1P mRNA levels at Stages I and II were compared with NSCLC patients having low CSNK2A1P mRNA levels at Stages I and II for their overall survival for a period of 120 months. In FIG. 7d, NSCLC patients having high CSNK2A1P mRNA levels at Stages I and II were compared with NSCLC patients having low CSNK2A1P mRNA levels at Stages I and II for their disease free survival for a period of 100 months.

Figure 9:
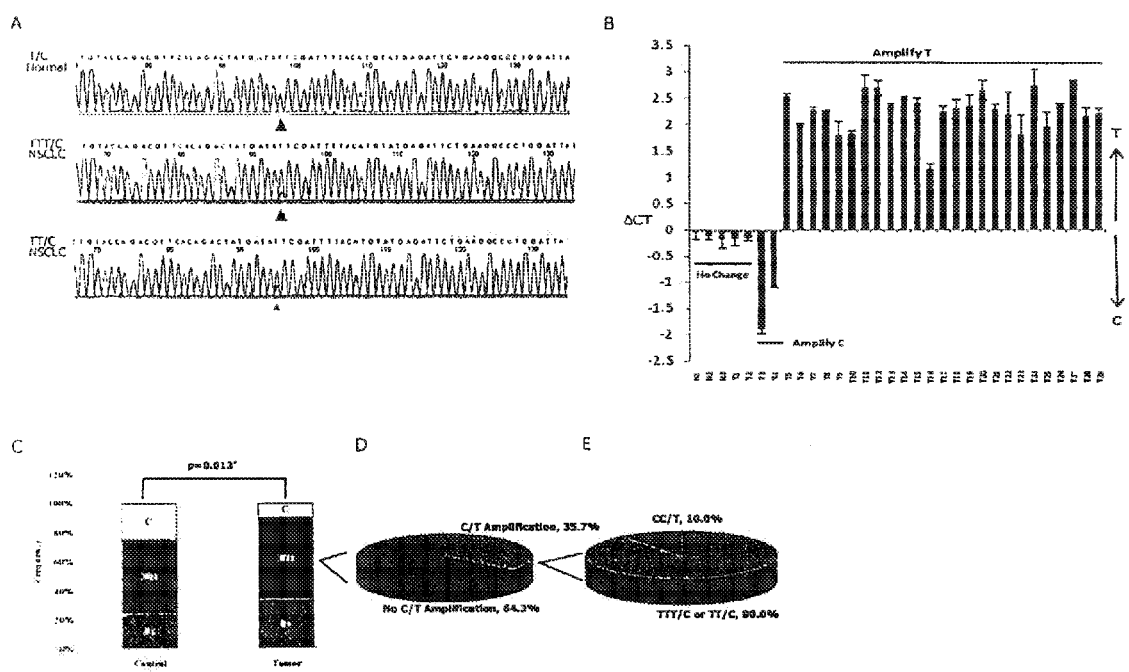

FIG. 9. FIG. 9 shows allele-specific amplification of CSNK2A1P gene in lung cancer. (A) Allele-specific amplification of the 398T allele (TTT/C or TT/C) is found in some non-small cell lung cancer tissue samples. The T above the arrowhead (nucleotide 398T, I133,) indicates the identity of the wild-type gene (nucleotides 370-437 of SEQ ID NO: 3 and SEQ ID NO: 5 shows in figure).

Figure 10:
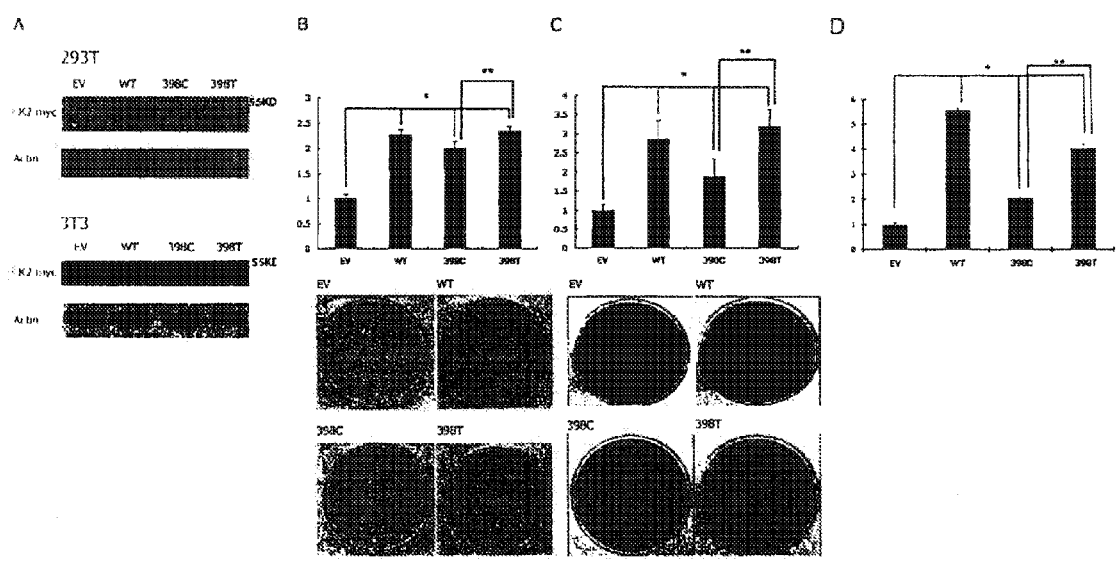

FIG. 10. FIG. 10 shows differential transforming activity of the two CSNK2A1P alleles. (A) The CSNK2A1 and CSNK2A1P genes were transiently transfected into 293T and NIH3T3 cells using Lipofectamine 2000 Reagent according to manufacture's protocol. 72 hours after transfection, cells were harvest and total cellular proteins were extracted. Western blot analysis was used to confirm the protein expression in both alleles of the CSNK2A1P gene. Anti-Myc tag antibody was used to detect the CSNK2A1P-Myc tag fusion proteins. (B) Colony formation assay. Transfection of CSNK2A1P gene in NIH3T3 cells results in enhanced anchorage-dependent growth, compared to the empty vector control. The colony numbers of NIH3T3-CSNK2A1 and NIH3T3-CSNK2A1P cells are dramatically higher than those of the NIH3T3-EV cells. (C) Soft agar assay. Stable transfection of CSNK2A1P genes in NIH3T3 cells results in enhanced anchorage-independent growth. Both the NIH3T3-CSNK2A1 and NIH3T3-CSNK2A1P cells produced significantly more colonies than the NIH3T3-EV cells did (*p<0.05, t-test). Of the two alleles of the CSNK2A1P gene, the 398T allele formed more colonies than the 398C allele did (**p<0.05, t-test). Relative colony formation in both cell lines is expressed as percentage normalized to empty-vector-transfected control group and shown as bar±standard deviation in three independent experiments. (D) Kinase assay of the expressed CSNK2A1 and CSNK2A1P proteins in NIH3T3 cells. The expressed proteins were immune-precipitated with Anti-Myc tag antibody and kinase assay was performed. Both the NIH3T3-CSNK2A1 and NIH3T3-CSNK2A1P cells had significantly higher kinase activities than the NIH3T3-EV cells did (*p<0.05, t-test). Of the two alleles of the CSNK2A1P gene, the 398T allele cells had significantly higher kinase activity than the 398C allele did (**p<0.05, t-test). Relative kinase activity is expressed as percentage normalized to empty-vector-transfected control group and shown as bar±standard deviation in three independent experiments. EV: empty vector. Wt: CSNK2A1. 398C: CSNK2A1P (I133) 398T: CSNK2A1P (I133T).

Figure 11:
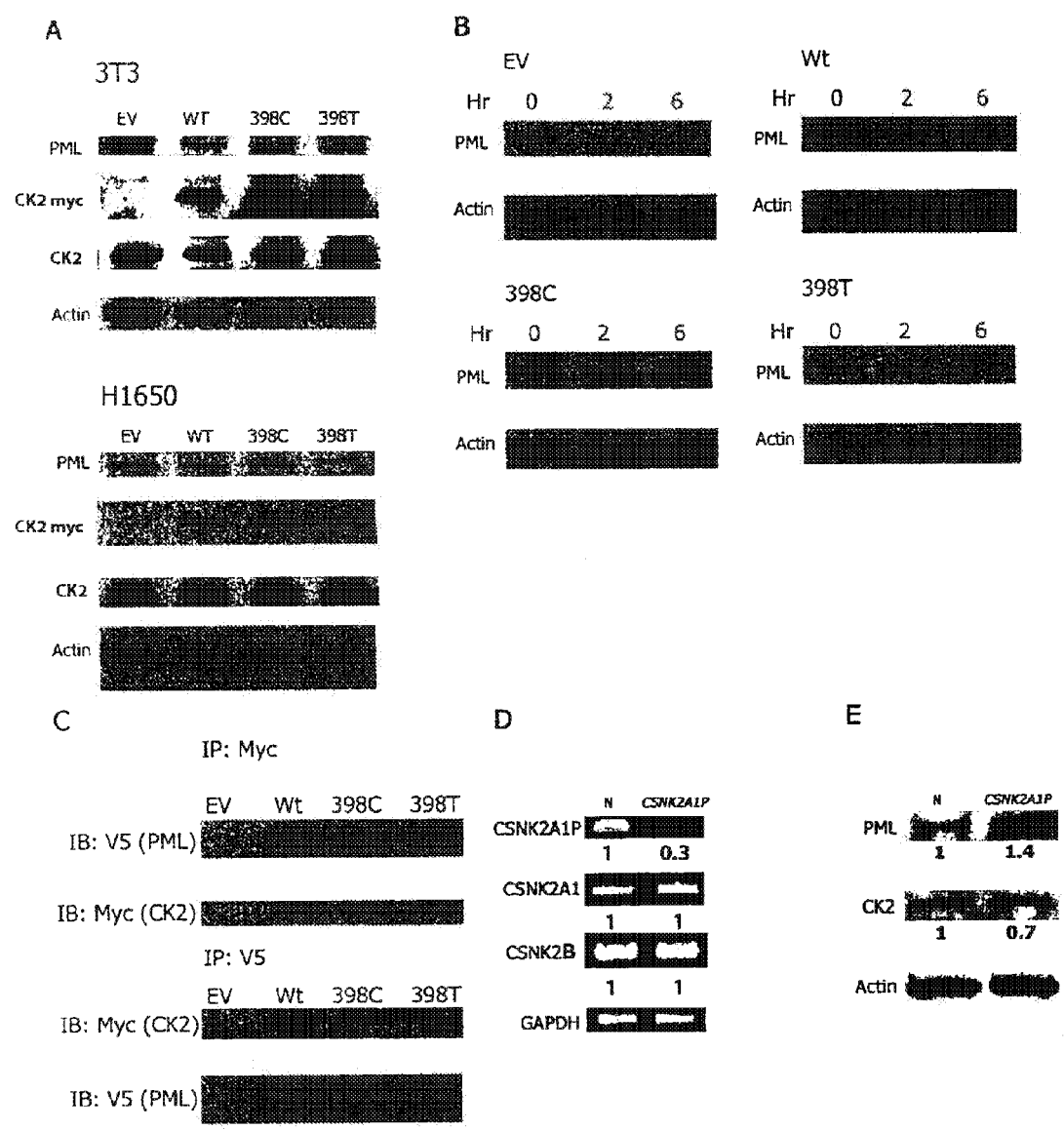

FIG. 11. FIG. 11 shows functional polymorphism of the CSNK2A1P genes on the degradation of PML tumor suppressor protein. (A) The PML protein decreases in NIH3T3 and H1650 stable cell lines that were transfected by the CSNK2A1 and CSNK2A1P genes. The endogenous CSNK2A1 protein and overexpressed CSNK2A1 and CSNK2A1P proteins were also shown. (B) Degradation of the PML protein is more prominent in NIH3T3 stable cell lines transfected with CSNK2A1 and CSNK2A1P (I133). Hr: hours after cycloheximide treatment. (C) 293T cells were co-transfected with PML-V5 and Myc-tagged CSNK2A1 or CSNK2A1P constructs. CSNK2A1 and CSNK2A1P (I133) show stronger binding to the PML protein in reciprocal immunoprecipitation assays. EV: empty vector. Wt: CSNK2A1. 398T: CSNK2A1P (I133) 398C: CSNK2A1P (I133T). (D) The expression of the CSNK2A1P gene decreases in the H1299 lung cancer cell line after transfection with the CSNK2A1P gene specific siRNA. No decrease in the expression of the CSNK2A1 and CSNK2B genes were noted. (E) The CK2α protein level decreases and the PML protein level increases in the H1299 lung cancer cell line after transfection with the CSNK2A1P gene specific siRNA. N: negative control siRNA. CSNK2A1P: CSNK2A1P siRNA. The band densities are normalized to the negative siRNA transfected group using actin as an internal control. All experiments were repeated three times with similar results.

DETAILED DESCRIPTION OF THE INVENTION

The present disclosure provides compositions and methods relating to diagnosis of a subject with a proliferative disorder are also provided by assessing CSNK2A1P status.

Protein kinase CK2 (formally known as casein kinase 2) is a serine/threonine protein kinase that phosphorylates more than 300 proteins, thereby affecting multiple cell signaling pathways, including the Wnt pathway. CK2 alpha (CK2 catalytic subunit) is a positive regulator and an essential component in the Wnt canonical signaling pathway, e.g., CK2 kinase activity promotes survival by increasing survivin expression via β-catenin-Tcf/Lef-mediated transcription. It was recently shown that multiple myeloma cell survival relies on high activity of protein kinase CK2.

The CK2 alpha 1 pseudogene or intronless gene (CSNK2A1P: casein kinase 2, alpha 1 polypeptide pseudogene; protein =(SEQ ID NO: 4); cDNA=(SEQ ID NO:3) is located on chromosome 11p15.3 (chromosome 11: 11329897-11331480) and has a strong promoter region (including two TATA boxes and a CAAT box). The gene, which is the same size as the wild type CSNK2A1 gene, 1.2 Kb (SEQ ID NO:1), shares 99% homology with the wild type CSNK2A1 cDNA.

It is shown herein that mutations and amplifications of the CSNK2A1P gene are present in a variety of human cancer cell lines and cancer tissues. One mutation, which falls within the kinase domain (398T->C; resulting in and I133T amino acid change, referred to herein as the CSNK2A1P I133T polymorphism) is shown herein to be a cancer-causing mutation, based on the Sorting Intolerant From Tolerant (SIFT) method. Additional mutations are also predicted herein to be common polymorphisms, by the SIFT method.

As shown herein, the CSNK2A1P gene is commonly overexpressed in cancer cells and tissues from cancer patients. No expression of this gene was detected in normal cells. Moreover, amplification of the CSNK2A1P gene has been detected in several cancer cell lines using FISH analysis.

In one aspect, the present disclosure provides CSNK2A1P-encoding polynucleotides, and fragments thereof, nucleic acid sequences encoding the CSNK2A1P I133T polymorphic variant, and fragments thereof, as well as other polymorphic variants and mutants of these proteins. In some aspects, the nucleic acids provided comprise vectors for expression in prokaryotic and eukaryotic host cells and lines. Also provided are polypeptide vectors for prophylactic and therapeutic use, such as gene therapy and siRNA/miRNA expression therapy.

Nucleic acids encoding CSNK2A1P and variants thereof, such as the I133T polymorphic variant, can comprise a vector (e.g., a cloning or expression vector). The vector may be, for example, a phage, plasmid, cosmid, bacmid, viral vector, and the like. The CSNK2A1P nucleic acids provided herein may be functionally linked to exogenous nucleic acids such as control sequences, expression sequences, or nucleic acids encoding protein fusion domains (i.e. for the expression of a CSNK2A1P fusion protein.

Polynucleotides encoding CSNK2A1P proteins, CSNK2A1P fusion proteins, or variants thereof, can further comprise a sequence encoding a peptide tag that further facilitates purification and/or detection, for example, a polyhitidine tag, a GST tag, a FLAG tag, an HA tag, a myc tag, a CBP tag, a TAP-tag, an MBP tag, and the like. The nucleic acids provided herein can further comprise a non-coding 5' and/or 3' sequence, such as transcribed, non-translated sequences, splicing and polyadenylation signals, ribosome binding sites, and sequences that stabilize mRNA.

Generally, recombinant expression vectors will include origins of replication and selectable markers permitting transformation of the host cell, e.g., the ampicillin resistance gene of E. coli and the S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others.

In addition, the expression vectors provided herein can further include additional elements. For example, the expression vector may have two replication systems, thus allowing it to be maintained in two organisms, e.g., mammalian and/or insect cells. Expression may be carried out in a prokaryotic host for cloning and amplification purposes. In another example, the vector is an integrating expression vector in which the expression vector contains at least one sequence homologous to the host cell genome, and preferably two homologous sequences that flank the expression construct. The integrating expression vector may be directed to a specific locus in the host cell by selecting the appropriate homologous sequence for inclusion in the vector.

Useful expression vectors for bacterial use can comprise a selectable marker and bacterial origin of replication derived from commercially available plasmids comprising genetic elements of well-known commercially available cloning vectors. Additional expression vectors useful in any of the methods of the present disclosure include retrovirus vectors (e.g., as described in WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), parvovirus based vectors such as adeno-associated virus (AAV) vectors, and adenoviral vectors.

Nucleic acids encoding CSNK2A1P and variants thereof, such as the I133T polymorphic variant, can also be used in other vectors known in the art including but not limited to vectors for producing gene disruptions ("knockouts"), antisense vectors, RNAi vectors (miRNA or siRNA), gene therapy vectors, viral vectors, and the like.

Host cells useful for the expression of CSNK2A1P and CSNK2A1P variants, such as I133T, include without limitation, a mammalian cell (e.g., a human-derived cell, a mouse cell, a CHO cell, a rodent cell), a yeast cell (e.g. a Saccharomyces cell, a Pichia cell, a Schizosaccharomyces cell, and the like), or a prokaryotic cell. Examples of appropriate hosts include, but are not limited to, bacterial cells, such as E. coli, Bacillis subtilis, Salmonella typhimurium, and various species within the genera Pseudomonas, Streptomyces, and Staphylococcus); archaebacteria; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, C129 cells, Neurospora, BHK, HeLa cells, Bowes melanoma cells, and human cells and cell lines. Methods for introducing nucleic acids and/or vectors into such host cells are well known in the art, and include transfection and electroporation, among others. These and other well-known methods can be used to produce recombinant cells through the introduction of nucleic acids and vectors.

The present disclosure also provides compositions of nucleotide probes that hybridize selectively to CNSK2A1P nucleotide sequences, polymorphic CNSK2A1P sequences, for example a T398C polymorphism, and variants thereof. Such probes can be used for diagnostic or research purposes. Numerous techniques are known in the art and can be used in the present disclosure to make such probes. In one example, Primer Express software from Applied Biosystems (Foster City, Calif.) is used to design probes that selectively bind to a polynucleotide encoding a CSNK2A1P I133T polymorphic at the site of the T398C mutation, and allow for its detection in a sample using standard TaqMan PCR methods. This technique is also used frequently for allelic discrimination, and is well known in the art. The sequence of both the wild type and the CSNK2A1P I133T polymorphic gene is entered into the Primer Express software program, and the region of the sequence containing the T398C mutation is highlighted. The exact position of the single nucleotide polymorphism is selected, and the software program generates candidate primer and probe sequences. Candidate probe sequences that meet the recommended guidelines for melting temperature and sequence characteristics are selected. The selected primers and probes can be ordered directly from Applied Biosystems, or can be produced synthetically according to techniques that are well known in the art. Candidate probes can then be tested for the ability to specifically bind to the CSNK2A1P I133T polymorphic sequence, thereby determining its presence in a sample. Other software programs or methods may be similarly used to design and produce nucleotide primers and probes that can distinguish between the wild type and polymorphic sequences, such as a CSNK2A1P I133T polymorphic sequence. Nucleotide probes that selectively hybridize to CSNK2A1P polymorphic sequences, such as the I133T polymorphism, can be used to test a sample from a patient in order to determine the abundance of the CSNK2A1P polymorphism (e.g. I133T) encoding polynucleotide present in the sample.

In another aspect, the present disclosure provides antibodies (e.g., monoclonal, polyclonal, poly-specific, or monospecific antibodies) specific for wildtype CSNK2A1P and CSNK2A1P protein variants, such as I133T, which can be used for diagnostic, or research purposes. Numerous methods for making antibodies are known in the art and can be used in the present disclosure to make such antibodies. In one example, a coding sequence for CSNK2A1P I133T polypeptide or fragment thereof is expressed as a C terminal fusion with glutathione S transferase (GST). The fusion protein is purified on glutathione Sepharose beads, eluted with glutathione, cleaved with thrombin (at an engineered cleavage site), and purified for immunization of rabbits. Primary immunizations are carried out with Freund's complete adjuvant and subsequent immunizations with Freund's incomplete adjuvant. Antibody titers are monitored by Western blot and immunoprecipitation analyses using the thrombin-cleaved protein fragment of the GST fusion protein Immune sera are affinity purified using CNBr Sepharose-coupled protein. Antiserum specificity can be determined using a panel of unrelated GST proteins.

As an alternate or adjunct immunogen to GST fusion proteins, peptides corresponding to relatively unique immunogenic regions of a polypeptide of the present disclosure can be generated and coupled to keyhole limpet hemocyanin (KLH) through an introduced C terminal lysine. Antiserum to each of these peptides is similarly affinity purified on peptides conjugated to BSA, and specificity is tested by ELISA or Western blot analysis using peptide conjugates, or by Western blot or immunoprecipitation using the polypeptide expressed as a GST fusion protein.

Alternatively, monoclonal antibodies that specifically bind a CSNK2A1P protein or variant thereof, e.g. a I133T polymorphic polypeptide, can be prepared using standard hybridoma technology. Once produced, monoclonal antibodies can also be tested for specific recognition by Western blot or immunoprecipitation analysis.

In addition to intact monoclonal and polyclonal anti-CSNK2A1P I133T antibodies, the present disclosure also includes various genetically engineered antibodies, humanized antibodies, chimeric antibodies, and antibody fragments, including minibodies, diabodies, triabodies, F(ab')2, Fab', Fab, Fv, sFv fragments, scFv's, and the like. Truncated versions of monoclonal antibodies, for example, can be produced by recombinant methods in which plasmids are generated that express the desired monoclonal antibody fragment(s) in a suitable host. Antibodies can be humanized by methods known in the art. Fully human antibodies, such as those expressed in transgenic animals, are also included in the present disclosure.

Antibodies that specifically recognize CSNK2A1P or a polymorphic variant thereof, for example an I133T polymorphic polypeptide, can be used, for example, in immunoassays, such as ELISAs to assess the presence or absence (qualitatively or quantitatively) of CSNK2A1P or a variant thereof (e.g. I133T) in a sample suspected of containing cancerous cells, e.g., for diagnosing or providing a prognosis for cancer, the likelihood of survival, the efficacy of a treatment, disease-free survival time, and the like.

Proliferative disorders that can be assessed according to any of the methods or compositions of the present disclosure include, cancers such as lung cancer (e.g., lung carcinoma, small cell lung carcinoma, non-small cell lung carcinoma, mesothelioma, bronchoalveolar carcinoma), leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, myeloma, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma), and the like.

In one aspect, CSNK2A1P polypeptides are provided herein. In certain embodiments, the CSNK2A1P polypeptides provided herein comprise an amino acid sequence that is at least 85% identical to the amino acid sequence of SEQ ID NO:4. In other embodiments, a CSNK2A1P polypeptide may comprise an amino acid sequence that is at least about 90%, or at least about 91%, 92%, 93%, 94%, 95%, 96%, 97%, 98%, or 99% identical to the amino acid sequence of SEQ ID NO:4. In one embodiment, the disclosure provides a CSNK2A1P polypeptide that comprises the amino acid sequence of SEQ ID NO:4.

In another aspect, a provided CSNK2A1P polypeptide comprises an I133T polymorphism. In certain embodiments, the CSNK2A1P polypeptides provided herein comprise an amino acid sequence that is at least 85% identical to the amino acid sequence of SEQ ID NO:4, wherein the polypeptide comprises an I133T amino acid substitution. In other embodiments, a CSNK2A1P polypeptide may comprise an amino acid sequence that is at least about 90%, or at least about 91%, 92%, 93%, 94%, 95%, 96%, 97%, 98% or 99% identical to the amino acid sequence of SEQ ID NO:6.

In one embodiment, the CSNK2A1P polypeptides provided herein may further comprise a tag that facilitates purification, detection, or both. Non-limiting examples of tags that are well known in the art include, polyhistidine tags, GST tags, Myc tags, TAP tags, HA tags, CBP tags, MBP tags, fluorescent protein tags, and the like. In another embodiment, a CSNK2A1P polypeptide provided herein may further comprise a fusion protein. Construction of fusion proteins is well known in the art.

In another aspect, polynucleotides encoding CSNK2A1P polypeptides are provided herein. In certain embodiments, the polynucleotides provided include DNA, RNA, and analogues thereof. In some embodiments, the polynucleotides provided herein comprise expression vectors suitable for expression of a CSNK2A1P polypeptide in a prokaryotic or eukaryotic host cell or organism. Non-limiting examples of suitable expression vectors include, plasmids, cosmids, bacmids, viral vectors, artificial chromosomes, mRNA for expression in an extract, and the like. In another embodiment, CSNK2A1P vectors are provided for gene therapy and therapeutic treatment purposes.

In another aspect, host cells harboring nucleic acids of the disclosure are provided. In certain embodiments, the provided host cell may comprise a polynucleotide, DNA, RNA, or an analogue thereof, that encodes a CSNK2A1 or CSNK2A1P polypeptide, for example a polypeptide having the amino acid sequence of SEQ ID NO:2, SEQ ID NO:4, or SEQ ID NO:6. Suitable host cells include prokaryotes, for example, a bacteria, and eukaryotes, for example, a yeast, a mammalian cell, a murine cell, a rodent cell, a human cell, a human cancer cell, and the like. In certain embodiments, host cells are provided that comprise an expression vector for a CSNK2A1 or CSNK2A1P polypeptide.

In another aspect, transgenic animals comprising a polynucleotide encoding a CSNK2A1 or CSNK2A1P polypeptide are provided. In certain embodiments, the transgenic animal can comprise a eukaryote, for example, an insect, a fish, or a mammal. In a particular embodiment, the transgenic animal is a mammal, such as a mouse, a rat, a guinea pig, a hamster, a rodent, a rabbit, a monkey, and the like. In certain embodiments, transgenic animals are provided that express a heterologous polypeptide comprising an amino acid sequence of SEQ ID NO:2, SEQ ID NO:4, SEQ ID NO:6, or a variant thereof. In a specific embodiment, the CSNK2A1P protein comprises an amino acid sequence that is at least 85% identical to an amino acid sequence of SEQ ID NO:4. In another embodiment, the CSNK2A1P protein comprises an I133T amino acid substitution.

In another aspect, polynucleotides are provided that specifically hybridize to a nucleic acid encoding a CSNK2A1 or CSNK2A1P polypeptide. In certain embodiments, a polynucleotide provided herein may specifically hybridize to a nucleic acid encoding a polypeptide having an amino acid sequence of SEQ ID NO:2, SEQ ID NO:4, SEQ ID NO:6, and variants thereof. In certain embodiments, a polynucleotide may specifically hybridize to a polynucleotide encoding one CSNK2A1 or CSNK2A1P polypeptide or variant thereof, but not to a second CSNK2A1 or CSNK2A1P polypeptide or variant thereof. For example, in one embodiment, a polynucleotide is provided that specifically hybridizes to a nucleic acid encoding a polypeptide having an amino acid sequence of SEQ ID NO:4 or SEQ ID NO:6, but does not specifically hybridize to a nucleic acid encoding a polypeptide having an amino acid sequence of SEQ ID NO:2. In this fashion, nucleic acids are provided that may distinguish between polynucleotides encoding CSNK2A1 and CSNK2A1P, or may distinguish between polynucleotides encoding different variants of CSNK2A1 or CSNK2A1P. In one example, a polynucleotide is provided that specifically hybridizes to a nucleic acid encoding a polypeptide having an amino acid sequence of SEQ ID NO:4, but does not specifically hybridize to a nucleic acid encoding a polypeptide having an amino acid sequence of SEQ ID NO:6. In another example, a polynucleotide is provided that specifically hybridizes to a nucleic acid encoding a polypeptide having an amino acid sequence of SEQ ID NO:6, but does not specifically hybridize to a nucleic acid encoding a polypeptide having an amino acid sequence of SEQ ID NO:4. In certain embodiments, the provided polynucleotides that may distinguish between polynucleotides encoding CSNK2A1 and CSNK2A1P, or between different variants of CSNK2A1 and CSNK2A1P proteins, may be about 10 nucleotides in length. In other embodiments, the polynucleotides may be about 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 90, 100, or more nucleotides. In certain embodiments, the polynucleotides may comprise DNA, RNA, or analogues thereof, for example an LNA analogue that promotes higher stability.

In another embodiment, polynucleotides are provided for modulating the expression of CSNK2A1 or CSNK2A1P. In certain embodiments, these nucleotides comprise siRNA, miRNA, antisense RNA, hammerhead ribozymes, or suitable analogues thereof. In some embodiments, these nucleic acids are suitable for research purposes, e.g. for modulating gene expression in a model organism. In other embodiments, these nucleic acids are suitable for therapeutic administration, e.g. for treatment of a human disease such as a CSNK2A1P-associated cancer.

In another aspect, antibodies are provided that specifically bind to a CSNK2A1 or CSNK2A1P polypeptide. In some embodiments, the antibody may specifically bind to a polynucleotide having an amino acid sequence of SEQ ID NO:2, SEQ ID NO:4, SEQ ID NO:6, or variants thereof. In certain embodiments, the antibodies may specifically bind to one CSNK2A1 or CSNK2A1P polypeptide, but not to another. For example, antibodies are provided that may bind to a CSNK2A1P polypeptide, for example, to a polypeptide comprising an amino acid sequence of SEQ ID NO:4 or SEQ ID NO:6, but not to a CSNK2A1 polypeptide, for example, to a polypeptide comprising an amino acid sequence of SEQ ID NO:2. In another example, antibodies are provided that can distinguish one CSNK2A1P polypeptide from another. For example, antibodies are provided that can specifically bind to a polypeptide comprising an amino acid sequence of SEQ ID NO:4, but not to a polypeptide comprising an amino acid sequence of SEQ ID NO:6.

In certain embodiments, the antibodies provided herein may be polyclonal antibodies, monoclonal antibodies, or fragments thereof. In some embodiments, the antibodies may comprise minibodies, diabodies, triabodies, scFv's, scFv-Fc's, fragments thereof, or any other antibody construct known in the art. In some embodiments, the antibodies of the invention may further comprise a detectable moiety, for example, a radioisotope, a fluorescent moiety, a conjugated enzyme, and the like. In other embodiments, the antibodies provided herein can further comprise a therapeutic moiety, such as a radioisotope, anti-cancer agent, and the like.

In another aspect, methods of diagnosing and providing a prognosis for cancer in a subject are provided. In certain embodiments, the methods comprise determining the expression level of CSNK2A1P in a biological sample from the subject, thereby diagnosing or providing a prognosis for cancer in the subject. In some embodiments of the methods provided herein, an increased level of CSNK2A1P is indicative of cancer, an increased risk of developing cancer, an increased risk of cancer recurrence, a reduced likelihood of long term survival, or a reduced likelihood of long term disease free survival in the subject.

In some embodiments, the level of CSNK2A1P expression is determined by measuring the level of CSNK2A1P mRNA in the biological sample. mRNA expression may be determined by any method known in the art, including without limitation, PCR, qPCR, RT-PCR, primer extension, hybridization, microarray, mass spectrometry, microsphere flow cytometry, and the like.

In another embodiment, the level of CSNK2A1P expression is determined by measuring the level of CSNK2A1P protein in the biological sample. Protein levels may be determined by any method known in the art, including without limitation, western blotting, ELISA, immunofluorescence, immunohistochemistry, and mass spectrometry.

In another embodiment, the methods provided herein comprise determining the CSNK2A1P gene copy number in a biological sample from the subject, thereby diagnosing or providing a prognosis for cancer in the subject. In some embodiments of the methods provided herein, an increased copy number of the CSNK2A1P gene is indicative of cancer, an increased risk of developing cancer, an increased risk of cancer recurrence, a reduced likelihood of long term survival, or a reduced likelihood of long term disease free survival in the subject.

In one embodiment, an increased copy number of the CSNK2A1P gene can be, for example, about 3 copies, or about 4, 5, 6, 7, 8, 9, 10, or more copies of a CSNK2A1P gene. In certain embodiments, the CSNK2A1P gene may comprise a wild type gene. In other embodiments, the CSNK2A1P gene may comprise a polymorphic or mutant the CSNK2A1P gene, for example, one that comprises a T398C nucleotide polymorphism.

In another embodiment, the methods provided herein comprise detecting a mutant or polymorphic CSNK2A1P gene in a biological sample from the subject, thereby diagnosing or providing a prognosis for cancer in the subject. In some embodiments of the methods provided herein, a mutant or polymorphic CSNK2A1P gene is indicative of cancer, an increased risk of developing cancer, an increased risk of cancer recurrence, a reduced likelihood of long term survival, or a reduced likelihood of long term disease free survival in the subject.

In some embodiments, the mutant or polymorphic CSNK2A1P gene comprises a T398C nucleotide polymorphism. In certain embodiments, the mutant or polymorphic CSNK2A1P gene may be detected by determining the sequence of one or more of the CSNK2A1P alleles in a biological sample, or by detecting a mutant or polymorphic CSNK2A1P alleles in a biological sample. In one specific embodiment, the polymorphic CSNK2A1P gene comprises a T398C nucleotide polymorphism. In other embodiments, the mutant or polymorphic CSNK2A1P gene may be detected by determining the sequence of a CSNK2A1P polypeptide in the biological sample, or by detecting a mutant or polymorphic CSNK2A1P polypeptide in the biological sample. In a specific embodiment, the CSNK2A1P protein comprises an I133T mutation.

In certain embodiments, the diagnostic and prognostic methods provided herein further comprise the step of providing information comprising an estimate of the likelihood of survival, an estimate of the likelihood of cancer recurrence, an estimate of the time for which the subject will remain cancer free, or an estimate of the likelihood of long term survival. Generally, these estimates are associated with the CSNK2A1P status of the subject or biological sample taken from the subject.

In certain embodiments, the methods of diagnosing and providing a prognosis for cancer in a subject, are for a CSNK2A1P-associated cancer. Non-limiting examples of cancers that may be diagnosed or for which a prognosis may be provided according to the methods of the disclosure include, lung cancer, colon cancer, cervical cancer, lymphatic cancer, skin cancer, pancreatic cancer, brain cancer, head and neck cancer, leukemia, and the like. In one embodiment, the cancer is lung cancer, including without limitation, non-small cell lung carcinoma (NSCLC), small cell lung carcinoma, large cell carcinoma, a carcinoid, a sarcoma, a mesothelioma, squamous cell lung carcinoma, adenocarcinoma, bronchioloalveolar carcinoma, metastases to the lung, and the like.

In another aspect, methods of assessing the efficacy of a therapeutic treatment for a CSNK2A1P-associated disease or condition are provided. In a certain embodiment, the disease is cancer. In one embodiment, the method comprises expressing a heterologous CSNK2A1P protein in a mammal, administering a therapeutic treatment to the mammal, and determining an effect of the treatment on the mammal, thereby assessing the efficacy of the therapeutic treatment.

In some embodiments, the therapeutic treatment is selected from the group consisting of chemotherapy, radiation therapy, hormone therapy, surgery, or a combination thereof. In certain embodiments, determining the effect of the therapeutic treatment comprises detecting a difference in CSNK2A1P activity, including without limitation, CSNK2A1P expression, phosphorylation, protein stability, and the like, after administration of the therapeutic treatment.

In one specific embodiment, the method comprises detecting a difference in CSNK2A1P-mediated phosphorylation of a substrate. Suitable substrates include, without limitation, PML, AKT, ATF-1, BRCA1, and peptide substrates thereof. Other suitable substrates are know in the art (see, for example, Meggio F and Pinna L A, FASEB J. 2003 March; 17(3):349-68).

In other embodiments, determining the effect of the therapeutic treatment comprises detecting a change in the growth rate, size, or mass of a tumor expressing CSNK2A1P in the mammal. In certain embodiments, the methods comprise generating a xenographic mammal, such as a mouse or other rodent. In some embodiments, the xenograph will comprise a tumor, cancerous mass, and the like, which expresses CSNK2A1P or a variant thereof.

In another aspect, methods of identifying therapeutic compounds are provided. In one embodiment, the method comprises assessing an effect of a compound on a cell expressing a CSNK2A1P protein. In a specific embodiment, the method comprises the steps of expressing a heterologous CSNK2A1P protein in a cell, administering a compound to the cell, and determining an effect of the compound, thereby assessing the effect of the compound on a cell expressing a CSNK2A1P protein. In certain embodiments, the effect is a change in the transcription, translation, or activity of a CSNK2A1P protein or variant. In some embodiments, the method comprises screening a plurality or library of small molecules. In certain embodiments, the compound is selected from the group consisting of a nucleic acid, an antibody or fragment thereof, a peptide, or a small molecule.

Diagnostic and Prognostic Methods

Nucleic acid molecules encoding mutant CSNK2A1P or CSNK2A1, as well as polypeptides encoded by these nucleic acids, and antibodies specific for these polypeptides, can be used in methods and kits for diagnosing, providing a prognosis, or monitoring diseases and conditions involving overexpression or inappropriate activity of, CSNK2A1P and variants thereof.

The diagnostic and prognostic methods and kits of the present disclosure can be used, for example, with patients who have or are suspected of having a cancer affected by CSNK2A1P status (a CSNK2A1P-associated cancer) in an effort to determine its etiology and, thus, to facilitate selection of an appropriate course of treatment. The diagnostic methods can be used with patients who have not yet developed, but who are at risk of developing, such a cancer, or with patients who are at an early stage of cancer. The methods of the present disclosure can be used to diagnose the disorders described herein in any mammal, for example, in humans, domestic pets, or livestock. Human subjects are of particular interest.

CSNK2A1P status can be assessed by assaying for one or more of: (i) an expression level of a CSNK2A1P RNA transcript or expression product thereof, where assays can provide for detection of wildtype CSNK2A1P RNA transcripts or expression products, CSNK2A1P I133T RNA transcripts or expression products; or both; (ii) assaying for copy number of a gene encoding a CSNK2A1P, where such assaying can involve detection of a gene encoding wildtype CSNK2A1P, CSNK2A1P I133T, or either wildtype CSNK2A1P or CSNK2A1P I133T; and (iii) the presence or absence of a CSNK2A1P I133T RNA transcript or expression product thereof.

As noted above, in addition to facilitating diagnosis of an existing disease or condition, mutation detection assays also provide an opportunity to diagnose a predisposition to a disease related to a mutation in a CSNK2A1P gene before the onset of symptoms. For example, a patient who is heterozygous for a gene encoding CSNK2A1P I133T protein may show no clinical symptoms of a disease related to such proteins, and yet possess a higher than normal probability of developing such disease. Given such a diagnosis, a patient can take precautions to minimize exposure to adverse environmental factors, and can carefully monitor his/her medical condition, for example, through frequent physical examinations. As mentioned above, this type of diagnostic approach can also be used to detect a mutation in a gene encoding the CSNK2A1P protein in prenatal screens.

Diagnostic methods for detecting a wildtype CSNK2A1P gene or CSNK2A1P I133T polymorphic gene can be accomplished using genomic DNA from readily accessible tissues, and/or by assaying mRNA encoding wildtype CSNK2A1P or CSNK2A1P I133T from tissue samples in which it is expressed. Expression levels can be determined by using any of a number of standard techniques that are well known in the art, including northern blot analysis and quantitative PCR (see, e.g., Ausubel et al., supra; PCR Technology: Principles and Applications for DNA Amplification, H. A. Ehrlich, Ed., Stockton Press, NY; Yap et al. Nucl. Acids. Res. 19:4294, 1991).

The present disclosure provides methods of diagnosing and providing a prognosis for a CSNK2A1P-associated cancer by examining the presence of, expression of, or allele status of CSNK2A1P polynucleotides and polypeptides, including wild-type, truncated or alternatively spliced forms. In some embodiments, diagnosis involves determining the level of a polynucleotide or polypeptide of the disclosure in a patient and then comparing the level to a baseline or range. Typically, the baseline value is representative of a polynucleotide or polypeptide of the disclosure in a healthy person not suffering from a CSNK2A1P-associated cancer or from a non-cancerous cell. Variation of levels of a polynucleotide or polypeptide of the invention from the baseline range (either up or down) indicates that the patient has a CSNK2A1P-associated cancer, is at risk of developing a CSNK2A1P-associated cancer, is at risk of recurrence of a CSNK2A1P-associated cancer, is at risk for a reduced likelihood of long-term survival, or is at risk for a reduced likelihood of long-term cancer free survival.

PCR assays such as Taqman® allelic discrimination assay available from Applied Biosystems can be used to identify RNA. In another embodiment, mass spectroscopy can be used to detect either nucleic acid or protein. Any antibody-based technique for determining a level of expression of a protein of interest can be used. For example, immunoassays such as ELISA, Western blotting, flow cytometry, immunofluorescence, and immunohistochemistry can be used to detect protein in patient samples. Combinations of the above methods, such as those employed in the Luminex® xMAP technology can also be used in the methods provided herein.

RT-PCR is commonly used. RT-PCR can be used to compare mRNA levels in different sample populations, in normal and tumor tissues, to characterize patterns of gene expression, to discriminate between closely related mRNAs, and to analyze RNA structure.

Since RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signals from the released reporter dye are free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 SEQUENCE DETECTION SYSTEM (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 SEQUENCE DETECTION SYSTEM. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

A more recent variation of the RT-PCR technique is the real time quantitative PCR, which measures PCR product accumulation through a dual-labeled fluorigenic probe (i.e., TAQMAN probe). Real time PCR is compatible both with quantitative competitive PCR, where internal competitors for each target sequence are used for normalization, and with quantitative comparative PCR using a normalization gene contained within the sample, or a reference gene for RT-PCR. For further details see, e.g. Held et al., *Genome Research* 6:986-994 (1996).

Factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. can be used.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T.N. "Primerselect: Primer and probe design." *Methods Mol. Biol.* 70:520-527 (1997), the entire disclosures of which are hereby expressly incorporated by reference.

Analysis of a protein or nucleic acid can be achieved, for example, by high pressure liquid chromatography (HPLC), alone or in combination with mass spectrometry (e.g., MALDI/MS, MALDI-TOF/MS, tandem MS, etc.).

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)). Liposome immunoassays, such as flow-injection liposome immunoassays and liposome immunosensors, are also suitable for use in the methods provided herein (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the methods provided herein. Nephelometry assays are commercially available from Beckman Coulter (Brea, Calif.; Kit #449430) and can be performed using a Behring Nephelometer Analyzer (Fink et al., *J. Clin. Chem. Clin. Biochem.*, 27:261-276 (1989)).

Specific immunological binding of the antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), □-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm Similarly, a □-galactosidase detection system can be used with the chromogenic substrate o-nitrophenyl-□-D-galactopyranoside (ONPG), which yields a soluble product detectable at 410 nm. An urease detection system can be used with a substrate such as urea-bromocresol purple (Sigma Immunochemicals; St. Louis, Mo.).

A signal from a direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as polystyrene beads, magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different biomarkers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

Analysis of the level of a biomarker can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

The present disclosure provides methods for diagnosing and determining a prognosis of disease-free or overall survival in a patient suffering from cancer, methods for determining the proper course of treatment for a patient suffering from cancer, and kits for use in practicing the same.

Determining CSNK2A1P Status

CSNK2A1P status of a tumor is correlated with likelihood of survival of a subject. As noted above, "CSNK2A1P status" as used herein refers to status of CSNK2A1P activity in a tumor cell, which can be assessed by one or more of an expression level of a CSNK2A1P RNA transcript or its expression product (and thus encompasses CSNK2A1P polypeptides levels), CSNK2A1P gene copy number, and the presence or absence of a CSNK2A1P polymorphism or mutation, such as a I133T polymorphism.

In general, CSNK2A1P status is correlated with likelihood of survival. For example, high normalized values of CSNK2A1P mRNA, polypeptide levels, as well as the presence of a CSNK2A1P I133T polymorphism, are inversely correlated with increased likelihood of survival, and thus are directly correlated with poor prognosis. Conversely, a higher likelihood of disease-free or overall survival is directly correlated with lower normalized values of CSNK2A1P gene expression, CSNK2A1P polypeptide levels, and the absence of detectable mutant or polymorphic CSNK2A1P genes and proteins, such as the I133T polymorphism.

For example, CSNK2A1P expression in a tumor is inversely correlated with a subject's likelihood of survival, including tumor recurrence and/or aggressiveness. A higher likelihood of disease-free or overall survival generally correlates with lower normalized values of CSNK2A1P gene expression, lower CSNK2A1P polypeptide levels, low copy number for a CSNK2A1P gene, and the absence of a mutant or polymorphic CSNK2A1P, for example the I133T polymorphic variant. Conversely, higher normalized values of CSNK2A1P gene expression, higher CSNK2A1P polypeptide levels, higher copy number for a CSNK2A1P gene, and the presence of a mutant or polymorphic CSNK2A1P, for example the I133T polymorphic variant, correlates with a low likelihood of survival, and thus poor prognosis. Thus, the level of CSNK2A1P expression and gene copy number may be used as the sole factor, or in combination with additional factors, such as lymph node status, in assessing the disease status and prognosis of cancer patients.

Determination of CSNK2A1P status may be performed by one or more of the following exemplary methods known to one of ordinary skill in the art. For example, CSNK2A1P expression levels may be determined by (a) detection of an CSNK2A1P gene product, such as mRNA encoding an CSNK2A1P protein; and/or (b) detection of CSNK2A1P gene copy number. Any combination of these techniques can be used to assess patient prognosis and likelihood of overall survival.

Detecting and Quantifying CSNK2A1P RNA Transcripts

Detection of levels of mRNA encoding CSNK2A1P polypeptides generally serves as an indicator of CSNK2A1P expression. Methods used to detect mRNA levels include the detection of hybridization or amplification with the mRNA encoding CSNK2A1P. In general, this detection may be carried out by analysis of mRNA either in vitro or in situ (e.g., in a tissue sample) using one of the methods known to one of ordinary skill in the art as exemplified in Ausubel et al., *Current Protocols in Molecular Biology* (John Wiley & Sons, 1999); in U.S. Pat. No. 5,882,864; and the like.

Sample Extraction and Preparation

In some embodiments, the first step in the determination of CSNK2A1P gene expression levels through detection CSNK2A1P mRNA, is the isolation of mRNA from a patient sample. The sample can be any suitable biological sample from the subject which is suspected of containing cancer cells. Methods for obtaining samples and isolated mRNA are known in the art. For example, with respect to solid tumors, isolation may be performed by for example, core needle biopsy, fine needle aspiration, and the like. While the source of mRNA is a primary tissue, mRNA can be extracted, for example, from stored samples, e.g., from frozen or archived paraffin-embedded and fixed (e.g. formalin-fixed) tissue samples. RNA can be isolated from a variety of primary tumors, including lung, colon, breast, prostate, brain, liver, kidney, pancreas, spleen, thymus, testis, ovary, uterus, head and neck tumors, etc., or from tumor cell lines.

In certain embodiments, after a biological sample is obtained and processed, as desired, it is then subjected to a detection method that is compatible with the gene product to be assessed (e.g., RNA transcript or expression product thereof, CSNK2A1P gene methylation status, gene copy number, polypeptide levels, etc.).

Methods for RNA extraction from paraffin embedded tissues are disclosed, for example, in Rupp and Locker, *Lab Invest*. 56:A67 (1987), and De Andrés et al., *BioTechniques* 18:42044 (1995). In particular, RNA isolation can be performed using a purification kit, buffer set and associated proteases from commercial manufacturers, such as Qiagen, according to the manufacturer's instructions. For example, total RNA from cells in culture can be isolated using Qiagen RNeasy mini-columns. Other commercially available RNA isolation kits include MASTERPURE Complete DNA and RNA Purification Kit (EPICENTRE, Madison, Wis.), and Paraffin Block RNA Isolation Kit (Ambion, Inc.). Total RNA from tissue samples can be isolated using RNA Stat-60 (Tel-Test). RNA prepared from tumor samples can also be isolated, for example, by cesium chloride density gradient centrifugation.

CSNK2A1P Polypeptide Detection

CSNK2A1P status can also be assessed by detection of a CSNK2A1P polypeptide in a biological sample. In one embodiment, polyclonal or monoclonal antibodies specific for the CSNK2A1P protein (wildtype CSNK2A1P, CSNK2A1P I133T polymorphism, or both) can be used in any standard immunoassay format (e.g., ELISA, Western blot, RIA, and the like) to assess polypeptide levels. Where desired, these levels can be compared to levels of CSNK2A1P in a sample from an unaffected individual, an unaffected tissue in the same individual, or some other reference sample. Detection of an increase in production of CSNK2A1P using this method, for example, may be indicative of a condition or a predisposition to a condition involving elevated activity of CSNK2A1P protein.

Methods of measuring a level of a polypeptide gene product are known in the art and include antibody-based methods such as enzyme-linked immunoabsorbent assay (ELISA); radioimmunoassay (RIA); protein blot analysis; immunohistochemical analysis; and the like. Such methods also include proteomics methods, such as mass spectrometric methods, which are known in the art.

In one embodiment, immunohistochemical techniques can also be utilized for detection of a CSNK2A1P polypeptide in a sample. For example, a tissue sample can be obtained from a patient, sectioned, and stained for the presence of CSNK2A1P polypeptides or polynucleotides using anti-CSNK2A1P antibodies or polynucleotide probes (or anti-CSNK2A1P variant, such as a I133T polymorphic variant, antibodies or polynucleotide probes) and any standard detection system (e.g., one that includes a secondary antibody conjugated to an enzyme, such as horseradish peroxidase, or a fluorescently labeled secondary antibody or polynucleotide probe). General guidance regarding such techniques can be found in, e.g., Bancroft et al., Theory and Practice of Histological Techniques, Churchill Livingstone, 1982, and Ausubel et al., supra.

Those of skill in the art will recognize that it is also possible to measure levels of CSNK2A1P proteins in body fluid, such as serum. Tumors are known to readily shed cells which, after release into the bloodstream, may burst due to cell fragility. Thus, detection of any CSNK2A1P levels, present in body fluid (e.g., serum) is contemplated for use in the provided methods of diagnosing and providing a prognosis for cancer in a subject, including determine a prognosis of disease-free or overall survival in a manner analogous to that demonstrated with the tissue samples. Very small quantities of CSNK2A1P polynucleotides and polypeptides can be measured in body fluid, for example, using anti-CSNK2A1P antibodies in immuno-PCR methods as described herein.

Accordingly, it is contemplated herein that the reference levels may represent the level of CSNK2A1P present in a body fluid sample, such as serum. Accordingly, methods are provided herein that measure the level of circulating CSNK2A1P (i.e., the level of CSNK2A1P in blood or serum), will have a particularly preferred application to early diagnosis and screening, and early determination of risk of cancer recurrence or spread, for patients with abnormal levels of CSNK2A1P in their serum.

Normalization Methods

In carrying out a method provided herein, a level of a gene product in a sample from a patient is assayed. The level of the gene product is then "normalized," generating a normalized expression level of the gene product. The gene product is one that has been identified as predictive of patient prognosis and/or long term survival.

Quantitative RT-PCR is usually performed using an internal standard, or one or more reference genes. The ideal internal standard is expressed at a constant level among different tissues, and is unaffected by the experimental treatment.

Suitable reference genes include, but are not limited to, glyceraldehyde-3-phosphate dehydrogenase (GAPDH) (see, e.g., GenBank Accession No. NM_002046), beta-actin, and 18S genes (see, e.g., Eisenberg and Levanon (2003) Trends in Genetics 19:362, for a list of additional suitable reference genes).

Calculating a Normalized Value for Gene Products

The level of an RNA transcript as measured by TAQMAN RT-PCR or TAQMAN PCR generally refers to the cycle threshold (Ct) value. The lower the Ct, the greater the amount of mRNA present in the sample. The expression value of a RNA transcript in a sample is normalized, e.g., by first determining the mean expression value in Ct of designated reference genes in a sample ($Ct_{Ref}$). The normalized expression value for a gene ($Ct_{Gene}$) is then calculated as $Ct_{Gene}-Ct Ct_{Ref}$. Optionally, the normalized expression values for all genes can be adjusted, e.g., so that all adjusted normalized Ct have a value >0.

Methods Involving Assessment of CSNK2A1P Expression Levels

The data obtained from assessing CSNK2A1P expression status can be applied to a variety of uses, including facilitating an assessment of likelihood of survival, guidance in selection of treatment options, classification of subjects for purpose of clinical trial design, and the like.

In some embodiments, subjects suitable for analysis of CSNK2A1P expression include humans, mice, rats, gerbils, guinea pigs, rodent, other mammals, such as non-human primates, and non-primate mammals, including veterinary and livestock subjects.

In some embodiments, subjects suitable for CSNK2A1P expression analysis include subjects having or suspected of having a CSNK2A1P-associated cancer. Such subjects thus can include those diagnosed as having or suspected of having, a neoplastic disease or tumor such as lung cancer (e.g., non-small cell lung carcinoma, bronchioloalveolar carcinoma, mesothelioma, and the like) colon cancer, skin cancer (e.g., melanoma), or esophageal cancer. In some embodiments, the cancer is other than an endometrial cancer or a testicular cancer. Subjects may have solid or cystic tumors, or diffuse disease. Subjects may have a primary occurrence of cancer as well as localized and metastasized cancer at various stages.

In certain embodiments, the patient can have or be suspected of having any stage of a cancer. As used herein, the term "stage", when applied to tumor development, refers to the degree of progression of a tumor. Various stages of tumor development are well known to those of skill in the art, as exemplified in Markman 1997, Basic Cancer Medicine. Stages of different cancers are defined according to different criteria, typically using the Tumor-Node-Metastasis (TNM) system. For example, stage I of lung cancer requires no detectable lymph node involvement, and stage II of lung cancer involves either no detectable lymph node involvement and a large primary tumor, or initial lymph node involvement and a small primary tumor. Similar descriptions of the various clinical stages can be found in Markman, supra, for breast cancer, and prostate cancer, colon cancer and ovarian cancer. Early stages of tumor development shall be understood to refer to stages in tumor development in which the tumor has detectably spread no further than the lymph nodes local to the organ of the primary tumor. Typically, early stages will be considered to be stages I and II. As used herein, the phrase, "prior to lymph node involvement" refers to the detectable presence of cancer cells in the organ of the primary tumor, but the lack of a detectable presence of cancer cells in any lymph nodes, including the lymph nodes closest to the organ of the primary tumor.

Treatment Options

In certain embodiments, CSNK2A1P status can be used to guide selection of therapy for a subject. For example, if a patient is classified as having high CSNK2A1P gene expression levels and thus a poor likelihood of survival, a more aggressive treatment regimen and/or more frequent monitoring of disease progression could be recommended. If a patient is classified as having low CSNK2A1P gene expression levels, and thus a good likelihood of survival, then this can inform therapy selection as well, and may suggest that less radical therapy may be required.

Cancer treatments include, without limitation, radiation therapy, surgical removal of a tumor, laser ablation therapy, and chemotherapeutic regimens. For example, suitable treatments for a colorectal cancer patient include, e.g., chemotherapy with 5-fluorouracil alone or in combination with a platinum based chemotherapeutic compound such as oxaliplatin. As another example, suitable alternative treatments for a head and neck cancer patient include, e.g., a platinum-based chemotherapeutic agent (e.g., cisplatin (cis-DDP), carboplatin, etc.); leucovorin; fluorouracil (5-FU); or combinations such as cisplatin +5-FU; and a taxane (e.g., paclitaxel). As another example, suitable alternative treatments for a non-small cell lung cancer patient include, e.g., a platinum-based chemotherapeutic agent (e.g., cisplatin (cis-DDP), carboplatin, etc.); or leucovorin; and a platinum-based chemotherapeutic agent in combination with a second agent such as gemcitabine, paclitaxel, docetaxel, etoposide or vinorelbine.

Analysis Results Reporting

As discussed above, in certain embodiments, the likelihood that a patient will exhibit a certain prognosis is assessed by determining CSNK2A1P status (e.g., a normalized expression level of the CSNK2A1P gene, presence or absence of a CSNK2A1P polymorphism or mutation, e.g. a I133T variant, increased CSNK2A1P gene copy number, and the like). In some embodiments, a patient's likelihood of survival is provided in a report. Thus, in some embodiments, a subject method further includes a step of preparing or generating a report that includes information regarding the patient's likelihood of survival. For example, a subject method can further include a step of generating or outputting a report providing the results of a survival likelihood assessment, which report can be provided in the form of an electronic medium (e.g., an electronic display on a computer monitor), or in the form of a tangible medium (e.g., a report printed on paper or other tangible medium).

A report that includes information regarding the likelihood that a patient will survive is provided to a user. An assessment as to the likelihood that a patient will survive is referred to below as a "survival likelihood assessment" or, simply, "likelihood assessment." A person or entity who prepares a report ("report generator") will also perform the likelihood assessment. The report generator may also perform one or more of sample gathering, sample processing, and data generation, e.g., the report generator may also perform one or more of: a) sample gathering; b) sample processing; c) assessing CSNK2A1P status; d) measuring a level of a reference gene product(s); and e) determining a CSNK2A1P gene status. Alternatively, an entity other than the report generator can perform one or more sample gathering, sample processing, and data generation.

For clarity, it should be noted that the term "user," which is used interchangeable with "client," is meant to refer to a person or entity to whom a report is transmitted, and may be the same person or entity who does one or more of the following: a) collects a sample; b) processes a sample; c) provides a sample or a processed sample; and d) generates data relating to CSNK2A1P status (e.g., level of CSNK2A1P gene product(s); level of a reference gene product(s); normalized level of CSNK2A1P gene product(s)) for use in the likelihood assessment. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician (e.g., an oncologist), etc.).

In embodiments where the user only executes a portion of the method, the individual who, after computerized data processing according to the methods of the invention, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Reports

A "report," as described herein, is an electronic or tangible document which includes report elements that provide information of interest relating to a subject likelihood assessment and its results. A subject report includes at least a likelihood assessment, e.g., an indication as to the likelihood that a patient cancer will survive. A subject report can be completely or partially electronically generated. A subject report can further include one or more of: 1) information regarding the testing facility; 2) service provider information; 3) patient data; 4) sample data; 5) an interpretive report, which can include various information including: a) indication; b) test data relating to CSNK2A1P status, where test data can include, for example, normalized levels of CSNK2A1P gene products; and/or 6) other features.

Where government regulations or other restrictions apply (e.g., requirements by health, malpractice, or liability insurance), all results, whether generated wholly or partially electronically, are subjected to a quality control routine prior to release to the user.

Testing Facility Information

The report can include information about the testing facility, which information is relevant to the hospital, clinic, or laboratory in which sample gathering and/or data generation was conducted. Sample gathering can include obtaining a cancer cell sample from a biopsy, a surgically removed tumor, surgically removed tissue comprising a tumor, or other tissue or bodily fluid from a patient. Data generation can include one or more of: a) measuring a level of a gene product(s); and b) determination of CSNK2A1P gene status. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

Service Provider Information

The report can include information about the service provider, which may be located outside the healthcare facility at which the user is located, or within the healthcare facility. Examples of such information can include the name and location of the service provider, the name of the reviewer, and where necessary or desired the name of the individual who conducted sample gathering and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

Patient Data

In certain embodiments, the patient data can include patient medical history (which can include, e.g., data about prior treatment for cancer), personal history; administrative patient data (that is, data that are not essential to the likelihood assessment), such as information to identify the patient (e.g., name, patient date of birth (DOB), gender, mailing and/or residence address, medical record number (MRN), room and/or bed number in a healthcare facility), insurance information, and the like), the name of the patient's physician or other health professional who ordered the assessment and, if different from the ordering physician, the name of a staff physician who is responsible for the patient's care (e.g., primary care physician). Report fields with this information can generally be populated using data entered by the user.

Sample Data

The sample data can provide information about the biological sample analyzed in the likelihood assessment, such as the source of biological sample obtained from the patient (e.g., tumor biopsy, surgically removed tumor, unknown, etc.) and the date and time collected. Report fields with this information can generally be populated using data entered by the user, some of which may be provided as pre-scripted selections (e.g., using a drop-down menu).

Interpretive Report

The interpretive report portion of the report includes information generated after processing of the data as described herein. The interpretive report can include an indication of patient prognosis. The interpretive report can include, for example, Indication (e.g., type of cancer, etc.); Result of screen for CSNK2A1P 133T (e.g., "Negative for CSNK2A1P I133T"); Result of assessment of CSNK2A1P status (e.g., "normalized level of CSNK2A1P gene product(s)" and/or "CSNK2A1P copy number"); Interpretation; and, optionally, Recommendation(s) (e.g., options for therapy).

It will be readily appreciated that the report can include all or some of the elements above, with the proviso that the report generally includes at least the elements sufficient to provide the analysis requested by the user (e.g., likelihood assessment).

Additional Features

It will also be readily appreciated that in some embodiments, the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting.

Computer-Based Systems and Methods

The methods and systems described herein can be implemented in numerous ways. In one embodiment of particular interest, the methods involve use of a communications infrastructure, for example the interne. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of an CSNK2A1P gene product (which may include assessment of pooled wildtype CSNK2A1P and CSNK2A1P I133T expression, or assessment of wildtype CSNK2A1P or CSNK2A1P I133T polymorphism, and which may be further normalized relative to one or more reference genes); presence or absence of a CSNK2A1P I133T polymorphism gene expression product (e.g., CSNK2A1P I133T polypeptide detection); level of a reference gene product(s); and the like); and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present invention.

Where used, the database(s) is usually connected to the database server component and can be any device which will hold data. For example, the database can be a any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The invention also contemplates a computer-readable storage medium (e.g. CD-ROM, memory key, flash memory card, diskette, etc.) having stored thereon a program which, when executed in a computing environment, provides for implementation of algorithms to carry out all or a portion of the results of an assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the interne, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying out prognosis assessment (e.g., primers, probes, arrays, or other such kit components).

Arrays

In one aspect, the present invention provides arrays for use in carrying out a method of assessing prognosis of patient based on CSNK2A1P expression levels. A subject array includes a plurality of polynucleotides immobilized on the surface of an insoluble support. The immobilized polynucleotides comprise nucleotide sequences that are capable of hybridizing with a reference gene or CSNK2A1P (where the nucleic acid can provide for detection of nucleic acid encoding a wildtype CSNK2A1P, a mutant or polymorphic CSNK2A1P, such as a I133T variant, or combinations thereof). Generation of probes that hybridize under suitable hybridization conditions (e.g., stringent hybridization conditions) is well within the skill level of those of ordinary skill in the art.

In certain embodiments, a CSNK2A1P gene may be represented on the array by probes immobilized on an insoluble support. It may represent at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, or at least about 95% of the genes represented on the array.

A probe can be "addressable," e.g., the nucleotide sequence, or perhaps other physical or chemical characteristics, of a probe can be determined from its address, i.e. a one-to-one correspondence between the sequence or other property of the probe and a spatial location on, or characteristic of, the solid phase support to which it is attached. For example, an address of a probe can be a spatial location, e.g. the planar coordinates of a particular region containing copies of the probe.

A subject array includes a solid phase support, which may be planar or a collection of microparticles, that carries or carry probes as described above fixed or immobilized, e.g., covalently, at specific addressable locations. For example, a subject array includes a solid phase support having a planar surface, which carries a plurality of nucleic acids, each member of the plurality comprising identical copies of an oligonucleotide or polynucleotide probe immobilized to a fixed region, which does not overlap with those of other members of the plurality. Typically, the nucleic acid probes are single stranded and are covalently attached to the solid phase support at known, determinable, or addressable, locations. The density of non-overlapping regions containing nucleic acids in a microarray is typically greater than 100 per cm2, e.g., greater than 1000 per cm2.

The substrates of the subject arrays may be fabricated from a variety of materials. The materials from which a substrate is fabricated should ideally exhibit a low level of non-specific binding during hybridization events. In many situations, it will also be preferable to employ a material that is transparent to visible and/or LTV light. For flexible substrates, materials of interest include: nylon, both modified and unmodified, nitrocellulose, polypropylene, and the like, where a nylon membrane, as well as derivatives thereof, is of particular interest in this embodiment. For rigid substrates, specific materials of interest include: glass; plastics, e.g. polytetrafluoroethylene, polypropylene, polystyrene, polycarbonate, and blends thereof, and the like; metals, e.g. gold, platinum, and the like; etc. Also of interest are composite materials, such as glass or plastic coated with a membrane, e.g. nylon or nitrocellulose, etc.

Hybridization between a probe and a test nucleic acid (where a test nucleic acid includes a nucleic acid sample obtained from a cancer cell from a patient) results in a "readout," where "readout" refers to a parameter, or parameters, which are measured and/or detected that can be converted to a number or value. In some contexts, readout may refer to an actual numerical representation of such collected or recorded data. For example, a readout of fluorescent intensity signals from an array is the address and fluorescence intensity of a signal being generated at each hybridization site of the array; thus, such a readout may be registered or stored in various ways, for example, as an image of the array, as a table of numbers, or the like.

The total number of spots on the substrate will vary depending on the number of different oligonucleotide probe spots (oligonucleotide probe compositions) one wishes to display on the surface, as well as the number of non probe spots, e.g., control spots, orientation spots, calibrating spots and the like, as may be desired depending on the particular application in which the subject arrays are to be employed. The pattern present on the surface of the array can include at least 2 distinct nucleic acid probe spots, at least about 5 distinct nucleic acid probe spots, at least about 10 distinct nucleic acid spots, at least about 20 nucleic acid spots, or at least about 50 nucleic acid spots.

In some cases, it may be desirable to have each distinct probe spot or probe composition be presented in duplicate, i.e. so that there are two duplicate probe spots displayed on the array for a given target. In some cases, each target represented on the array surface is only represented by a single type of oligonucleotide probe. In other words, all of the oligonucleotide probes on the array for a give target represented thereon have the same sequence. In certain embodiments, the number of spots will range from about 200 to 1200. The number of probe spots present in the array can make up a substantial proportion of the total number of nucleic acid spots on the array, where in many embodiments the number of probe spots is at least about 25%, at least 50%, at least about 80%, or at least about 90% of the total number of nucleic acid spots on the array.

Following preparation of the target nucleic acid from the tissue or cell of interest, the target nucleic acid is then contacted with the array under hybridization conditions, where such conditions can be adjusted, as desired, to provide for an optimum level of specificity in view of the particular assay being performed. Suitable hybridization conditions are well known to those of skill in the art and reviewed in Maniatis et al., supra, and WO 95/21944. Of particular interest in many embodiments is the use of stringent conditions during hybridization, i.e. conditions that are optimal in terms of rate, yield and stability for specific probe-target hybridization and provide for a minimum of non-specific probe/target interaction.

Following hybridization, non-hybridized labeled nucleic acids are removed from the support surface, conveniently by washing, generating a pattern of hybridized nucleic acid on the substrate surface. A variety of wash solutions are known to those of skill in the art and may be used. Methods of detecting hybridization between a probe nucleic acid and a target nucleic acid include scintillation counting, autoradiography, fluorescence measurement, colorimetric measurement, light emission measurement, light scattering, and the like.

Compositions, Kits, and Integrated Systems

The invention provides compositions, kits and integrated systems for practicing the assays described herein using polynucleotides and polypeptides of the invention, antibodies specific for polypeptides or polynucleotides of the invention, etc.

The invention provides assay compositions for use in solid phase assays; such compositions can include, for example, one or more polynucleotides or polypeptides of the invention immobilized on a solid support, and a labeling reagent. In each case, the assay compositions can also include additional reagents that are desirable for hybridization. Modulators of expression or activity of polynucleotides or polypeptides of the invention can also be included in the assay compositions.

The invention also provides kits for carrying out the diagnostic assays of the invention. The kits typically include a probe that comprises an antibody or nucleic acid sequence that specifically binds to polypeptides or polynucleotides of the invention, and a label for detecting the presence of the probe. The kits may include several antibodies specific for, or polynucleotide sequences encoding, the polypeptides of the invention.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical images.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g., by fluorescent or dark field microscopic techniques.

In another aspect, a kit is provided to asses CSNK2A1P status in the cells of a patient. Such a kit will comprise a reagent for detecting either the DNA encoding CSNK2A1P (e.g., one or both of wildtype CSNK2A1P and CSNK2A1P I133T), the mRNA encoding CSNK2A1P the CSNK2A1P polypeptide (e.g., the wild type CSNK2A1P, a polymorphic variant or mutant CSNK2A1P, such as the I133T variant, and the like), or any combination thereof. The reagent will comprise one or more molecules capable of specifically binding a nucleic acid sequence (DNA or RNA) encoding an CSNK2A1P polypeptide. The reagents (e.g., probes, primers, etc.) may be designed to provide for detection the wild-type CSNK2A1P and a polymorphic or mutant variant CSNK2A1P protein, such as the I133T variant. The kit may further comprise anti-CSNK2A1P antibodies or anti-CSNK2A1P variant, such as the I133T variant, antibodies for detection of the polypeptides.

In one example, the kit may comprise one or more nucleic acid reagents for the detection of either DNA encoding CSNK2A1P, mRNA encoding CSNK2A1P or both. The one or more nucleic acid reagents may be used for hybridization or amplification with the DNA and/or mRNA encoding CSNK2A1P. The kit may comprise one or more pairs of primers for amplifying the DNA and/or mRNA encoding CSNK2A1P. The kit may further comprise samples of total mRNA derived from tissue of various physiological states, such as normal tissue or cancerous tissue, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting the DNA and/or mRNA encoding CSNK2A1P in cancer cells in a biological sample comprising oligonucleotide probes effective to bind with high affinity to DNA and/or mRNA encoding CSNK2A1P in vitro or in situ and containers for each of these probes.

In a further embodiment, the invention encompasses a kit for use in determining the level of CSNK2A1P expression in a biological sample comprising one or more agents, such as, for example, one or more antibodies, specific for one or more CSNK2A1P polypeptides. In one particular embodiment, the kit will comprise one or more agents and one or more nucleic acid markers wherein the agents and nucleic acid markers are modified in a fashion appropriate for carrying out immuno-polymerase chain reaction assays.

Probes and primers for inclusion in a subject kit include those useful in various amplification and/or detection systems. Exemplary amplification and/or detection systems include SUNRISE primer-based systems, Molecular Beacons, the TAQMAN system, an AMPLIFLUOR hairpin primer-based system, a Scorpions technology (e.g., bi-functional molecules containing a PCR primer element covalently linked to a probe element), and a Light Upon Extension or LUXT™-based system. Further exemplary detection systems include those based on a melt-curve analysis, and using intercalating dyes such as the fluorescent dye SYBR Green. Where desired, the probes and/or primers can be designed to provide for amplification of one or both of wildtype CSNK2A1P and CSNK2A1P I133T nucleic acid The kits may optionally comprise reagent(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods of the invention, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly (T) or random primers linked to a promoter reactive with the RNA polymerase). Instructions for the use of mathematical algorithms to assess patient prognosis can also be included in a subject kit.

Methods For Screening Candidate Agents

In another aspect, the present disclosure provides methods for identifying candidate agents (e.g., small organic or inorganic molecules) that can be used to treat the diseases and conditions described herein. Candidate agents that are found to decrease wild type or mutant CSNK2A1P activity can be used to treat conditions characterized by increased CSNK2A1P activity (e.g., cancer).

In one example of a screening method of the present disclosure, a mammal (e.g., a mouse, rat, guinea pig, hamster, rodent, and the like) having a wild-type CSNK2A1P gene is contacted with a candidate compound, and the effect of the compound on the phenotype of the animal is monitored relative to an untreated, identically mutant control. In certain embodiments, the provided methods comprise screening candidate molecules by administering them to a mammal overexpressing wild-type CSNK2A1P or a variant thereof, such as an I133T polymorphic variant.

Accordingly, the present disclosure also provides transgenic animals. In certain embodiments, the transgenic animals provided herein express wild-type CSNK2A1P or a variant thereof, such as an I133T polymorphic variant. The transgenic animals provided herein are generally useful as models of CSNK2A1P-associated cancers. As such the transgenic animals find use in the screening of compounds for the treatment of CSNK2A1P-associated cancers.

In addition to animal models, screening assays can be carried out using in vitro or cell culture-based systems, including recombinant cells that express CSNK2A1P genes, or mutants thereof. Any number of methods can be used for carrying out such screening assays, including high throughput techniques. According to one approach, candidate agents are added at varying concentrations to the culture medium of cells (e.g., stem cells) that may or may not be expressing wild type or mutant CSNK2A1P. Gene expression is then measured by, for example, use of a cDNA microarray, quantitative reverse-transcription polymerase chain reaction (qRT-PCR), or standard Northern blot analysis. The effects of candidate agents can also be measured at the level of polypeptide production in a cell using methods including standard immunological techniques (e.g., ELISA, RIA, flow cytometry, western blotting, and immunoprecipitation) employing an antibody specific for the wild type or mutant CSNK2A1P. The level of gene expression in the presence of the candidate agent is compared to the level measured in a control culture medium lacking the candidate agent. In other examples, reporter constructs can be used to indirectly measure wild type or mutant CSNK2A1P expression. In such methods, the expression of a reporter molecule (e.g., luciferase, green fluorescent protein, or β-galactosidase) is placed under the control of the regulatory region upstream of the CSNK2A1P gene of interest, as described herein. A candidate agent that decreases wild type or mutant CSNK2A1P expression, stability, or activity can be used, for example, to treat a proliferative disorder (e.g., cancer).

Candidate agents can also be screened for those that specifically bind to and modulate wild type or mutant CSNK2A1P activity. The efficacy of such a candidate agent can be dependent upon its ability to interact with wild type or mutant CSNK2A1P or CSNK2A1. Such an interaction can be detected using any of a number of standard techniques and functional assays that measure binding activity. For example, candidate agents that bind to wild type or mutant CSNK2A1P can be identified using chromatography-based techniques, fluorescence polarization or anisotropy techniques, spectrophotometric techniques, and the like. In one example, recombinant mutant CSNK2A1P is purified by standard techniques from cells engineered to express mutant CSNK2A1P and immobilized on a column. A solution of candidate agents is then passed through the column, and a compound specific for mutant CSNK2A1P is identified on the basis of its ability to bind to CSNK2A1P and be immobilized on the column. To isolate the agent, the column is washed to remove non-specifically bound molecules, and the agent of interest is then eluted from the column and collected. Candidate agents that are identified as binding to mutant CSNK2A1P with an affinity constant less than or equal to 10 mM may be considered particularly useful in the present disclosure. In certain embodiments, a candidate molecule identified by the methods of the present invention may bind to CSNK2A1P or a variant thereof with an affinity of about 5 mM, 2 mM, 1 mM, 0.5 mM, 0.1 mM, 50 µM, 25 µM, 10 µM, 5 µM, 2 µM, 1 µM, or less.

In certain embodiments, after the identification of a candidate compound with an in vitro or cell-based screening method, the compound can be tested to identify the effect said compound has on a CSNK2A1P-associated phenotype. For example, a candidate compound can be tested for its impact on cellular proliferation in cell culture or animal-based systems, such as a transgenic animal model.

Potential mutant CSNK2A1P agonists and antagonists can be identified from, e.g., libraries of natural products, synthetic (or semi-synthetic) extracts, and chemical libraries using methods that are well known in the art. Candidate agents to be tested include purified (or substantially purified) molecules or one or more components of a mixture of compounds (e.g., an extract or supernatant obtained from cells; Ausubel et al., Current Protocols in Molecular Biology, Vol. 2, 1994), and such agents further include both naturally occurring or artificially derived chemicals and modifications of existing agents. For example, candidate agents can be polypeptides, synthesized organic or inorganic molecules, naturally occurring organic or inorganic molecules, nucleic acid molecules, and components thereof.

Numerous sources of naturally occurring candidate agents are readily available to those skilled in the art. For example, naturally occurring agents can be found in cell (including plant, fungal, prokaryotic, and animal) extracts, mammalian serum, growth medium in which mammalian cells have been cultured, protein expression libraries, or fermentation broths. In addition, libraries of natural agents in the form of bacterial, fungal, plant, and animal extracts are commercially available from a number of sources, including Biotics (Sussex, UK), Xenova (Slough, UK), Harbor Branch Oceanographic Institute (Ft. Pierce, Fla.), and PharmaMar, U.S.A. (Cambridge, Mass.). Further, libraries of natural agents can be produced, if desired, according to methods that are known in the art, e.g., by standard extraction and fractionation.

Artificially derived candidate agents are also readily available to those skilled in the art. Numerous methods are available for generating random or directed synthesis (e.g., semi-synthesis or total synthesis) of any number of chemical agents, including, for example, saccharide-, lipid-, peptide-, and nucleic acid molecule-based agents. In addition, synthetic agent libraries are commercially available from Brandon Associates (Merrimack, N.H.) and Aldrich Chemicals (Milwaukee, Wis.). Libraries of synthetic agents can also be produced, if desired, according to methods known in the art, e.g., by standard extraction and fractionation. Furthermore, if desired, any library or agent can be readily modified using standard chemical, physical, or biochemical methods. The techniques of modern synthetic chemistry, including combinatorial chemistry, can also be used (reviewed in Schreiber, Bioorganic and Medicinal Chemistry 6:1172-1152, 1998; Schreiber, Science 287:1964-1969, 2000).

When a crude extract is found to have a desired effect, further fractionation of the positive lead extract can be carried out to isolate chemical constituents responsible for the observed effect. Thus, the goal of the extraction, fractionation, and purification process is the careful characterization and identification of a chemical entity within the crude extract having a desired activity. The same assays described herein for the detection of activities in mixtures of agents can be used to purify the active component and to test derivatives of these agents.

Methods of fractionation and purification of such heterogeneous extracts are well known in the art. If desired, agents shown to be useful compounds for treatment can be chemically modified according to methods known in the art.

Definitions

It is to be understood that this invention is not limited to particular methods, kits, and compositions for diagnosing proliferative disorders that are described, as such may, of course, vary. It is also to be understood that the terminology used herein is for the purpose of describing particular embodiments only, and is not intended to be limiting, since the scope of the present invention will be limited only by the appended claims.

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, and in the appended claims, the singular forms "a", "an", and "the" include plural referents unless the context clearly dictates otherwise. Thus, for example, reference to "a polypeptide" includes a plurality of such polypeptides, and reference to "the antibody" includes reference to one or more antibodies and equivalents thereof known to those skilled in the art, and so forth.

As used herein, the terms "Casein kinase II" and "CK2" refer to a serine/threonine protein kinase that phosphorylates acidic proteins such as casein. The kinase exists as a tetramer and is composed of two alpha, or two alpha-prime, and two beta subunits. The alpha subunits contain the catalytic activity while the beta subunits undergo autophosphorylation.

As used herein, the terms "CSNK2A1", "CK2 alpha 1", and "casein kinase 2, alpha 1", which are used interchangeably, refer to the alpha subunit of CK2. In humans the CSNK2A1 gene is found on chromosome 20, with a related transcribed pseudogene, or intronless gene, (referred to herein as "CSNK2A1P") located on chromosome 11. One example of CSNK2A1 is provided herein as a protein that has a polypeptide having an amino acid sequence of, or substantially similar to, SEQ ID NO:2 and is encoded by, for example, a nucleic acid having a sequence of SEQ ID NO: 1.

The cDNA ORF sequence of homo sapiens casein kinase 2, alpha 1 polypeptide (CSNK2A1) ACCESSION: NM_177559 REGION: 394..1569 VERSION: NM_177559.2 GI:47419901 or ACCESSION NM_001895 REGION: 277..1452 VERSION: NM_001895.3 GI:47419902

```
                                            (SEQ ID NO: 1)
ATGTCGGGAC CCGTGCCAAG CAGGGCCAGA GTTTACACAG

ATGTTAATAC ACACAGACCTCGAGAATACT GGGATTACGA

GTCACATGTG GTGGAATGGG GAAATCAAGA

TGACTACCAGCTGGTTCGAA AATTAGGCCG AGGTAAATAC

AGTGAAGTAT TTGAAGCCAT CAACATCACAAATAATGAAA

AAGTTGTTGT TAAAATTCTC AAGCCAGTAA AAAAGAAGAA

AATTAAGCGTGAAATAAAGA TTTTGGAGAA TTTGAGAGGA

GGTCCCAACA TCATCACACT GGCAGACATTGTAAAAGACC

CTGTGTCACG AACCCCCGCC TTGGTTTTTG AACACGTAAA

CAACACAGACTTCAAGCAAT TGTACCAGAC GTTAACAGAC

TATGATATTC GATTTTACAT GTATGAGATTCTGAAGGCCC

TGGATTATTG TCACAGCATG GGAATTATGC ACAGAGATGT

CAAGCCCCATAATGTCATGA TTGATCATGA GCACAGAAAG

CTACGACTAA TAGACTGGGG TTTGGCTGAGTTTTATCATC

CTGGCCAAGA ATATAATGTC CGAGTTGCTT CCCGATACTT

CAAAGGTCCTGAGCTACTTG TAGACTATCA GATGTACGAT

TATAGTTTGG ATATGTGGAG TTTGGGTTGTATGCTGGCAA
```

```
GTATGATCTT TCGGAAGGAG CCATTTTTCC ATGGACATGA

CAATTATGATCAGTTGGTGA GGATAGCCAA GGTTCTGGGG

ACAGAAGATT TATATGACTA TATTGACAAATACAACATTG

AATTAGATCC ACGTTTCAAT GATATCTTGG GCAGACACTC

TCGAAAGCGATGGGAACGCT TTGTCCACAG TGAAAATCAG

CACCTTGTCA GCCCTGAGGC CTTGGATTTCCTGGACAAAC

TGCTGCGATA TGACCACCAG TCACGGCTTA CTGCAAGAGA

GGCAATGGAGCACCCCTATT TCTACACTGT TGTGAAGGAC

CAGGCTCGAA TGGGTTCATC TAGCATGCCAGGGGGCAGTA

CGCCCGTCAG CAGCGCCAAT ATGATGTCAG GGATTTCTTC

AGTGCCAACCCCTTCACCCC TTGGACCTCT GGCAGCTCA

CCAGTGATTG CTGCTGCCAA CCCCCTTGGGATGCCTGTTC

CAGCTGCCGC TGGCGCTCAG CAGTAA
```

Amino acid sequence for CSNK2A1> P68400|CSK21_HUMAN Casein kinase II subunit alpha—*Homo sapiens* (Human); NP_001886.

```
                                            (SEQ ID NO: 2)
MSGPVPSRARVYTDVNTHRPREYWDYESHVVEWGNQDDYQLVRKLGRG

KYSEVFEAINITNNEKVVVKILKPVKKKKIKREIKILENLRGGPNIIT

LADIVKDPVSRTPALVFEHVNNTDFKQLYQTLTDYDIRFYMYEILKAL
```

```
DYCHSMGIMHRDVKPHNVMIDHEHRKLRLIDWGLAEFYHPGQEYNVRV

ASRYFKGPELLVDYQMYDYSLDMWSLGCMLASMIFRKEPFFHGHDNYD

QLVRIAKVLGTEDLYDYIDKYNIELDPRFNDILGRHSRKRWERFVHSE

NQHLVSPEALDFLDKLLRYDHQSRLTAREAMEHPYFYTVVKDQARMGS

SSMPGGSTPVSSANMMSGISSVPTPSPLGPLAGSPVIAAANPLGMPVP

AAAGAQQ
```

As used herein, the terms "CSNK2A1P," "CK2 alpha 1 pseudogene," or "CK2 alpha 1 intronless gene" are used interchangeably to refer to a pseudogene of CSNK2A1, which in humans is found at chromosome 11. Unless specifically noted otherwise, these terms encompass the wild-type and polymorphic variants of CSNK2A1P. An example of CSNK2A1P is provided herein as a protein that has a polypeptide having an amino acid sequence of, or substantially similar to, SEQ ID NO:4 and is encoded, for example, by a nucleic acid having a sequence of SEQ ID NO: 3. A second example of a CSNK2A1P is a CSNK2A1P polymorphic 1388T variant polypeptide having an amino acid sequence of SEQ ID NO:6 and encoded by a nucleic acid having a sequence of SEQ ID NO: 5.

The DNA and cDNA ORF sequence of the wild-type CSNK2A1P intronless gene. Nucleotide differences as compared to CSNK2A1 are in underlined letters, and one nucleotide difference with a polymorphic CSNK2A1P variant is shown in a bold, italicized, and underlined letter.

```
                                            (SEQ ID NO: 3)
ATGTCGGGAC CCGTGCCAAG CAGGGCCAGA GTTTACACAG ATGTTAATAC

ACACAGACCTCGAGAATACT GGGATTACGA GTCACATGTG GTGGAATGGG

GAAATCAAGA TGACTACCAGCTGGTTCGAA AATTAGGCCG AGGTAAATAC

AGTGAAGTAT TTGAAGCCAT CAACATCACAAATAATGAAA AAGTTGTTGT TAAAATTCTC

AAGCCAGTAA AAAAGAAGAA AATTAAGCGTGAAATAAAGA TTTTGGAGAA

TTTGAGAGGA GGTCCCAACA TCATCACACT GGCAGACATTGTAAAAGACC

CTGTGTCACG AACCCCCGCC TTGGTTTTTG AACACGTAAA CAACACAGACTTCAAGCAAT

TGTACCAGAC GTTCACAGAC TATGATATTC GATTTTACAT GTATGAGATTCTGAAGGCCC

TGGATTATTG TCACAGCATG GGAATTATGC ACAGAGATGT CAAGCCCCATAATGTCATGA

TTGATCATGA GCACAGAAAG CTACGACTAA TAGACTGGGG TTTGGCTGAGTTTTATCATC

CTGGCCAAGA ATATAATGTC CGAGTTGCTT CCCGATACTT CAAAGGTCCTGAGCTACTTG

TAGACTATCA GATGTACGAT TATAGTTTGG ATATGTGGAG TTTGGGTTGTATGCTGGCAA

GTATGATCTT TCGGAAGGAG CCATTTTTCC ATGGACATGA CAATTATGATCAGTTGGTGA

GGATAGCCAA GGTTCTGGGG ACAGAAGATT TATATGGCTA

TATTGACAAATACAACATTG AATTAGATCC ACGTTTCAAT GATATCTTGG GCAGACACTC

TCGAAAGCGATGGGAACGCT TTGTCCACCG TGAAAATCAG CACCTTGTCA

GCCCTGAGGC CTTGGATTTCCTGGACAAAC TGCTGCGATA TGACCACCAG TCACGGCTTA

CTGCAAGAGA GGCCATGGAGCACCCCTATT TCTACACTGT TGTGAAGGAC

CAGGCTCGAA TGGGTTCATC TAGCATGCCAGGGGGCAGTA CACCCGTCAG
```

```
CAGCGCCAAT GTGATGTCAG GGATTTCTTC AGTGCCAACCCCTTCACCCC TTGGACCTCT

GGCAGGCTCA CCAGTGATTG CTGCTGCCAA CCCCCTTGGGATGCCTGTTC CAGCTGCCGC

TGGCGCTCAG CAGTAA
```

Amino acid sequence for wild-type CSNK2A1P. Amino acid differences as compared to CSNK2A1 are underlined, and one amino acid difference with a polymorphic CSNK2A1P variant is shown in a bold, italicized, and underlined letter.

The DNA and cDNA ORF sequence of a polymorphism (T398C) CSNK2A1P intronless gene. Nucleotide differences as compared to CSNK2A1 are in underlined letters, and one nucleotide difference with a polymorphic CSNK2A1P is shown in a bold, italicized, and underlined letter.

(SEQ ID NO: 5)
```
   1 ATGTCGGGAC CCGTGCCAAG CAGGGCCAGA GTTTACACAG ATGTTAATAC ACACAGACCT

61 CGAGAATACT GGGATTACGA GTCACATGTG GTGGAATGGG GAAATCAAGA TGACTACCAG

121 CTGGTTCGAA AATTAGGCCG AGGTAAATAC AGTGAAGTAT TTGAAGCCAT CAACATCACA

181 AATAATGAAA AAGTTGTTGT TAAAATTCTC AAGCCAGTAA AAAAGAAGAA AATTAAGCGT

241 GAAATAAAGA TTTTGGAGAA TTTGAGAGGA GGTCCCAACA TCATCACACT GGCAGACATT

301 GTAAAAGACC CTGTGTCACG AACCCCCGCC TTGGTTTTTG AACACGTAAA CAACACAGAC

361 TTCAAGCAAT TGTACCAGAC GTTCACAGAC TATGATACTC GATTTTACAT GTATGAGATT

421 CTGAAGGCCC TGGATTATTG TCACAGCATG GGAATTATGC ACAGAGATGT CAAGCCCCAT

481 AATGTCATGA TTGATCATGA GCACAGAAAG CTACGACTAA TAGACTGGGG TTTGGCTGAG

541 TTTTATCATC CTGGCCAAGA ATATAATGTC CGAGTTGCTT CCCGATACTT CAAAGGTCCT

601 GAGCTACTTG TAGACTATCA GATGTACGAT TATAGTTTGG ATATGTGGAG TTTGGGTTGT

661 ATGCTGGCAA GTATGATCTT TCGGAAGGAG CCATTTTTCC ATGGACATGA CAATTATGAT

721 CAGTTGGTGA GGATAGCCAA GGTTCTGGGG ACAGAAGATT TATATGGCTA TATTGACAAA

781 TACAACATTG AATTAGATCC ACGTTTCAAT GATATCTTGG GCAGACACTC TCGAAAGCGA

841 TGGGAACGCT TTGTCCACCG TGAAAATCAG CACCTTGTCA GCCCTGAGGC CTTGGATTTC

901 CTGGACAAAC TGCTGCGATA TGACCACCAG TCACGGCTTA CTGCAAGAGA GGCCATGGAG

961 CACCCCTATT TCTACACTGT TGTGAAGGAC CAGGCTCGAA TGGGTTCATC TAGCATGCCA

1021 GGGGGCAGTA CACCCGTCAG CAGCGCCAAT GTGATGTCAG GGATTTCTTC AGTGCCAACC

1081 CCTTCACCCC TTGGACCTCT GGCAGGCTCA CCAGTGATTG CTGCTGCCAA CCCCCTTGGG

1141 ATGCCTGTTC AGCTGCCGC TGGCGCTCAG CAGTAA
```

(SEQ ID NO: 4)
MSGPVPSRARVYTDVNTHRPREYWDYESHVVEWGNQDDYQLVRKLGKG
KYSEVFEAINIT

NNEKVVVKILKPVKKKKIKREIKILENLRGGPNIITLADIVKDPVSRT
PALVFEHVNNTD

FKQLYQTFTDYDIRFYMYEILKALDYCHSMGIMHRDVKPHNVMIDHE
HRKLRLIDWGLAE

FYHPGQEYNVRVASRYFKGPELLVDYQMYDYSLDMWSLGCMLASMIFR
KEPFFHGRDNYD

QLVRIAKVLGTEDLYGYIDKYNIELDPRFNDILGRHSRKRWERFVHRE
NQHLVSPEALDF

LDKLLRYDHQSRLTAREAMEHPYFYTVVKDQARMGSSSMPGGSTPVSS
ANVMSGISSVPT

PSPLGPLAGSPVIAAANPLGMPVPAAAGAQQ

Amino acid sequence for CSNK2A1P polymorphism (I133T). Amino acid differences as compared to CSNK2A1 are underlined, and one amino acid difference with a polymorphic CSNK2A1P variant is shown in a bold, italicized, and underlined letter.

(SEQ ID NO: 6)
MSGPVPSRARVYTDVNTHRPREYWDYESHVVEWGNQDDYQLVRKLGRG
KYSEVFEAINIT

NNEKVVVKILKPVKKKKIKREIKILENLRGGPNIITLADIVKDPVSRT
PALVFEHVNNTD

FKQLYQTFTDYDTRFYMYEILKALDYCHSMGIMHRDVKPHNVMIDHE
HRKLRLIDWGLAE

FYHPGQEYNVRVASRYFKGPELLVDYQMYDYSLDMWSLGCMLASMIFR
KEPFFHGRDNYD

-continued

QLVRIAKVLGTEDLYGYIDKYNIELDPRFNDILGRHSRKRWERFVHRE
NQHLVSPEALDF

LDKLLRYDHQSRLTAREAMEHPYFYTVVKDQARMGSSSMPGGSTPVSS
ANVMSGISSVPT

PSPLGPLAGSPVIAAANPLGMPVPAAAGAQQ

As used herein, the terms "CSNK2A1" and "CSNK2A1P" encompass CSNK2A1 and CSNK2A1P polypeptides, respectively, having additional amino acids, e.g. a non-native amino terminal methionine (particularly where the naturally-occurring protein has no native N-terminal methionine), and fusion proteins, as well as CSNK2A1 and CSNK2A1P polypeptides, respectively, that have one or more amino acid modifications (e.g., substitutions, insertions, deletions). For example, where the polypeptide has a native N-terminal methionine, such may be deleted and/or substituted with another amino acid). Further, one or more C-terminal amino acids can be deleted and/or substituted with a C-terminal detectable tag. Examples of fusion proteins include CSNK2A1 and/or CSNK2A1P having an N- or C-terminal-linked glutathione-S-transferase (GST), hemagglutinin (HA)-tag, Flag tag, fluorescent protein moiety such as a GFP, RFP, YFP, or other known moiety, and any other fusion with a known polypeptide. The terms "CSNK2A1" and "CSNK2A1P", as used herein, can also encompass nucleic acid molecules, such as a genomic DNA, cDNA, or RNA (e.g., mRNA) molecule, that encode a CSNK2A1 or CSNK2A1P protein, respectively, or fragments thereof.

As used herein, the term "CSNK2A1P status" refers to the status of CSNK2A1P activity in a cell or extract, for example in a tumor cell or extract thereof, which can be assessed by one or more of an expression level of a CSNK2A1P RNA transcript or its expression product (and thus encompasses CSNK2A1P polypeptides levels), CSNK2A1P gene copy number, the presence or absence of a CSNK2A1P I133T polymorphism, the level of CSNK2A1P activity, and the like.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The terms encompass any chain of two or more (e.g., 10, 20, 30, 40, 50, 60, 70, 80, 90, 100, 150, 200, 250, 300, 350, 391, or more) amino acids, regardless of any post-translational modification (e.g., glycosylation or phosphorylation), constituting all or part of a naturally or non-naturally occurring polypeptide, fragment, or peptide. A "protein" can be made up of one or more polypeptides.

As used herein, the term "post-translational modification" refers to any change to an amino acid, polypeptide, or polypeptide fragment made during or after synthesis or translation. Post-translational modifications can be produced naturally, such as during synthesis within a cell or generated artificially, such as by recombinant or chemical means. Non-limiting examples of post-translational modifications include, phosphorylation, acetylation, methylation, biotinylation, formylation, glycosylation, lipoylation, pegylation, ubiquitination, sumoylation, citrullination, deamidation, and the like.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, □-carboxyglutamate, and O-phosphoserine. Amino acid analogs refers to compounds that have the same basic chemical structure as a naturally occurring amino acid, i.e., an □carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, or about 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST or the like). Such sequences are then said to be "substantially identical" or "substantially similar." This definition also refers to, or may be applied to, the compliment of a test sequence. The definition also includes sequences that have deletions and/or additions, as well as those that have substitutions. As described below, algorithms can account for gaps and the like. Generally, identity exists over a region that is at least about 25 amino acids or nucleotides in length, or more over a region that is about 50-100 amino acids or nucleotides in length. In certain embodiments, identity may exist over a region of about 25, 50, 75, 100, 125, 150, 175, 200, 225, 250, 275, 300, 325, 350, 375, 400, 450, 500, 600, 700, 800, 900, 1000, or more amino acids or nucleotides in length. The biomarkers described herein can be detected with probes that have, e.g., more than 70% identity over a specified region, or more than 80% identity, or more than 90% identity, or more than 95% identity to the reference sequence provided by the accession number, up to 100% identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from about 20 to 1000, or from about 50 to 500, or from about 100 to 300, or from about 150 to about 250 in which a sequence may be compared to a reference sequence of the same number of contiguous positions after the two sequences are optimally aligned. Methods of alignment of sequences for comparison are well-known in the art. Alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

One example of algorithms that are suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value;

the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

In certain embodiments, the sequence of a nucleic acid molecule or polypeptide is said to be "substantially identical" to that of a reference molecule if it exhibits, over its entire length, at least about 51%, e.g., at least 55%, 60%, 65%, 75%, 85%, 90%, or 95% (e.g., at least 91%, 92%, 93%, 94%, 95%, 96%, 97%, 98%, or 99%) identity to the sequence of the reference molecule. For nucleic acid molecules, the length of comparison sequences may be, for example, at least about 10, 20, 30, 40, 50, 60, 70, 80, 90, or 100, 200, 300, 400, 500, 600, 700, 800, 900, 1000, 1176 or more nucleotides. For polypeptides, the length of comparison sequences may be, for example, at least about 10, 20, 30, 40, 50, 60, 70, 80, 90, 100, 150, 200, 250, 300, 350, 391 amino acids or more. Of course, the length of comparison can be any length, up to and including full length.

A nucleic acid molecule or polypeptide of the present disclosure can be "analyzed" or subjected to "analysis" if a test procedure is performed on it that allows the determination of its activity or its status as a wild type or mutated version. For example, one can analyze the CSNK2A1P genes of an animal (e.g., a human) by amplifying genomic DNA of the animal using the polymerase chain reaction, and then determining whether the amplified DNA contains a mutation, for example, the I133T mutation, by, e.g., nucleotide sequence or restriction fragment analysis.

As used herein, the term "activity" refers to the expression level, sequence, abundance, concentration, stability, enzymatic activity, or other biologically relevant property of a molecule, such as binding activity to a particular substrate or reagent. The term "activity" can be used in reference to, for example, CSNK2A1P polypeptides or polynucleotides or other polypeptides and polynucleotides provided herein.

A "label" or a "detectable moiety" is a composition detectable by spectroscopic, photochemical, biochemical, biophysical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide. Other non-limiting examples of labels include, radioactive isotopes, fluorescers (fluorophores), chemiluminescers, chromophores, enzymes, enzyme substrates, enzyme cofactors, enzyme inhibitors, chromophores, dyes, metal ions, metal sols, ligands (e.g., biotin, avidin, strepavidin or haptens), intercalating dyes and the like.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62C is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

As used herein, "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). In certain embodiments, an antibody as provided herein may include a minibody, a diabody, a triabody, an scFv, an scFv-Fc, and the like.

A "minibody" is an engineered antibody construct comprised of the variable heavy (VH) and variable light (VL) chain domains of a native antibody fused to the hinge region and to the CH3 domain of the immunoglobulin molecule. Minibodies are thus small versions of whole antibodies encoded in a single protein chain which retain the antigen binding region, and the CH3 domain which to permit assembly into a bivalent molecule and the antibody hinge to accommodate dimerization by disulfide linkages. In contrast, native antibodies are comprised of four chains, two heavy and two light. The size, valency and affinity of the minibody is particularly suited for in vivo targeting. Expression in bacterial or mammalian cells is simplified because minibodies can be produced as single amino acid chains (see, U.S. Pat. No. 5,837,821) which is incorporated by reference herein in its entirety and particularly with reference to minibodies, their structure, ways of making them, and their suitable pharmaceutical formulations.

A 'diabody" comprises a first polypeptide chain which comprises a heavy (VH) chain variable domain connected to a light chain variable domain (VL) on the first polypeptide chain (VH-VL) connected by a peptide linker that is too short to allow pairing between the two domains on the first polypeptide chain and a second polypeptide chain comprising a light chain variable domain (VL) linked to a heavy chain variable domain VH on the second polypeptide chain (VL-VH) connected by a peptide linker that is too short to allow pairing between the two domains on the second polypeptide chain. The short linkages force chain pairing between the complementary domains of the first and the second polypeptide chains and promotes the assembly of a dimeric molecule with two functional antigen binding sites.

For preparation of suitable antibodies or constructs of the invention and for use according to the invention, e.g., recombinant, monoclonal, or polyclonal antibodies, many techniques known in the art can be used (see, U.S. Patent Application Publication No. 20070196274 and U.S. Patent Application Publication No. 20050163782, which are each incorporated by reference in their entirities, particularly with respect to minibody and diabody design) (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

The antibodies of the invention include derivatives that are modified, i.e., by the covalent attachment of any type of molecule to the antibody. For example, the antibody derivatives include, without limitation, antibodies that have been modified by glycosylation, acetylation, pegylation, phosphorylation, amidation, derivatization by known protecting/blocking groups, proteolytic cleavage, linkage to a cellular ligand or other protein, and the like. Any of numerous chemical modifications may be carried out by known techniques, including, but not limited to specific chemical cleavage, acetylation, formylation, metabolic synthesis of tunicamycin, etc. Additionally, the derivative may contain one or more non-natural amino acids.

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536

(1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The antibodies of, and for use according to the invention include humanized and/or chimeric monoclonal antibodies.

In some embodiments, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

The phrase "specifically (or selectively) binds" to an antibody or "specifically (or selectively) immunoreactive with," when referring to a protein or peptide or construct according to the disclosure, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires a construct be selected for its specificity for a particular protein. A variety of immunoassay formats may be used to select constructs specifically immunoreactive with CSNK2A1 or CSNK2A1P. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

In one embodiment, an antibody "binds selectively" or "binds specifically" to a polypeptide, peptide, or fragment if it recognizes and binds to the polypeptide of interest (e.g., a CSNK2A1P polypeptide or CSNK2A1P polymorphic polypeptide), but does not substantially recognize and bind to other molecules (e.g., non-CSNK2A1P-related polypeptides). In certain embodiments, the antibodies of the invention can bind to a specific polymorphic variant of CSNK2A1P, for example CSNK2A1P (I133T), but not a different polymorphic variant or the wild type CSNK2A1P. Similarly, a nucleotide probe is said to "bind selectively" or "bind specifically" or "hybridize selectively" or "hybridize specifically" to a polynucleotide, nucleotide, or fragment thereof, if it preferentially hybridizes to one polynucleotide of interest (e.g., a CSNK2A1P polynucleotide or CSNK2A1P polymorphic polynucleotide), but does not substantially recognize and bind to other molecules (e.g., non-CSNK2A1P-related polynucleotides, or other polymorphic variants of CSNK2A1P) in a sample, e.g., a biological sample that includes the polynucleotide.

The term "differentially expressed" or "differentially regulated" refers generally to a protein or nucleic acid that is overexpressed (upregulated) or underexpressed (downregulated) in one biological sample compared to at least one other sample, generally in a biological sample from a subject with cancer or a cancer cell, in comparison to a biological sample from a subject without cancer or a non-cancer cell.

The terms "overexpress", "overexpression", "overexpressed", "up-regulate", or "up-regulated" interchangeably refer to a protein or nucleic acid that is present at a detectably greater level in a biological sample, e.g. biological sample or cancer cell, from a patient with cancer, in comparison to a biological sample from a patient without cancer or non-cancerous cell. The term includes overexpression in a sample from a patient with cancer due to transcription, post transcriptional processing, translation, post-translational processing, cellular localization (e.g, organelle, cytoplasm, nucleus, cell surface), and RNA and protein stability, as compared to a sample from a patient without cancer. Overexpression can be detected using conventional techniques for detecting mRNA (i.e., RT-PCR, PCR, hybridization) or proteins (i.e., ELISA, immunohistochemical techniques, mass spectroscopy, Luminex® xMAP technology). Overexpression can be 10%, 20%, 30%, 40%, 50%, 60%, 70%, 80%, 90% or more in comparison to a sample from a patient without cancer. In certain instances, overexpression is 1-fold, 2-fold, 3-fold, 4-fold 5, 6, 7, 8, 9, 10, or 15-fold or more higher levels of transcription or translation in comparison to a sample from a patient without cancer.

The terms "underexpress," "underexpression", "underexpressed" or "downregulated" interchangeably refer to a protein or nucleic acid, that is present at a detectably lower level in a biological sample, e.g. a biological sample or cancer cell, in comparison to a biological sample from a subject without cancer or a non-cancerous cell. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques, Luminex® xMAP technology). Underexpression can be 10%, 20%, 30%, 40%, 50%, 60%, 70%, 80%, 90% or less in comparison to a sample from a subject without cancer. In certain instances, underexpression is 1-fold, 2-fold, 3-fold, 4-fold or more lower levels of transcription or translation in comparison to a control.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., lung, tongue, colon, prostate, kidney, bladder, lymph node, liver, bone marrow, blood cell, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, e.g., in Kasper et al., *Harrison's Principles of Internal Medicine*, eds., 16$^{th}$ ed., Chapter 70 and throughout Part V (2005).

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal ion concentration, and salt concentration. Primers are generally of a length compatible with their use in synthesis of primer extension products, and can be in the range of between about 8 nucleotides and about 100 nucleotides (nt) in length, such as about 10 nt to about 75 nt, about 15 nt to about 60 nt, about 15 nt to about 40 nt, about 18 nt to about 30 nt, about 20 nt to about 40 nt, about 21 nt to about 50 nt, about 22 nt to about 45 nt, about 25 nt to about 40 nt, and so on, e.g., in the range of between about 18 nt and about 40 nt, between about 20 nt and about 35 nt, between about 21 and about 30 nt in length, inclusive, and any length between the stated ranges. Primers can be in the range of between about 10-50 nucleotides long, such as about 15-45, about 18-40, about 20-30, about 21-25 nt and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

Primers are in many embodiments single-stranded for maximum efficiency in amplification, but may alternatively be double-stranded. If double-stranded, the primer is in many embodiments first treated to separate its strands before being used to prepare extension products. This denaturation step is typically effected by heat, but may alternatively be carried out, for example, by using alkali, followed by neutralization. Thus, a "primer" is complementary to a template, and complexes by hydrogen bonding or hybridization with the template to give a primer/template complex for initiation of synthesis by a polymerase, which is extended by the covalent addition of bases at its 3' end.

As used herein, a "primer pair" refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary or substantially complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with their use in specific detection of all or a portion of a target sequence of a target nucleic acid, and are in many embodiments in the range of between about 8 nt and about 100 nt in length, such as about 8 to about 75 nt, about 10 to about 74 nt, about 12 to about 72 nt, about 15 to about 60 nt, about 15 to about 40 nt, about 18 to about 30 nt, about 20 to about 40 nt, about 21 to about 50 nt, about 22 to about 45 nt, about 25 to about 40 nt in length, and so on, e.g., in the range of between about 18-40 nt, about 20-35 nt, or about 21-30 nt in length, and any length between the stated ranges. In some embodiments, a probe is in the range of between about 10-50 nucleotides long, such as about 15-45, about 18-40, about 20-30, about 21-28, about 22-25 and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

As used herein, the terms "treatment," "treating," and the like, refer to administering an agent, or carrying out a procedure (e.g., radiation, a surgical procedure, etc.), for the purposes of obtaining a effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

"Therapeutic treatment" and "cancer therapies" refers to chemotherapy, hormonal therapy, radiotherapy, immunotherapy, biologic therapy, and the like.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations*

(1999); and *Remington: The Science and Practice of Pharmacy*, 20th Edition, 2003, Gennaro, Ed., Lippincott, Williams & Wilkins).

Compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient.

A "patient" or "subject" for the purposes of the present disclosure includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, and the like.

In other embodiments, the methods of the invention may be practiced together with other cancer therapies, for example, radiation therapy, hormone therapy, surgical therapy, or chemotherapy. Surgical therapies typically involve removal of a tumor or cancerous growth plus some surrounding tissue. This treatment is used commonly when the cancer is thought not to have spread beyond a specific tissue. Radiation therapy is commonly used to treat cancer that is still confined to a particular region, or has spread to nearby tissue. If the disease is more advanced, radiation may be used to reduce the size of the tumor. Hormone therapy is often used for patients whose cancer has spread beyond the tissue of origin or has recurred. These agents may be injected either monthly or longer. Chemotherapy is an option for patients whose cancer has spread outside of the tissue of origin or for whom hormone therapy has failed. It is not expected to destroy all of the cancer cells, but it may slow tumor growth and reduce pain. Two or more drugs are often given together to reduce the likelihood of the cancer cells becoming resistant to chemotherapy.

The combined administrations contemplates co-administration, using separate formulations or a single pharmaceutical formulation, and consecutive administration in either order, wherein preferably there is a time period while both (or all) active agents simultaneously exert their biological activities.

As used herein, the terms "treatment," "treating," and the like, refer to administering an agent, or carrying out a procedure (e.g., radiation, a surgical procedure, etc.), for the purposes of obtaining a effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread" or "metastasis," similarly, occurs when the cells of a tumor disseminate into local or distant tissues and organs; therefore tumor spread encompasses tumor metastasis.

As used herein, the term "diagnosis" refers to the identification of a disease state, such as cancer, a pathological state, a condition, and the like, in a subject. Diagnosis can also include the identification of a particular subtype or stage of a disease or condition, such as cancer. The methods of diagnosis provided by the present invention can be combined with other methods of diagnosis well known in the art. Non-limiting examples of other methods of diagnosis include, detection of previously known disease biomarkers, including protein and nucleic acid biomarkers, radiography, co-axial tomography (CAT) scans, positron emission tomography (PET), radionuclide scanning, and the like.

As used herein, the term "providing a prognosis" refers to providing a prediction of the probable course and outcome of a disease state or condition, for example, a cancer. In certain embodiments, the term "prognosis" is used herein to refer to the prediction of the likelihood of cancer-attributable death or progression, including recurrence, metastatic spread, and drug resistance, of a neoplastic disease, such as lung, colon, skin or esophageal cancer.

As used herein, the phrase "disease-free survival," refers to the lack of such tumor recurrence and/or spread and the fate of a patient after diagnosis and/or treatment, with respect to the effects of the cancer on the life-span of the patient. The phrase "overall survival" refers to the fate of the patient after diagnosis and/or treatment, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis and/or treatment of cancer, wherein the probability is determined according to the methods disclosed herein.

The terms "cancer," "neoplasm," and "tumor" refer to cancers, for example, human cancers, and carcinomas, leukemias, sarcomas, adenocarcinomas, lymphomas, solid and lymphoid cancers, etc. Examples of different types of cancer include, but are not limited to, monocytic leukemia, myelogenous leukemia, acute lymphocytic leukemia, and acute myelocytic leukemia, chronic myelocytic leukemia, promyelocytic leukemia, breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, soft tissue and osteogenic sarcoma, colorectal cancer, liver cancer (i.e., hepatocarcinoma), renal cancer (i.e., renal cell carcinoma), pleural cancer, pancreatic cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma; osteogenic sarcoma, fibrosarcoma, glioma, melanoma, B-cell lymphoma, non-Hodgkin's lymphoma, Burkitt's lymphoma, Small Cell lymphoma, Large Cell lymphoma, and the like.

A "biological sample" encompasses a variety of sample types obtained from an individual. The term encompasses blood and other liquid samples of biological origin, solid or semi-solid samples such as a tissue specimen or tissue cultures, as well as cells derived therefrom and the progeny thereof. "Biological sample" also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells. Samples may include, but are not limited to, amniotic fluid, biopsies, blood, blood cells, bone marrow, cerebrospinal fluid, fecal samples, fine needle biopsy samples, peritoneal fluid, plasma, pleural fluid, saliva, semen, serum, sputum, tears, tissue or tissue homogenates, tissue culture media, urine, and the like. Samples may also be processed, such as sectioning of tissues, fractionation, purification, or cellular organelle separation.

The terms "gene product" and "expression product" are used interchangeably herein in reference to a gene, to refer to the RNA transcription products (transcripts) of the gene, including mRNA and the polypeptide translation products of such RNA transcripts, whether such product is modified post-translationally or not. The terms "gene product" and "expression product" are used interchangeably herein, in reference to an RNA, particularly an mRNA, to refer to the polypeptide translation products of such RNA, whether such product is modified post-translationally or not. A gene product can be, for example, an unspliced RNA, an mRNA, a splice variant mRNA, a polypeptide, a post-translationally modified polypeptide, a splice variant polypeptide, etc.

EXAMPLES

The following examples are put forth so as to provide those of ordinary skill in the art with a complete disclosure and description of how to make and use the present disclosure, and are not intended to limit the scope of what the inventors regard as their present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods

Cell lines, tissue samples, and chemicals: The human cancer and lung fibroblast cell lines used in this study were obtained from American Type Culture Collections (Manassas, Va.). Cells were cultured in RPMI 1640 supplemented with 10% fetal bovine serum, penicillin (100 IU/ml), and streptomycin (100 µg/ml). All cells were cultured at 37° C. in a humid incubator with 5% $CO_2$. The chemical compound, Hematein, was purchased from City Chemicals (CAS No. 15489-90-4, Catalogue No. 265D).

Fluorescence In-Situ Hybridization (FISH) analyses: The FISH probe for CSNK2A1P (RP11-567I13, Ch. 11p15) was purchased from BACPAC Resources (Oakland, Calif.). The chromosome 11 centromere probe labeled with FITC (CEP11) was purchased from Vysis (Des Plains, Ill.). Metaphase slides were prepared using standard protocols from the UCSF Molecular Pathology Core facility. All hybridizations were done by the UCSF Molecular Pathology Core facility. The CSNK2A1P BAC probe was labeled with Texas Red by Nick Translation. Probe Mixture (along with CEP11 probe labeled with FITC) was prepared according standard protocols.

DNA and cDNA sequencing analysis: Genomic DNA or total RNA was isolated from cell lines and tissue samples. The CSNK2A1P gene was PCR amplified using its gene-specific primers. The PCR products were extracted from the agarose gel using an extraction kit (QIAquick Gel Extraction kit; Qiagen) and were subsequently sequenced at MCLab (South San Francisco, Calif.).

Semi-quantitative reverse transcription-PCR(RT-PCR) analysis: Total RNA from cell lines and tissues was isolated using an extraction kit, and DNA was eliminated by on-column treatment with DNase (RNeasy Mini kit; Qiagen, Valencia, Calif.). Semi-quantitative RT-PCR was performed using a kit (SuperScript One-step RT-PCR with Platinum Taq kit; Invitrogen, Carlsbad, Calif.) according to the manufacturer's protocol. One-step RT-PCR was performed using a pair of CSNK2A1P-specific primers (Forward: 5'-AGAAAATTGCTCCCCACTCC-3'(SEQ ID NO:7) Reverse: 5'-GTGCTGCCAGAGAATGACAA-3' (SEQ ID NO:8)). Glyceraldehyde-3-phosphatedehydrogenase (GAPDH) was used as an internal control.

Quantitative reverse transcription-PCR(RT-PCR) analysis: Total RNA from cell lines and tissues was isolated using an extraction kit, and DNA was eliminated by on-column treatment with DNase (RNeasy Mini kit; Qiagen, Valencia, Calif.). First-strand cDNA was synthesized from 3 µg of total RNA templates using the iScript cDNA Synthesis Kit (Bio-Rad, Hercules, Calif.), and the expression levels corresponding to the gene transcript were measured by real-time quantitative PCR using an ABI PRISM 7900 HT Sequence Detection System with an automation accessory (Applied Biosystems, Foster City, Calif.). The CSNK2A1P primer sequences were: Forward 5'-GAAAATTGCTCCCCACTC-CAT-3' (SEQ ID NO:9) and Reverse 5'-GTGGCCGCTCTC-CCTTCT-3' (SEQ ID NO:10). The TaqMan probe sequence was CCGCCGTCTCTCCCTTCT (SEQ ID NO:11). Each 20 µL reaction, performed in triplicate, consisted of TaqMan Universal PCR Master Mix (Applied Biosystems, Foster City, Calif.), the appropriate Taqman Gene Expression Assay (Applied Biosystems, Foster City, Calif.), and 1.8 µL cDNA template corresponding to 120 ng of total RNA per reaction. $C_t$ values were obtained using the Sequence Detection System (SDS) 2.3 software (Applied Biosystems, Foster City, Calif.) and relative gene expression values were calculated as $\Delta\Delta C_t$, which yields the relative expression level of a target gene normalized to that of an endogenous reference gene relative to a calibrator sample (the reference for all samples). The calibrator sample used was cDNA synthesized from normal human lung total RNA (Clontech, Mountain View, Calif.). The gene expression values were normalized to that of 18S rRNA.

Cloning of CSNK2A1P wild-type and mutant cDNAs: The full-length cDNA from A549 cells was cloned into a TA cloning vector and then subcloned into a pcDNA3.1 myc-his vector. One wild-type clone and one mutant clone were validated and selected for the subsequent soft agar assay.

Western blot analysis: Western blots were performed as previously described in Uemtsu et al., Cancer Res. 2003 Aug. 1; 63(15):4547-51. Briefly, proteins were separated on 4-15% gradient SDS—polyacrylamide gels and transferred to Immobilon-P membranes (Millipore, Bellerica, Mass.). The proteins were bound with primary antibodies for CK2alpha and β-actin (Sigma Chemical, St. Louis, Mo.). Antigen-antibody complexes were then detected using the ECL blotting analysis system (Amersham Pharmacia Biotech, Piscataway, N.J.).

Soft agar growth assay: A layer of 1.4% (w/v) Low Melting Temperature (LMT) agarose in DMEM was poured and allowed to solidify. For experiments using the pcDNA3.1 vectors expressing wild-type CSNK2A1 and wild-type CSNK2A1P, NIH3T3 cells were transfected with these vectors or an empty vector control 24 hours before seeding in agar. After 3 weeks, excess medium was removed, and 1 mg/ml solution of p-iodonitrotetrazolium violet (Sigma, St Louis, Mo.) was added overnight to stain viable cells. Colonies were photographed and counted after staining.

Cell proliferation assay: Hela, Jurkat, A427, A549, HCT116, WI-38 and CCL-211 cells were plated in 96-well plates at a density of 5000 cells/well. Cells were allowed to attach overnight in growth medium. After 24 hours, cells were treated with Hematein or other compounds (0-100 µM). After incubation for 72 hours, cellular proliferation was measured using the MTS assay (Cell Titer AQuest one solution assay, Promega (Madison, Wis.)) and absorbance was measured at 490 nm Proliferation data were presented as means±SD.

CK2 kinase assays: For the CK2 holoenzyme ELISA, a CK2 kinase inhibitor screening assay was purchased from CycLex Co. Ltd. (Japan). For the catalytic CK2 alpha assay, the Kinase-Glo Plus Luminescent Kinase Assay was purchased from Promega (Madison, Wis.). The SelectScreen CK2 alpha analysis for Hematein was obtained through custom service by Invitrogen (Carlsbad, Calif.).

Transfection with CSNK2A1P siRNA: CSNK2A1P siRNA (Stealth RNAi) was prepared by Invitrogen (Carlsbad, Calif.). The sequence of the siRNA targeting CSNK2A1P was: AAACCUUCCCAUCUCUAAUCUGAGA (SEQ ID NO:12). Transfection was performed using Lipofectamine 2000 (Invitrogen, Carlsbad, Calif.) in accordance with the manufacturer's instructions. Cells were seeded into 6-well plates at $1\times10^4$ cells/well. 24 hours later, cells were transfected with 50 or 100 µM of siRNA according to standard protocol. For Western blot analysis, the cells were incubated for 48 hours, and then total protein was isolated. For the luciferase reporter assay, cells were transfected with 20 or 40 pM of siRNA and the cells were incubated for 24 hours.

Transient Transfection and Luciferase Reporter Assay: For transfection of CSNK2A1P-specific small interfering RNA (siRNA), the siRNA of CSNK2A1P were purchased from Invitrogen (Carlsbad, Calif.). For the TCF reporter assay, the TOP/FOP flash plasmid system was used to determine the transcriptional activity of β-catenin. All transfection experiments were performed using the Lipofectamine 2000 method (Invitrogen, Carlsbad, Calif.) in triplicate in accordance with the manufacturer's instructions. The HCT116, A427 or A549 cells were transfected with 8 µg TOP flash or 8 µg FOP flash plasmid (Upstate Biotechnology, Lake Placid, N.Y.), and the pRL-TK plasmid (Promega, Madison, Wis.) was co-transfected to normalize for transfection efficiency. Cells were treated with Hematein (0-100 µM) 24 hours after transfection. Luciferase activity was assayed 24 hours after treatment by using the Dual-Luciferase reporter assay system (Promega, Madison, Wis.).

SIFT (Sorting Intolerant From Tolerant) uses sequence homology (not structure predictions) to predict whether an amino acid substitution will affect protein function and hence, potentially alter phenotype. SIFT is a sequence homology-based tool that sorts intolerant from tolerant amino acid substitutions and predicts whether an amino acid substitution in a protein will have a phenotypic effect. SIFT is based on the premise that protein evolution is correlated with protein function. Positions important for function should be conserved in an alignment of the protein family, whereas unimportant positions should appear diverse in an alignment. SIFT takes a query sequence and uses multiple alignment information to predict tolerated and deleterious substitutions for every position of the query sequence. SIFT is a multistep procedure that (1) searches for similar sequences, (2) chooses closely related sequences that may share similar function to the query sequence, (3) obtains the alignment of these chosen sequences, and (4) calculates normalized probabilities for all possible substitutions from the alignment. Positions with normalized probabilities less than 0.05 are predicted to be deleterious, those greater than or equal to 0.05 are predicted to be tolerated.

Example 1

Amplification and Over-Expression of CSNK2A1P

Figure 1A:
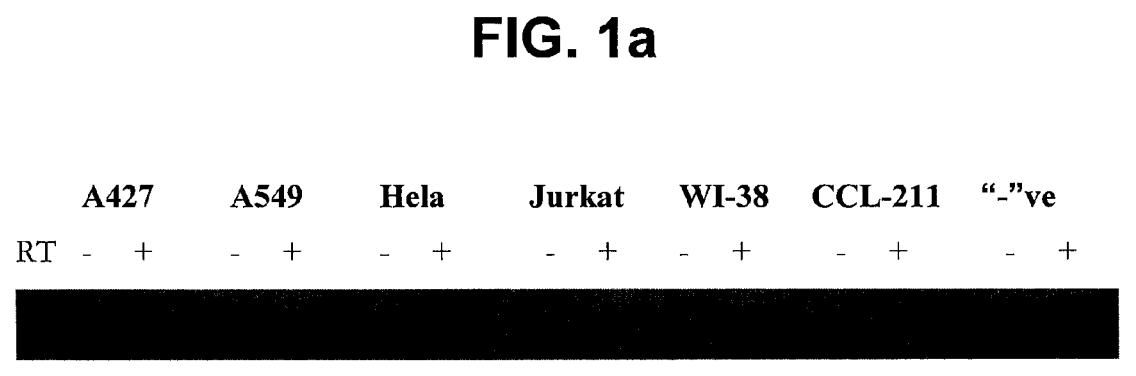

By semi-quantitative RT-PCR using CSNK2A1P-specific primers, the CSNK2A1P mRNA expression level was determined in various cancer cell lines e.g., non-small cell lung cancer cell lines including A427, A549; the cervical cancer cell line Hela; and the T cell leukemia cell line Jurkat. The amplified CSNK2A1P gene was expressed in the cancer cell lines at the mRNA level (FIG. 1a). As can be seen, CSNK2A1P mRNA expression levels are highest in Hela cells.

Figure 1B:
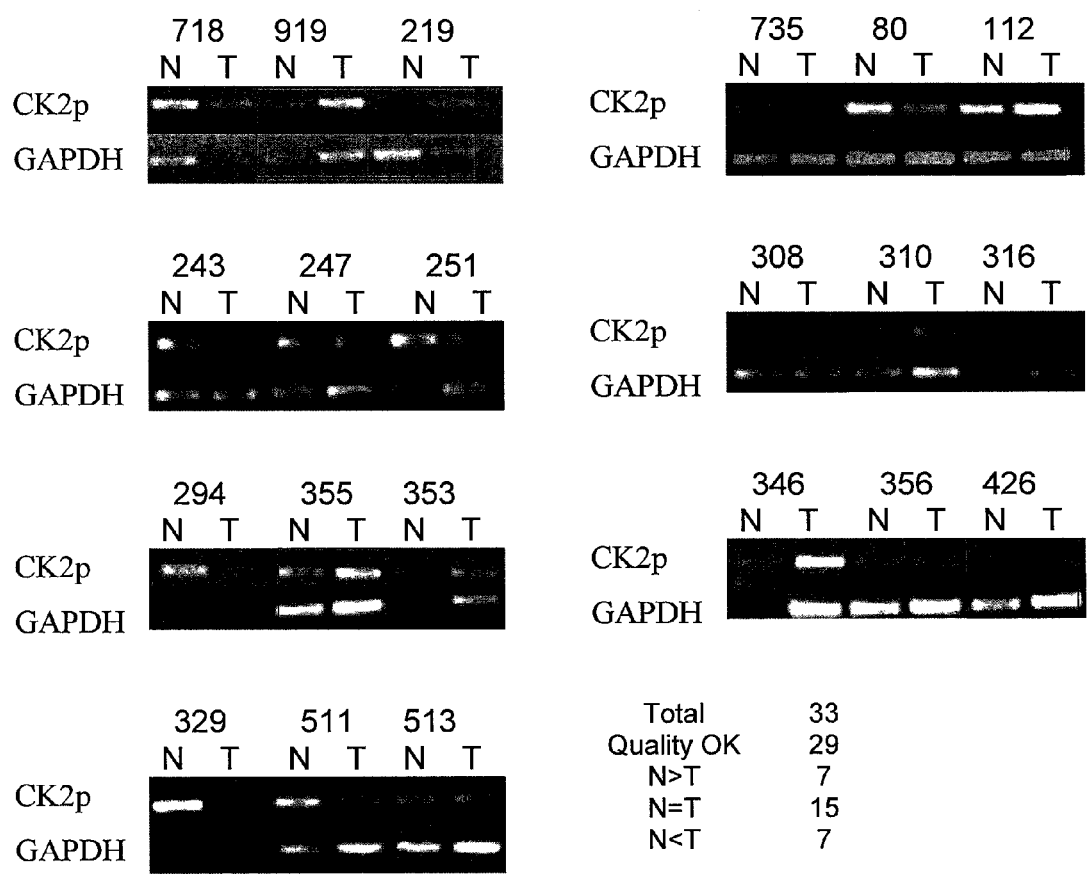
FIG. 1b shows mRNA expression of the CSNK2A1P gene in lung cancer patients' tumor compared to the matched control tissue in the same patients, measured by semi-quantitative RT-PCR.

By semi-quantitative RT-PCR using CSNK2A1P-specific primers, the CSNK2A1P mRNA expression level was determined in lung cancer patients' tumors. Over-expression of CSNK2A1P mRNA was found in six out of 29 (~21%) lung cancer patients' tumor when compared to their matched control tissue (FIG. 1b; red boxes). These data showed that the CSNK2A1P gene was over-expressed at the mRNA level in some lung cancer patients' tumors.

Figure 1C:
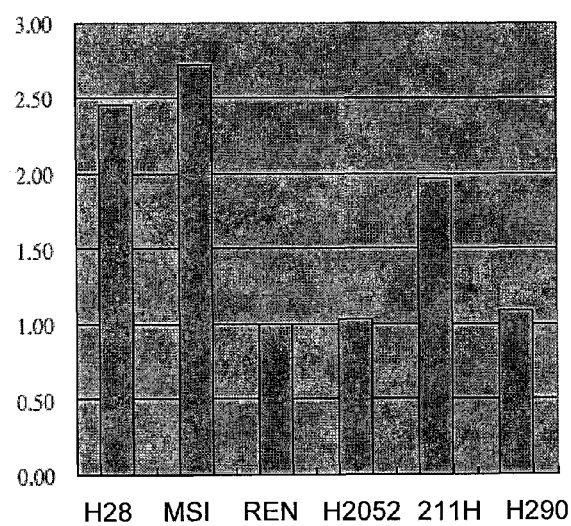
FIG. 1c shows mRNA expression of the CSNK2A1P gene in mesothelioma cell lines, measured by semi-quantitative RT-PCR.
Figure 1D:
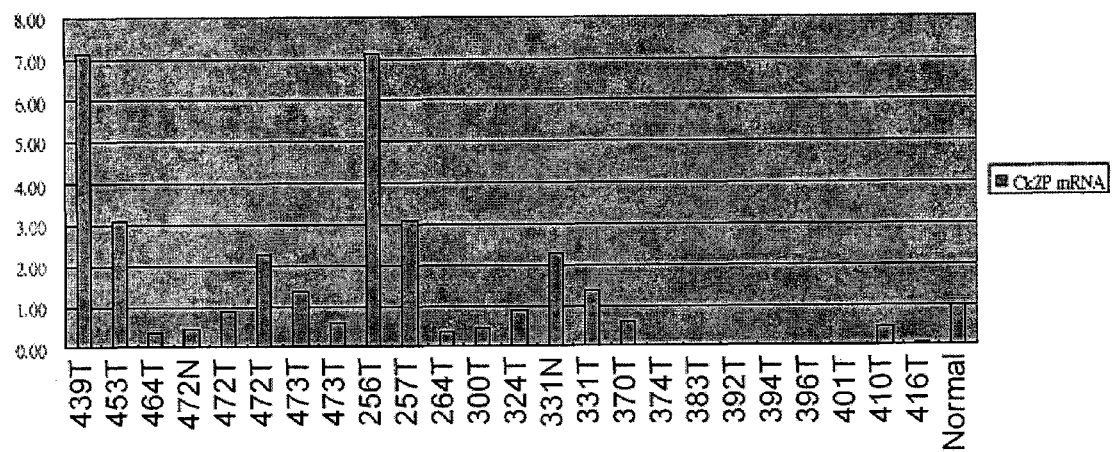
FIG. 1d shows mRNA expression of the CSNK2A1P gene in mesothelioma tumor tissues, measured by semi-quantitative RT-PCR.

By semi-quantitative RT-PCR using CSNK2A1P-specific primers, the CSNK2A1P mRNA expression level was determined in both mesothelioma cell lines (FIG. 1c) and mesothelioma tumor tissues (FIG. 1d). The amplified CSNK2A1P gene was expressed at the mRNA level in both mesothelioma cell lines (FIG. 1c) and mesothelioma tumor tissues.

FISH analysis on the human cancer cell lines showed solid evidence of the amplification of CSNK2A1P located on chromosome 11p15.3. For instance, 5 copies of the CSNK2A1P gene were found in human cervical cancer cell line Hela. Human normal lymphocyte had diploid CSNK2A1P gene.

The CSNK2A1P copy number changes in the human cancer cell lines tested were summarized in Table 1 below Importantly, there was a correlation between the mRNA expression levels and copy numbers of the CSNK2A1P gene in these human cancer cell lines and the mesothelioma cell lines.

TABLE 1

Analysis of CSNK2A1P Gene Copy Numbers in Cell Lines by FISH.

| Cell line | CSNK2A1P copy number |
|---|---|
| Normal lymphocyte | 2 |
| Hela (cervical cancer) | 4-5 |
| Jurkat (leukaemia) | 3-4 |
| A549 (lung cancer) | 3 |
| A427 (lung cancer) | 4 |
| H1299 (lung cancer) | 3 |
| H1650 (lung cancer) | 1 |
| HCT-116 (colon cancer) | 2 |
| MS-1 (mesothelioma) | 3-4 |
| H28 (mesothelioma) | 3 |
| H513 (mesothelioma) | 2 |

There was a correlation between mRNA expression level and the copy number of the CSNK2A1P gene in these human cancer cell lines and tissues.

Example 2

Polymorphic Variant of CSNK2A1P

Figure 2A:
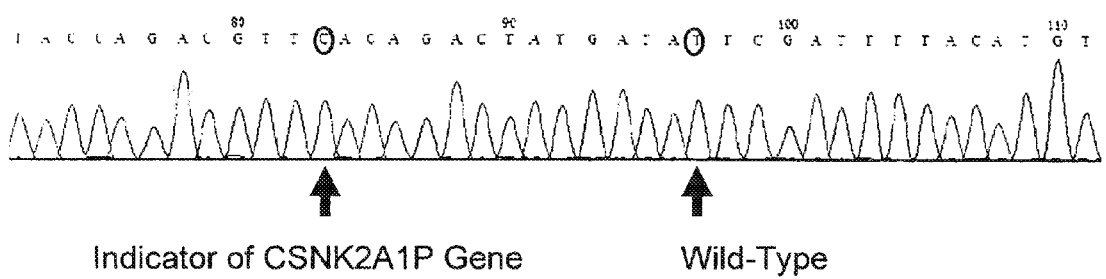
FIG. 2a shows sequencing analysis of wild-type CSNK2A1P gene (nucleotides 373-412 of SEQ ID NO: 3) in Jurkat cells.

In addition to the amplification of the CSNK2A1P gene, a novel polymorphism was found within the kinase domain in several human cancer cell lines. Both Jurkat and Hela cells had the wild-type CSNK2A1P gene. The C above the arrowhead (nucleotide A→C, L128F) on the left is the marker for the CSNK2A1P gene. The T above the arrowhead (nucleotide 398T, I133,) on the right is the indication of the wild-type gene in Jurkat cells (FIG. 2a).

Figure 2B:
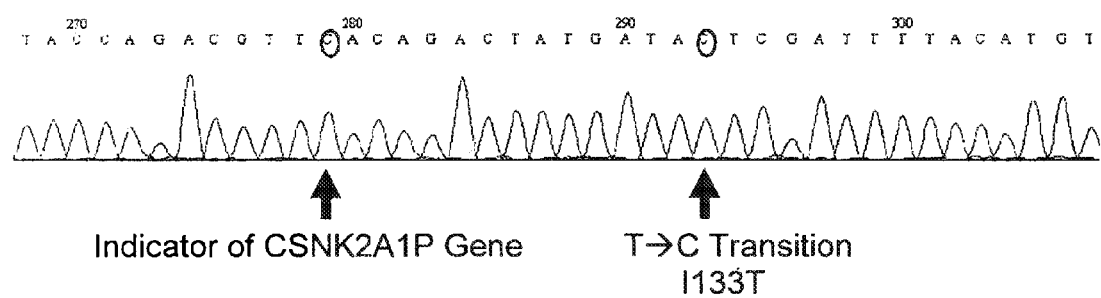
FIG. 2b shows sequencing analysis of CSNK2A1P gene in HCT-116 cells having homozygous CSNK2A1P polymorphic gene (nucleotides 373-412 of SEQ ID NO: 5). A CSNK2A1P Polymorphism of 398 T→C (I133T) was found in HCT-116 cells.

Colon cell line HCT116 had homozygous CSNK2A1P polymorphic gene. The C (384 A→C, L128F) above the arrowhead on the left is the marker for CSNK2A1P gene. The C (398 T→C, I133T) above the arrowhead on the right is the indication of the polymorphic gene, and the clean single peak at that spot showed that it was homozygous (FIG. 2b). The 398T→C caused amino acid change I133T (FIG. 2b). CSNK2A1P polymorphisms found in human cancer cell lines were summarized in Table 2 below.

TABLE 2

CSNK2A1P Polymorphisms Found in Human Cancer Cell Lines

| Cells | 398T→C |
|---|---|
| Hela | − |
| Jurkat | − |
| A549 | + |
| A427 | + |
| H322 | + |
| H358 | + |
| H1650 | + |
| HCT116 | + |
| H460 | − |
| H1299 | + |
| MS-1 | − |
| H28 | − |

Figure 2C:
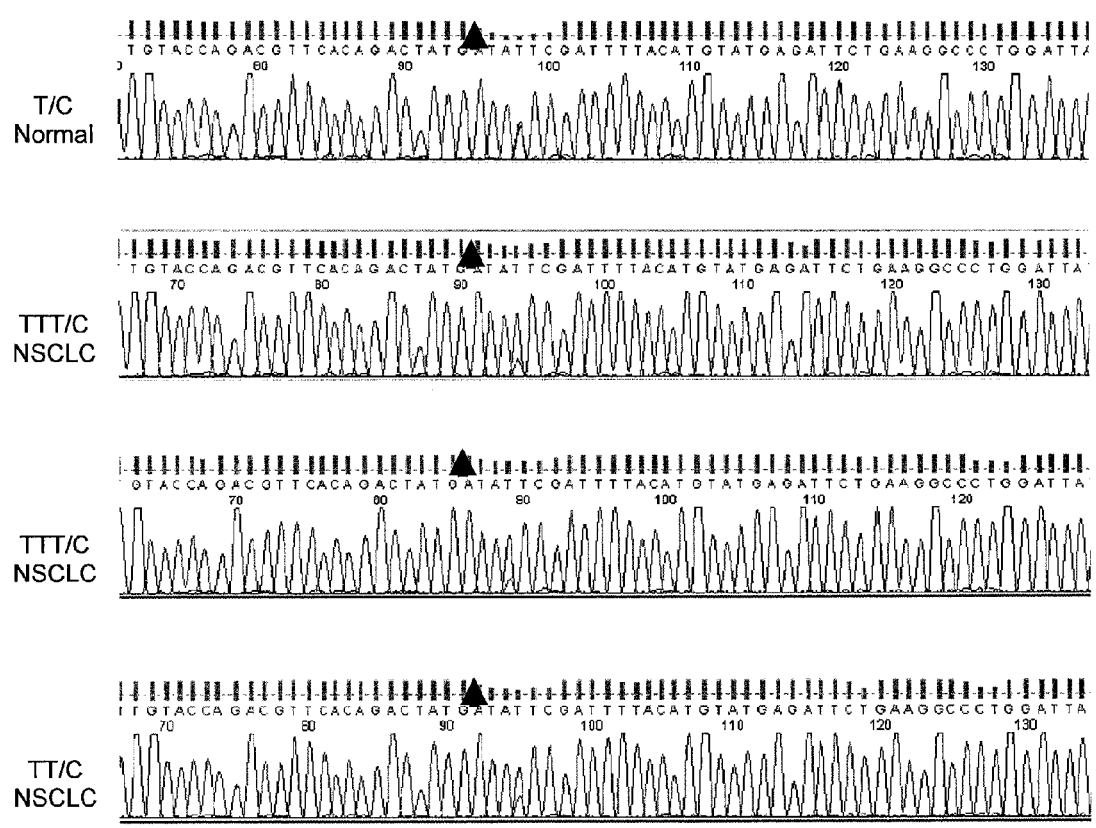
FIG. 2c shows allele-specific amplification of the 398T allele (TTT/C or TT/C) in some non-small cell lung cancer tissue samples(nucleotides 370-437 of SEQ ID NO: 3 and SEQ ID NO: 5 shown in figure).

Allele-specific amplification of the 398T allele (TTT/C or TT/C) was found in some non-small cell lung cancer tissue samples (FIG. 2c). The T above the arrowhead (nucleotide 398T, I133) on the right is the indication of the wild-type gene.

The specific amino acid change of I133T is predicted to affect the protein function using sorting intolerant from tolerant (SIFT) method. In normal individuals, this polymorphism of 398T→C appeared to be evenly distributed as shown in Table 3 below.

TABLE 3

Sequencing Results of 398T→C Mutations in Normal Samples

| T | 12 (25%) |
|---|---|
| C/T or T/C | 24 (50%) |
| C | 12 (25%) |
| Total | 48 |

However, in lung cancer tissues, the 398T allele was selectively amplified as shown in Table 4. (Chi-Square test, p<0.01)

TABLE 4

Sequencing Results of 398T→C Mutations in Tumor Samples

| CC/T | 2 (5%) |
|---|---|
| TT/C or TTT/C | 18 (17.8%) |
| T | 35 (34.6%) |
| C/T or T/C | 36 (35.6%) |
| C | 10 (10%) |
| Total | 101 |

This selective amplification of the 398T allele in lung cancer tissues was compared with that of normal tissues and summarized in Table 5 below. The 398T allele of the CSNK2A1P gene was selectively amplified in lung cancer tissues as compared to normal tissues.

TABLE 5

Selective amplification of 398T allele in lung cancer tissues

| Allele | Normal | Tumor |
|---|---|---|
| TT/C or TTT/C | 0 | 18 |
| T/T | 12 | 35 |
| T/C | 24 | 36 |
| C/C | 12 | 10 |
| CC/T | 0 | 2 |
| Total | 48 | 101 |

This allele-specific amplification suggests that the 398T allele provides growth advantage over the 398C allele.

Example 3

Cloning and Transfection of CSNK2A1 and CSNK2A1P

Figure 3A:
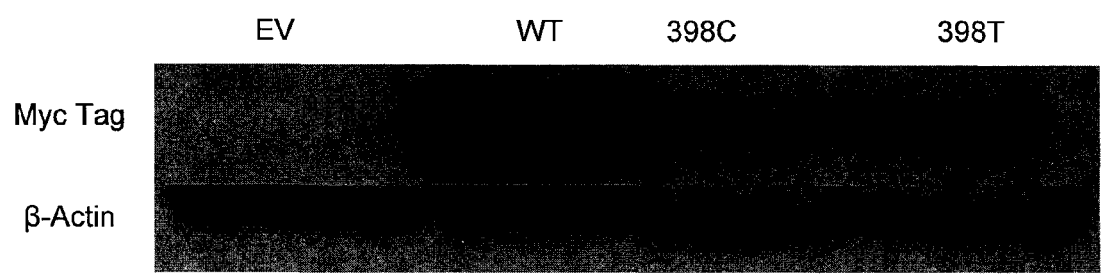
FIG. 3a shows expression of CSNK2A1P protein in 293T cells transiently transfected with CSNK2A1P.
Figure 3B:
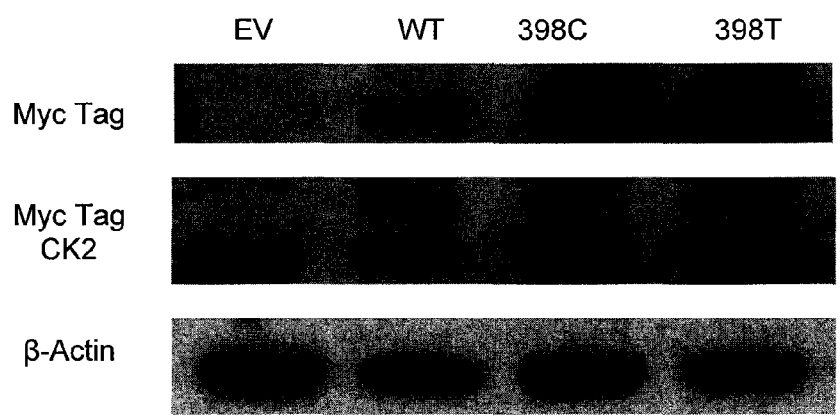
FIG. 3b shows expression of CSNK2A1P protein in NIH3T3 cells transiently transfected with CSNK2A1P.

The CSNK2A1 and CSNK2A1P genes were cloned into pcDNA 3.1 myc-his vetcor. In this study, these vectors were transiently transfected into 293T and NIH3T3 cells and Western blot analysis was used to confirm the protein expression of both alleles of the CSNK2A1P gene (FIG. 3a for 293T cells and FIG. 3b for NIH3T3 cells). These results showed, for the first time, that the CSNK2A1P gene is competent for transcription and translation of the CSNK2A1P protein.

Example 4

Colony Formation Assay

Figure 4A:
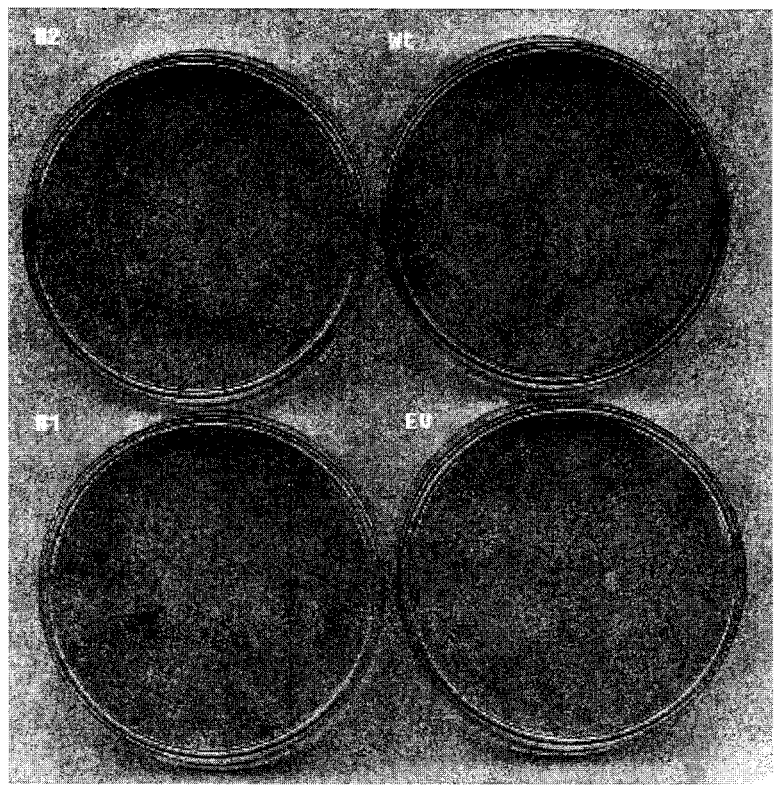
FIG. 4a shows results of an anchorage dependent colony formation assay. It is indicated that CSNK2A1P is an oncogene that is very similar to CSNK2A1.
Figure 4A:
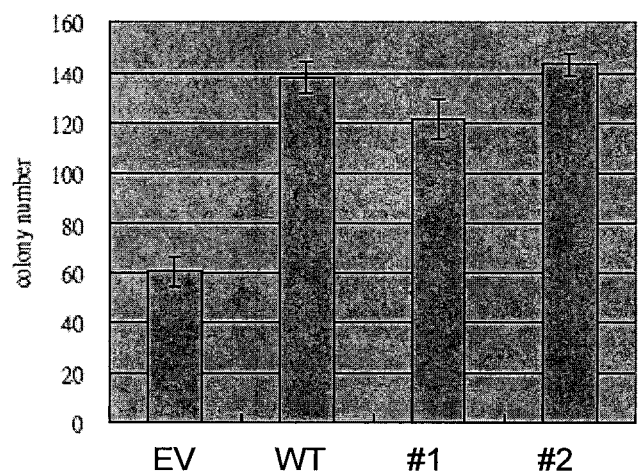

In the colony formation assay, transfection of CSNK2A1P genes in NIH3T3 cells resulted in enhanced anchorage-dependent growth, compared to the empty vector control. The colony numbers of NIH3T3-CSNK2A1 (shown as "wt") and NIH3T3-CSNK2A1P cells (both #1 and #2) were dramatically higher than that of the NIH3T3-EV cells (empty vector) (FIG. 4a). These results demonstrated that the CSNK2A1P genes code for functional protein that has transforming activity, indicating that CSNK2A1P is an oncogene that is very similar to CSNK2A1. When comparing the two alleles, the 398T allele was more transforming than the 398C allele.

Figure 4B:
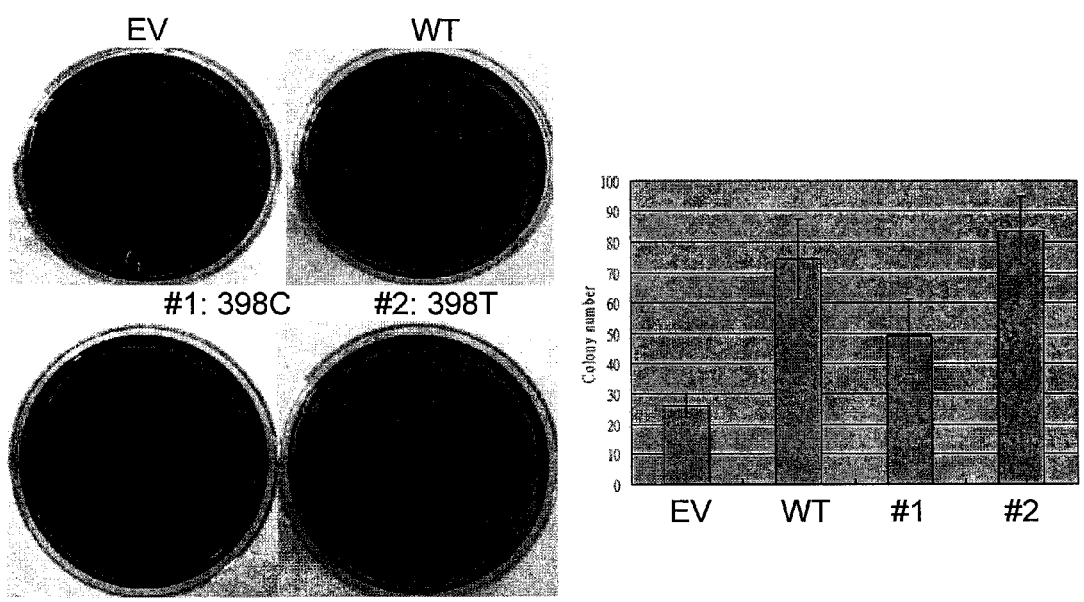
FIG. 4b shows results of an anchorage independent soft agar colony formation assay. In both colony formation assays, the 398T allele was more transforming than the 398C allele.

Transfection of the CSNK2A1P gene into NIH3T3 cells also resulted in enhanced anchorage-independent growth in soft agar colony formation assay. Both the NIH3T3-CSNK2A1 and NIH3T3-CSNK2A1P cells produced more colonies than NIH3T3-EV cells did in the soft agar colony formation assay (FIG. 4b). Compared to the NIH3T3-EV cells, NIH3T3-CSNK2A1 and NIH3T3-CSNK2A1P cells produced larger and more spread-out colony shapes. When comparing the two alleles of the CSNK2A1P genes, the 398T allele formed more colonies than the 398C allele did, again indicating that the 398T allele is more transforming than the 398C allele.

In both colony formation assays (anchorage-dependent and anchorage-independent), the 398T allele was more transforming than the 398C allele.

Example 5

CSNK2A1P promotes PML Degradation

Figure 5A:
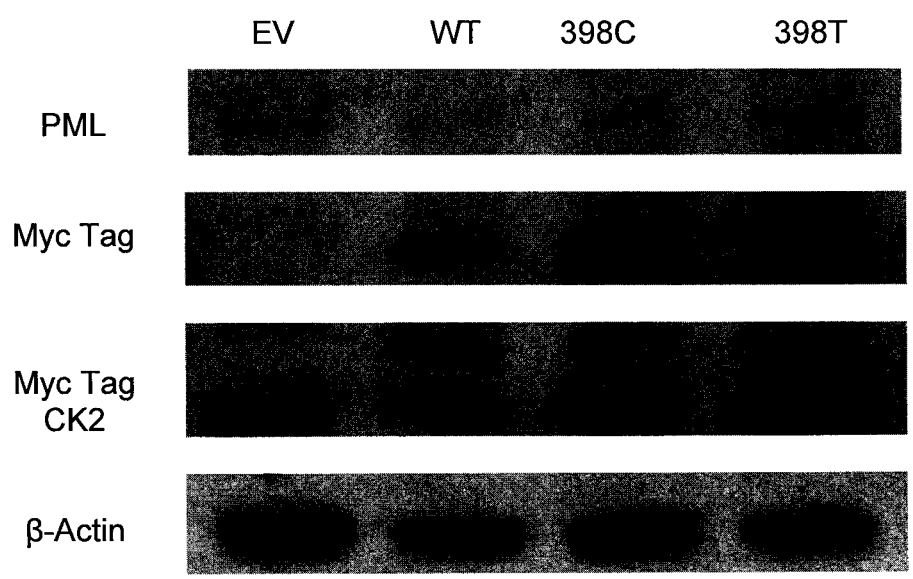
FIG. 5a is Western blot analysis showing degradation of PML in NIH3T3 stably transfected with the CSNK2A1P genes.

The possible effect of the CSNK2A1P genes on the PML and AKT kinases was studied. A recent study indicates that CK2 promotes the degradation of the PML tumor suppressor in human lung cancer cell lines. NIH3T3 cells and non-small-cell lung cancer (NSCLC) cell line H1650 were stably transfected with the CSNK2A1P genes. Western blot analysis revealed reduced PML protein levels in the cells transfected with the CSNK2A1P genes (FIG. 5a for NIH3T3 cells and FIG. 5b for H1650 cells).

Figure 5B:
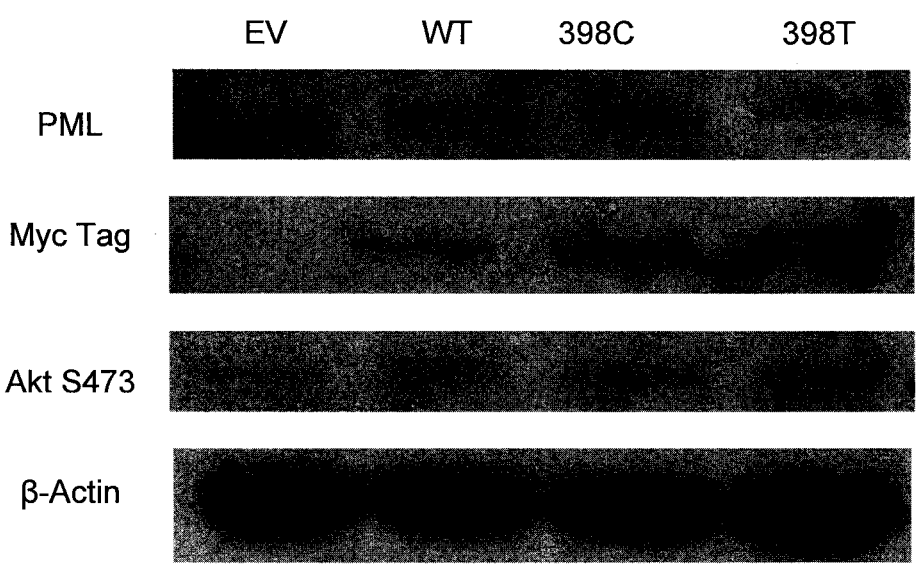
FIG. 5b is the same analysis performed in non-small-cell lung cancer (NSCLC) cell line H1650.

CK2 phosphorylated and upregulated AKT (FIG. 5b). The CSNK2A1P genes appeared to have similar functions of CSNK2A1 gene. The selective amplification of the 398T allele of the CK2α intronless gene appears to contribute, at least in part, to the pathogenesis of human lung cancer. It is noted that AKT is a kinase while PML is promyelocytic leukemia protein, a cell cycle regulator with a role in numerous cellular processes including apoptosis, viral infection, senescence and DNA repair.

Example 6 siRNA Knockdown of CSNK2A1P

Figure 6A:
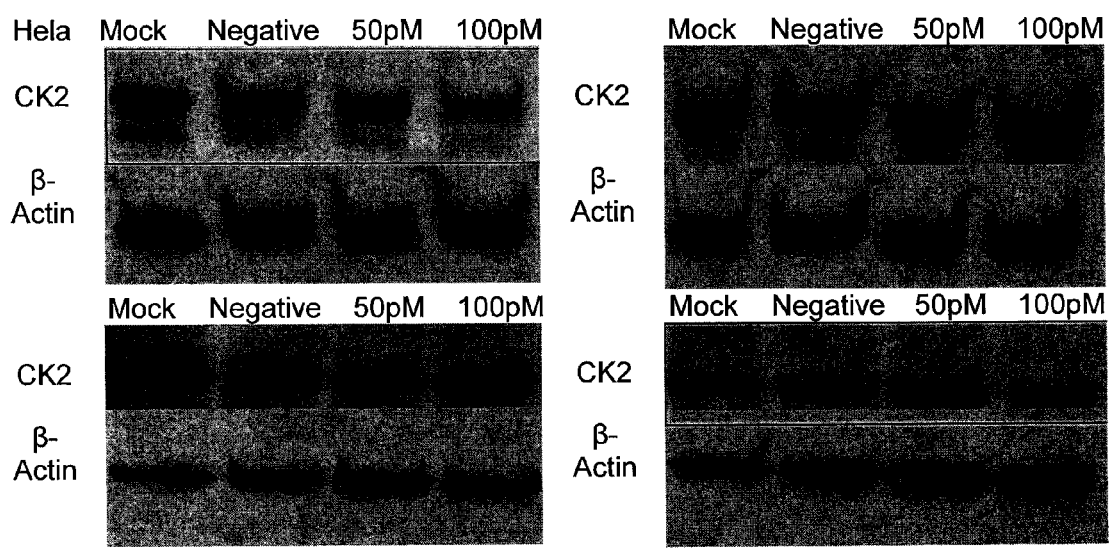
FIG. 6a shows decreased expression of CK2α protein in HCT116 and A549 upon knockdown of the CSNK2A1P genes using CSNK2A/P-specific siRNA.

CSNK2A1P-specific siRNA was transfected into several cell lines for knock down of the protein expression of CK2. The expression of total CK2α protein was measured by Western blot analysis using β-actin as an internal control (FIG. 6a). In the Hela and H460 cell lines, CK2α protein levels decreased after transfection with the CSNK2A1P-specific siRNA (upper left and lower right panels of FIG. 6a).

Figure 6B:
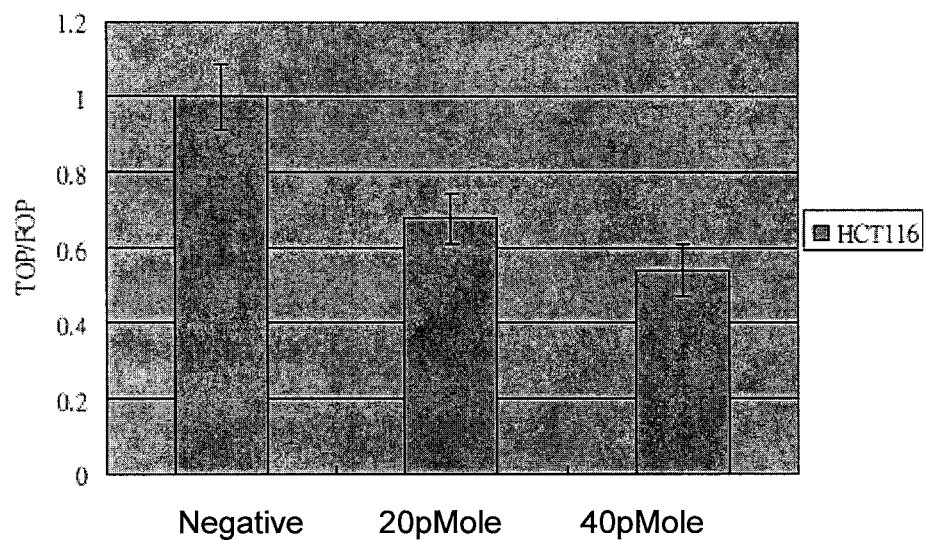
FIG. 6b shows the measurements of TOPflash luciferase activity in the HCT116 (upper panel) and A549 (lower panel) upon knockdown of the CSNK2A1P genes using CSNK2A1P-specific siRNA. The data show that siRNA to CSNK2A1P inhibits Wnt signaling in both HCT116 and A549 cell lines.
Figure 6B:
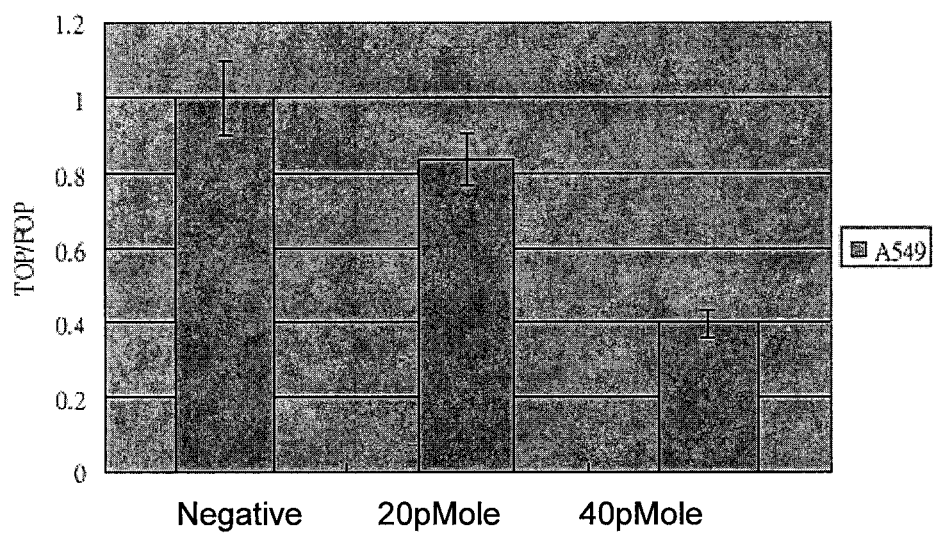

Dual luciferase assay was performed to examine down-regulation of the Wnt canonical pathway by CSNK2A1P-specific siRNA. The HCT116 and A549 cell lines were transfected with the CSNK2A1P-specific siRNA and the control TOP/FOP luciferase reporter plasmids. The transfection resulted in a concentration-dependent decrease in the TOP-flash luciferase activity with no change in the mutated control (FOPflash) at 20 pM and 40 pM in both cell lines (See FIG. 6b).

Example 7

Non-small Cell Lung Cancer (NSCLC) Patient Survival Data

Figure 7A:
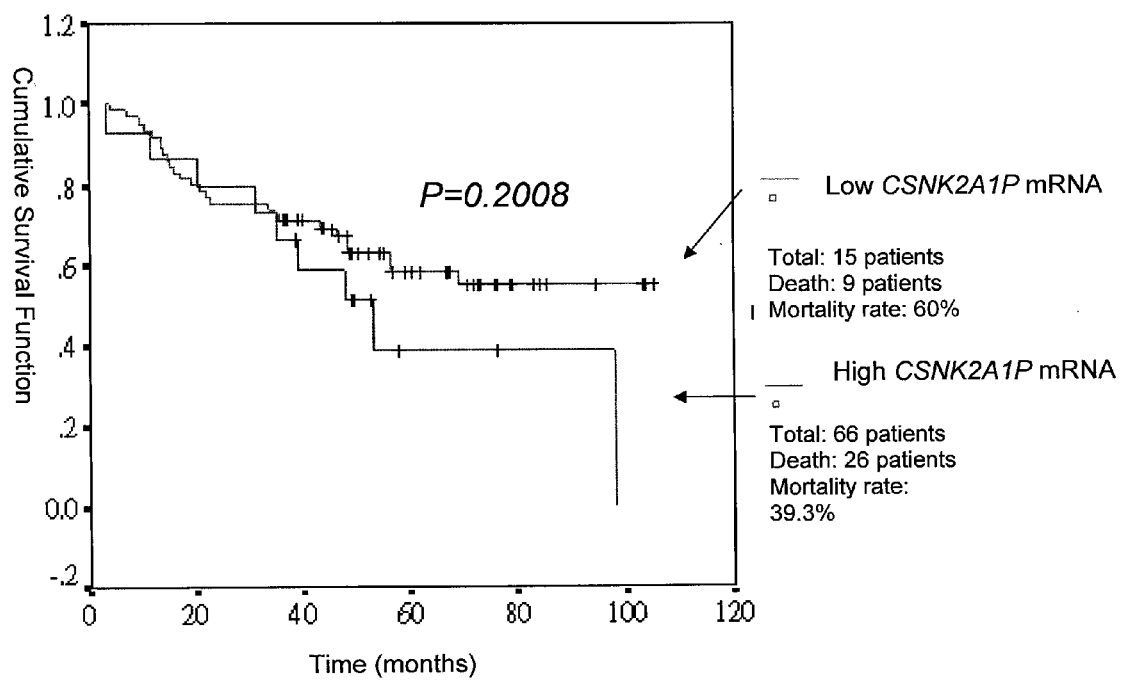
FIGS. 7a-7d show Kaplan-Meier survival data for lung cancer patients. In particular, in FIG. 7a, NSCLC patients having high CSNK2A1P mRNA levels at various stages were compared with NSCLC patients having low CSNK2A1P mRNA levels at various stages for their overall survival for a period of 120 months.
Figure 7B:
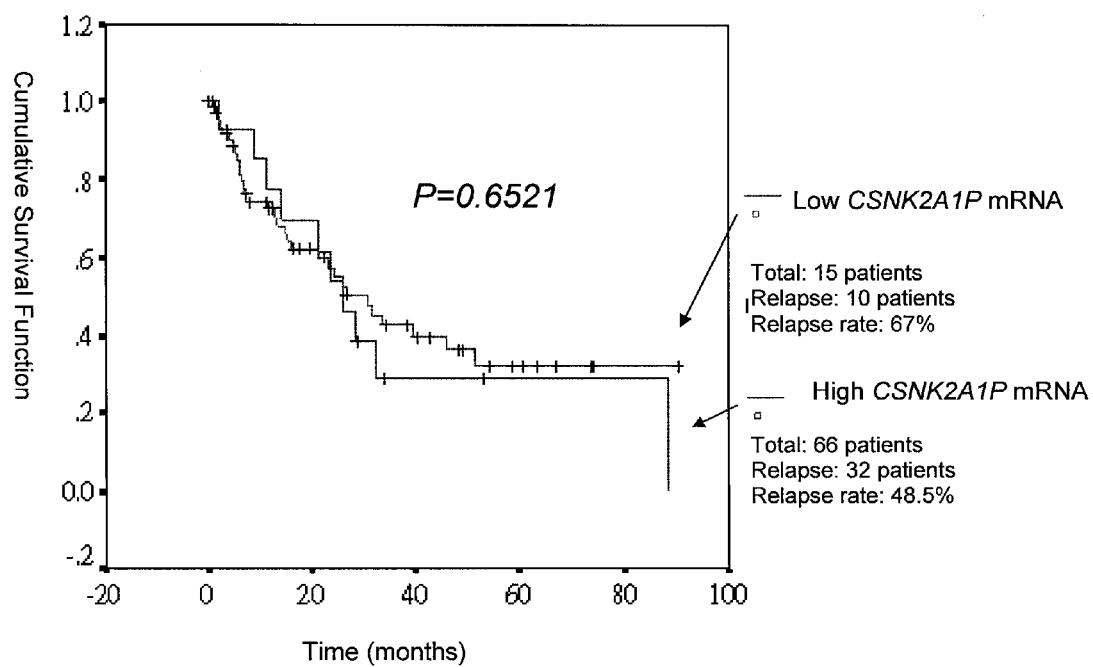
Figure 7C:
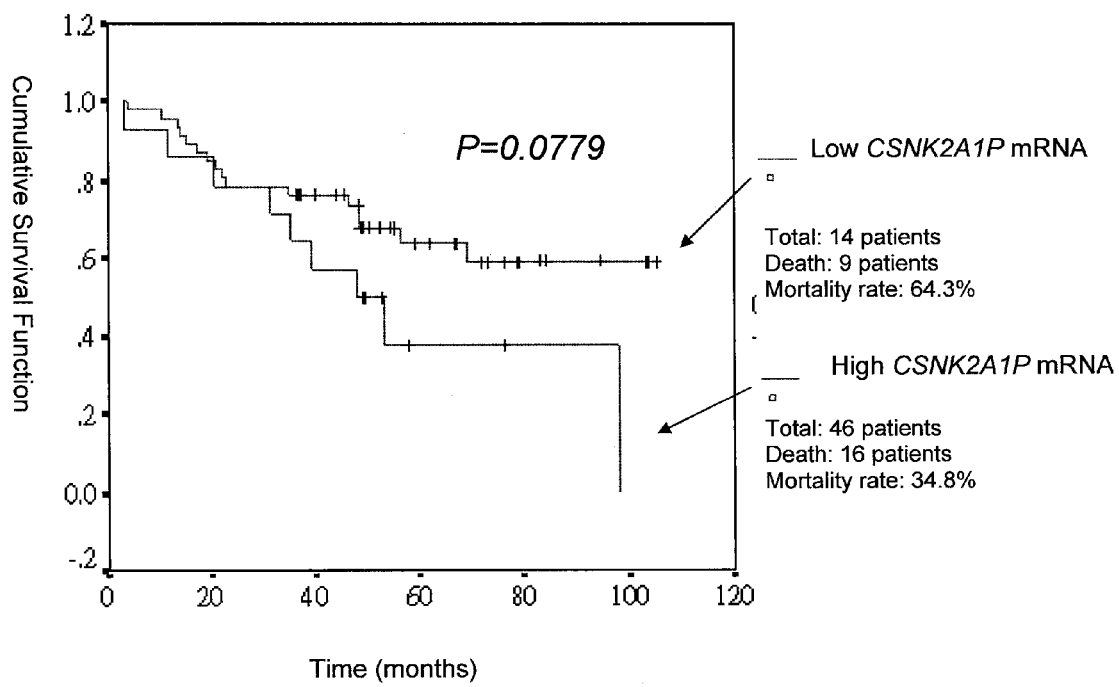
Figure 7D:
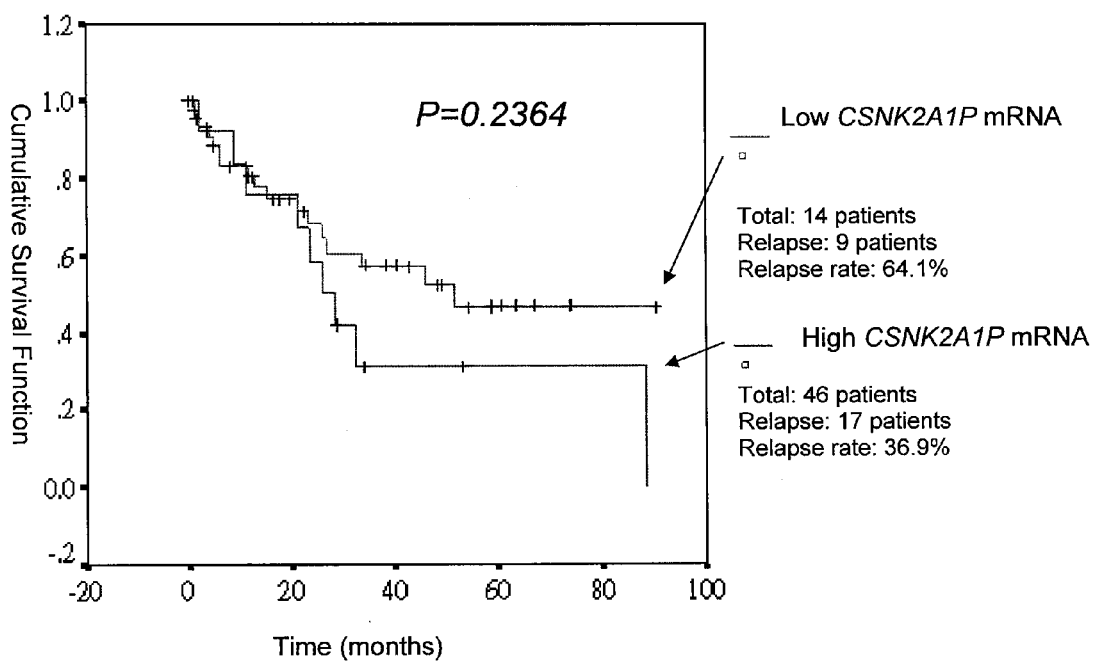

CSNK2A1P mRNA expression was measured in 81 different NSCLC patients, all at various stages of disease. The profile of the NSCLC patients was as follows:
Total: 81 patients
  Stage I: 47 patients (58%)
  Stage II: 12 patients (14.8%)
  Stage IIIA: 7 patients (8.6%)
  Stage IIIB: 7 patients (8.6%)
  Stage IV: 8 patients (9.8%)
Median follow up: 48.65 months
Median time to relapse: 21.75 months
High CSNK2A1P mRNA expression (≥24 folds of normal control): 66 patients (81%)
Low CSNK2A1P mRNA expression (<24 folds of normal control): 15 patients (19%)
Normal control: normal lung total RNA
Internal control: 18s RNA High CSNK2A1P mRNA expression was observed in 66, or 81% of the patient population. Low CSNK2A1P mRNA expression was observed in 15, or 19% of the patient population. Overall survival (FIG. 7a) and overall disease-free survival (FIG. 7b) were measured in all patients as a function of time using a Kaplan-Meier curve. The results indicated that the patient population with high CSNK2A1P mRNA expression had a lower overall mortality rate than the patient population with low CSNK2A1P mRNA expression. Overall survival (FIG. 7c) and overall disease-free survival (FIG. 7d) were measured in patients in Stages I and II. The results shown in FIGS. 7a and 7b were especially apparent in patients in Stages I and II of NSCLC disease progression, shown in FIG. 5 7c and 7d. These results indicated that CSNK2A1P mRNA expression plays a role in NSCLC.

Example 8

Abstract

Protein kinase CK2 is frequently up-regulated in human cancers, although the mechanism of CK2 activation in cancer remains unknown. In this study, we investigated the role of the CK2α intronless gene (CSNK2A1P, a presumed CK2α pseudogene) in the pathogenesis of human cancers. We found evidence of amplification and over-expression of the CSNK2A1P gene in non-small cell lung cancer and leukemia cell lines and 25% of the lung cancer tissues studied. The mRNA expression levels correlated with the copy numbers of the CSNK2A1P gene. We also identified a novel polymorphic variant (398T/C, I133T) of the CSNK2A1P gene and showed that the 398T allele is selectively amplified over the 398C allele in 101 non-small cell lung cancer tissue samples compared to those in 48 normal controls (p=0.013<0.05). We show for the first time CSNK2A1P protein expression in transfected human embryonic kidney 293T and mouse embryonic fibroblast NIH-3T3 cell lines. Both alleles are transforming in these cell lines, and the 398T allele appears to be more transforming than the 398C allele. Moreover, the 398T allele degrades PML tumor suppressor protein more efficiently than the 398C allele and shows a relatively stronger binding to PML. Knockdown of the CSNK2A1P gene expression with specific siRNA increased the PML protein level in lung cancer cells. We report, for the first time, that the CSNK2A1P gene is a functional proto-oncogene in human cancers and its functional polymorphism appears to degrade PML differentially in cancer cells. These results are consistent with an important role for the 398T allele of the CSNK2A1P in human lung cancer susceptibility.

Introduction

Lung cancer is the leading cause of death from cancer in the United States [1]. Some of the somatic events involved in lung cancer have been well characterized, but some of them remain unknown [2,3]. Protein kinase CK2 (formerly known as casein kinase II) is a serine/threonine protein kinase that phosphorylates more than 300 proteins [4]. It degrades tumor suppressor proteins such as PML [5] and promotes the activity and stability of oncogenic proteins such as AKT [6]. For instance, CK2 promotes PML degradation and CK2 kinase activity is inversely correlated with PML protein levels in human lung cancer [5]. Recently, multiple myeloma cell survival was shown to rely on the high activity of protein kinase CK2 [7]. CK2 also affects several cell signaling pathways, including PI3K, NFkB, and Wnt pathways [8].

The level of CK2α expression is tightly regulated in normal cells [9], and increased CK2α level and activity has consistently been observed in a variety of human cancers [10]. For instance, the high-level and/or nuclear localization of CK2α is a marker of poor prognosis for patients with acute myeloid leukemia, prostate cancer, and squamous cell lung cancer [10]. CK2α is the catalytic subunit of protein kinase CK2 and CK2α has been reported to be coded by the CSNK2A1 gene on chromosome 20p13 [11]. The CSNK2A1 gene can serve as an oncogene and its dysregulated expression can induce mammary tumors and lymphomas in transgenic mice [12, 13]. Although the activity of the CSNK2A1 gene has been shown to be elevated in human cancers, no solid genetic or epigenetic evidence is available regarding the cause of the high-activity of CK2α in cancer cells [10]. The CK2α intronless gene (also known as CK2α "pseudogene"), CSNK2A1P, is located on chromosome 11p15.3 and its sequence is highly homologous (99% identity) to the CSNK2A1 cDNA sequence [14]. Although the CSNK2A1P gene is reportedly expressed in a megakaryocytic cell line [15], its role in cancer cell development remains unknown. We therefore investigated the amplification and expression of the CSNK2A1P gene in lung cancer and leukemia cell lines and lung cancer tissues.

Results

Figure 8:
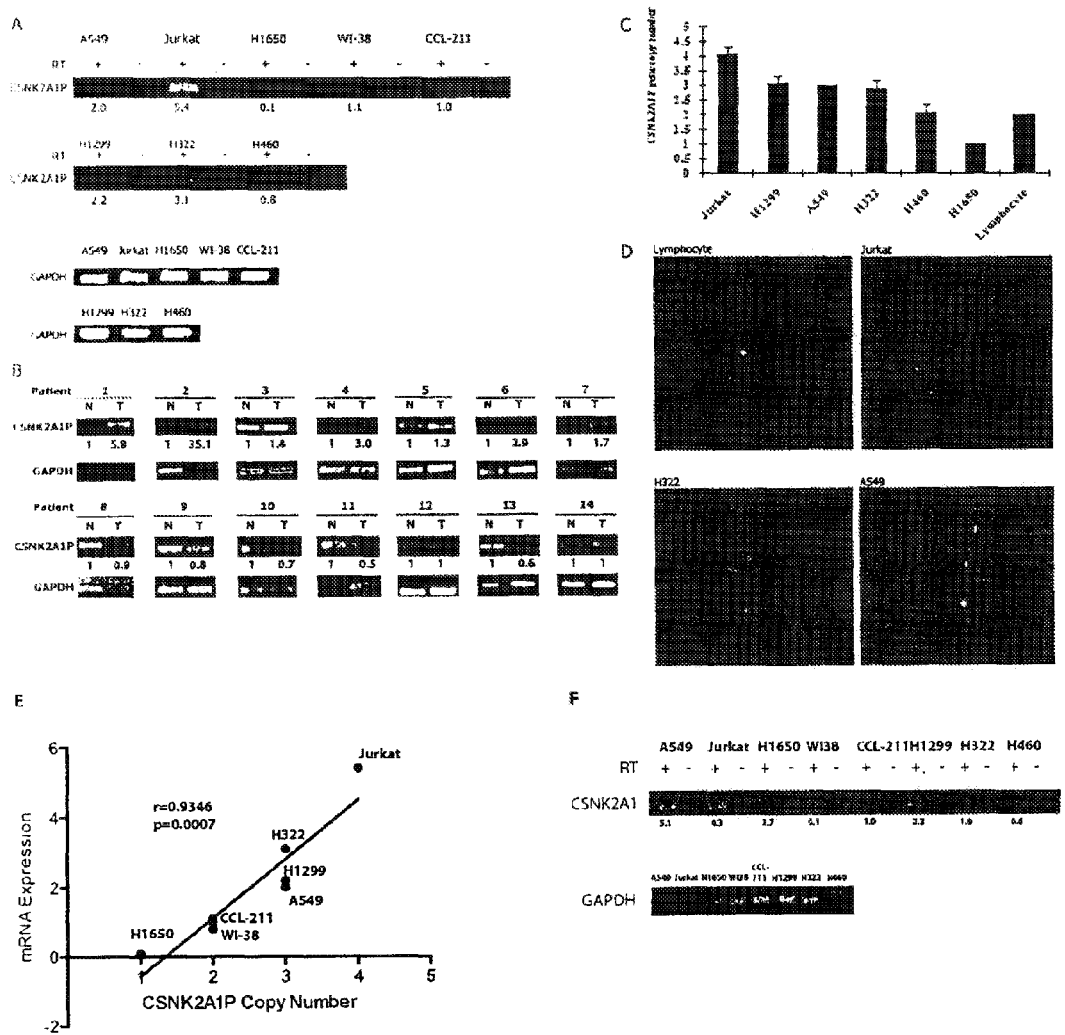
FIG. 8. CSNK2A1P gene overexpression amplification in human cancer cell lines and primary tumors. (A) Semi-quantitative RT-PCR using CSNK2A1P-specific primers shows the CSNK2A1P mRNA expression level is consistent with the copy numbers detected by FISH (3 for H1299, 4 for Jurkat, 3 for H322 and A549, 2 for WI-38 and CCL-211). (B) Semi-quantitative RT-PCR using CSNK2A1P-specific primers shows the CSNK2A1P mRNA is overexpressed in seven (patient 1 to 7) out of 29 (~25%) lung tumors as compared to matched normal adjacent tissue. Patient 8 to 14 represents samples without overexpressed CSNK2A1P mRNA. Other 14 samples with similar results are not shown. (C) The CSNK2A1P gene is amplified in the human T cell leukemia cell line Jurkat, and in lung cancer cell lines H1299, A549, and H322. (D) Representative pictures of FISH study results in metaphases of normal lymphocyte, Jurkat, H322 and A549 cell lines. The CSNK2A1P gene was labeled with Cy3 (in red). Chromosome 11 centimeter probe was labeled with FITC (in green). (E) Correlation of the copy number and mRNA expression the CSNK2A1P gene was calculated using pearson correlation. (F) Semi-quantitative RT-PCR using CSNK2A1-specific primers shows the CSNK2A1 mRNA expression level in normal and cancer cell lines mentioned above. All semi-quantitative RT-PCR experiments were repeated three times with similar results.

Over-Expression and Amplification of the CSNK2A1P Gene in Cancer Cells and Lung Cancer Tissues. We focused on the CSNK2A1P gene because we initially found it was minimally expressed in normal cells, but was predominantly expressed in several types of human cancer cell lines and tumor tissues, including the human T cell leukemia cell line Jurkat, which is known for its high CK2 activity. By semi-quantitative RT-PCR, we showed that the CSNK2A1P gene is also over-expressed in three NSCLC lines: H1299, H322, and A549, but minimally expressed in normal cells and two lung cancer cell lines H1650 and H460 (FIG. 8A). Furthermore, CSNK2A1P mRNA was overexpressed in lung tumor tissue from seven out of 29 (~25%) tumor samples as compared to matched control tissues (FIG. 8B). Moreover, FISH analysis on the same human cancer cell lines provided solid evidence of the amplification of the CSNK2A1P gene located on chromosome 11p15.3 (FIG. 8D). For example, four copies of the CSNK2A1P gene were found in the human T cell leukemia cell line Jurkat, and three copies in the lung cancer cell lines H1299, A549, and H322. In contrast, normal lymphocytes and H460 cell line had diploid copies of the CSNK2A1P gene (FIGS. 8C and D) Importantly, mRNA expression levels correlated with copy numbers of the CSNK2A1P gene in these human cancer cell lines (n=8; pearson's γ=0.9346; p=0.0007) (FIG. 8 E). We further performed semi-quantitative RT-PCR to evaluate the mRNA expression of the CSNK2A1 gene with specific primers. Overexpression of the CSNK2A1 gene was also noted in above cancer cell lines (FIG. 8F), suggesting that in addition to the CSNK2A1 gene, the CSNK2A1P gene also plays important roles in the pathogenesis of lung cancer. Alignment of the primers used for semi-quantitative RT-PCR of the CSNK2A1 and CSNK2A1P genes were shown in supplementary data (FIG. S1).

Allele-Specific Amplification of the CSNK2A1P Gene in Lung Cancer.

To determine whether there are any mutations of CSNK2A1P in human lung cancers, we sequenced the open reading frame of the CSNK2A1P gene. Although we did not find any mutations, we discovered a novel polymorphism within the kinase domain (398T/C, which leads to amino acid change I133T, FIG. 2A) in 18 cancer cell lines (Table 1) and 101 primary lung cancer tissue samples (Table 2). The specific amino acid change is predicted to affect the protein function when the sorting intolerant from tolerant (SIFT) method is used [16]. Interestingly, this polymorphism appeared to be evenly distributed in normal tissue, but in tumors, was significantly more frequent at the 398T allele (FIG. 9C) (Chi-Square test, p<0.05). Furthermore, of the 56 heterozygous lung cancer tissues examined with respect to this polymorphism (FIG. 9D), 20 (35.7%) samples showed amplification in this region, and in 18 (90%) of those 20 samples, the 398T allele was selectively amplified (FIG. 9E). This selective amplification suggests that the 398T allele might provide a growth advantage over the 398C allele. To further validate the results from DNA sequencing, we investigated the allele-specific amplification of the 398T allele of CSNK2A1P (encoding the Ile133 variant) in human tumors using a quantitative single nucleotide polymorphism (SNP) analysis, i.e., TaqMan-based allelic discrimination assay. The allelic discrimination data is consistent with the sequencing data (FIG. 9B). Of the 101 lung tumor samples typed, 56 were heterozygous with respect to the 398C→T polymorphism, and we analyzed these 56 samples for allele-specific amplification of the 398C→T polymorphism of CSNK2A1P by TaqMan analysis (FIG. 9B). Twenty samples showed allelic imbalance between the two alleles, 2 samples showed gain of the 398C allele (encoding Thr133) and 18 samples showed gain of the 398T allele (encoding Ile133). These results show statistically significant allele-specific amplification of the 398T allele (P<0.05, Chi-Square test), providing additional evidence for the role of this allele in human lung cancer. These results prompted us to probe more deeply into the role of the variant CSNK2A1P forms in tumor development.

Differential Transforming Activity of the Two CSNK2A1P Alleles.

To test the functional significance of the 398T→C polymorphism in the CSNK2A1P gene, we cloned the CSNK2A1 and CSNK2A1P genes into pcDNA 3.1/myc-His vector and carried out a series of cell growth assays using NIH3T3 cells. In this study, these vectors were transiently transfected into 293T and NIH3T3 cells and western analysis was used to confirm the protein expression of both alleles of the CSNK2A1P gene (FIG. 10A). The results show, for the first time, that the expression of CSNK2A1P can produce its proteins.

In the colony formation assay, transfection of CSNK2A1P genes in NIH3T3 (NIH3T3-CSNK2A1P) cells results in enhanced anchorage-dependent growth, compared to the empty vector control (NIH3T3-EV). In addition, we generated NIH3T3 cells with CSNK2A1 (NIH3T3-CSNK2A1) as a positive control. The colony numbers of NIH3T3-CSNK2A1 and NIH3T3-CSNK2A1P cells were dramatically higher than those of the NIH3T3-EV cells (FIG. 10B). Transfection of the CSNK2A1P gene in NIH3T3 cells also resulted in enhanced anchorage-independent growth. When soft agar colony formation assay results were compared, we found that stable transfection of CSNK2A1P genes in NIH3T3 cells resulted in enhanced anchorage-independent growth (FIG. 10C). Both the NIH3T3-CSNK2A1 and NIH3T3-CSNK2A1P cells produced more colonies than the NIH3T3-EV cells did. Compared to the NIH3T3-EV cells, NIH3T3-CSNK2A1 and NIH3T3-CSNK2A1P cells produced colonies that were mostly bigger and had spread-out shapes. When the two alleles of the CSNK2A1P genes were compared, we found that the 398T allele formed more colonies than the 398C allele did. A kinase assay of the expressed proteins was also performed (FIG. 10D). The 398T gene product has a higher kinase activity than the 398C gene product does. The results from the kinase assay are consistent with the colony formation and soft agar data.

Functional Polymorphism of the CSNK2A1P Genes on the Degradation of PML Tumor Suppressor Protein.

To determine the potential mechanism by which the 398T allele is preferentially amplified in lung cancer samples, we studied the effects of the two alleles of the CSNK2A1P gene on tumor suppressor PML protein. The CSNK2A1P genes were stably transfected into NIH3T3 and NSCLC H1650 cell lines. Western blot analysis showed a reduced PML protein level in the cells transfected with the CSNK2A1P genes. The CSNK2A1P 398T allele, similar to wild-type CSNK2A1, decreased PML protein levels more than the 398C allele did (FIG. 11A). Second, we determined whether the half-life of PML is differentially regulated by the two alleles. These two cell lines transfected with the CSNK2A1P gene were treated with cycloheximide for 0, 2, and 6 hours, and the endogenous PML protein levels were examined The 398T allele decreased the half-life of PML more effectively than the 398C allele did (FIG. 4B). Third, we used co-immunoprecipitation to show the direct and preferential binding between the 398T protein and PML protein (FIG. 11C).

To further address the question of whether the CSNK2A1P mRNA is fully translated and degrades PML in cancer cells, we knocked down the CSNK2A1P gene in H1299 lung cancer cell lines with siRNA specific to the CSNK2A1P gene. We chose the H1299 lung cancer cell line because our study (FIGS. 1A and C) showed that the CSNK2A1P gene is amplified and overexpressed in this cell line. The CSNK2A1P gene specific siRNA caused a greater than 70% decrease in the expression of the CSNK2A1P gene and no decrease in the expression of the CSNK2A1 and CSNK2B genes (FIG. 4D). In accordance with decreased expression of the CSNK2A1P gene, the total CK2α protein decreased and the PML protein increased in the cells treated with CSNK2A1P siRNAs compared to negative siRNA transfected controls (FIG. 4E).

Discussion

In this study, we have provided, to our knowledge, the first evidence to show that the CSNK2A1P gene is a functional proto-oncogene in human cancers. To support our hypothesis that CSNK2A1P gene is a functional proto-oncogene, rather than a "pseudogene", we have done extensive DNA, mRNA, protein and siRNA analysis. The results of this analysis provide the first evidence that the mRNA expression level correlates with the copy number of the CSNK2A1P gene in several human cancer cell lines. Furthermore, siRNA knock down of the CSNK2A1P gene decreased total CK2α protein level in cancer cells, indicating that the CSNK2A1P gene is fully translated in cancer cells. Thus, the amplification of the CSNK2A1P gene may play an oncogenic role in these human cancer cell lines. On the basis of our results, we propose that two functional genes may exist in the human CK2α family, CSNK2A1, which locates on the chromosome 20p13, and CSNK2A1P, which locates on the chromosome 11p15.3.

We also found a novel polymorphism within the kinase domain (398T/C, which leads to amino acid change I133T, FIG. 9*a*) in 101 primary tumors. This polymorphism appears to be evenly distributed in normal tissue, but in tumors, is significantly more frequent in the 398T allele (Table 2, FIG. 9). The 398T allele was selectively amplified in eighteen of the 101 lung cancer tissues, suggesting it might provide a growth advantage over the 398C allele. The 398C allele amplification was only found in two of the 101 lung cancer tissues, suggesting that it might be a random event. These intriguing genetic results prompted us to probe more deeply into the role of the variant CSNK2A1P forms in tumor development. Doing so yielded two important findings, first, that the 398T allele is more transforming than the 398C allele, and second, that the 398T allele degrades tumor suppressor PML protein more efficiently than the 398C allele. For instance, the 398T allele showed significantly higher transforming activity in both colony formation and soft agar assays than the 398C allele (FIGS. 10B and C). The data of the kinase assay showed that the 398T gene product has higher kinase activity than the 398C gene product (FIG. 10D), suggesting that the 398T allele is a more transforming allele than the 398C allele. In addition, these data also suggest that the transforming ability of the 398T allele of the CSNK2A1P pseudogene is similar to that of the normal CSNK2A1 gene product, so the more active allele of the pseudogene appears to have activity comparable to the regular CSNK2A1 gene. To date, there is no genetic or epigenetic evidence on the activation of the CSNK2A1 gene in human cancer. Thus our study provides the first evidence that the CSNK2A1P 398T allele, which is similar to the CSNK2A1 gene, is amplified in human lung cancer tissues.

The PML gene was originally identified at the breakpoint of t(15;17) translocation in acute promyelocytic leukemia [17] and was proved to be a tumor suppressor gene [18]. Loss of PML has been correlated with poor clinical outcome in a variety of human cancers, including lung cancer, supporting its tumor suppressor function [5, 19]. PML promotes the dephosphorylation of pRb and regulates cell fate in the developing neocortex [20]. CK2 regulates ubiquitin-mediated degradation of PML in human lung cancer cell lines [5, 21]. This may be one the potential mechanisms by which the 398T allele is preferentially amplified in lung cancer samples. This genetic polymorphism is probably a useful marker to detect the amplification of the CK2 intronless gene, because monoallelic amplification is believed to be responsible for gene amplification in cancer [22]. This allele-specific amplification also implies that cancer cells may be addicted to the oncogenic CK2α [23]. In short, the amplification of the 398T allele of the CSNK2A1P gene may contribute, at least in part, to the pathogenesis of lung cancer.

The CSNK2A1P gene is a processed pseudogene located on the chromosome 11p15.3 and is supposed to be formed by retrotransposition, and characterized by the absence of introns, the presence of flanking directs repeats, and the 3' polyadenylation tail [15]. However, it has a strong promoter upstream from the initiation codon (14, 15). The expression of the CSNK2A1P gene is potentially more tightly regulated than the CSNK2A1 is. For instance, the promoter region of the CSNK2A1P gene contains two TATA boxes and a CAAT box, while the upstream sequence of CSNK2A1 displays housekeeping gene characteristics, e.g., high GC content, the presence of several GC boxes and the lack TATA box (14, 15). Moreover, several important transcription factor-binding sites (e.g, CEBP-, GATA-, and SMAD-binding sites) were predicted within the 5' region (1 Kb) from the CSNK2A1P starting codon, suggesting that the CSNK2A1P gene may potentially be induced or repressed by several master regulators of developmental pathways. The amplification of the CSNK2A1P gene could result in the overexpression of CSNK2A1P protein in cancer cells. It may also be possible that the CSNK2A1 gene is somehow indirectly regulated by the expression of the CSNK2A1P gene. Future studies are needed to uncover the mechanism through which the CSNK2A1P and the CSNK2A1 genes are regulated. Until now, around 10,000 processed pseudogenes [24] have been characterized in the human genome, and some of these genes have been reported to be expressed in cancer cells. For instance, the oncogenic CRIPTO3 pseudogene is expressed in colon, breast and lung cancers[25], the human homologue of vaccinia virus H1 phosphatase gene clone 5 (hVH-5) pseudogene is expressed in breast cancer cell lines[26], and the rac1 pseudogene is expressed in brain tumors [27]. Taken together with our results, this suggests a potential oncogenic role of the presumed pseudogenes in some human cancers.

This study had some limitations. We demonstrated the correlation between CSNK2A1P gene and PML protein stability in only two lung cancer cell lines in vitro. Specimens from only 101 lung cancer patients were analyzed, 56 of which were heterozygous with respect to this polymorphism and could be used for the analysis. In future studies, it will be important to include additional cancer cell lines and more cancer tissues.

Our results provide genetic evidences for activation of the intronless CK2α gene in human cancer. Although CK2 was previously known to be a key player in cancer, its mechanism of activation in cancer was not known [10,28]. Because of this lack of knowledge about the mechanism of CK2 activation and its constitutive activity, CK2 has been mostly neglected as a key target for anti-cancer drugs. Since significant progress has been made on the structural bases of CK2 inhibition, it is now possible to develop potent and selective cell-permeable CK2 inhibitors [29, 30]. Understanding the difference in sequences of the CSNK2A1P gene polymorphisms may allow us to design specific diagnostic tests for human cancer Importantly, our results support the notion that protein kinase CK2α is an appealing target for cancer therapeutics such as small-molecule inhibitors [10, 31].

Materials and Methods

Cell lines. The human cancer (Jakurt, H1299, A549, A427, H441, H1703, H322, H460, HCT116, H1975, H322, H358, H838, H28, H2052, Hela and H1650) and normal lung (WI-38 and CCL-211) cell lines were obtained from American Type Culture Collections (Manassas, Va.). H290 and MS-1 cell lines were obtained from NIH (Frederick, Md.). Cells were grown in complete growth medium (Dulbecco's modified Eagle's medium for HeLa, A549 and CCL-211; Eagle's Minimum Essential Medium for WI-38; Roswell Park Memorial Institute's medium for H1299, A549, A427, H441, H1703, H322, H460, HCT116, H1975, H322, H358, H838, H28, H2052 and H1650) supplemented with 10% fetal bovine serum, 10 units/ml penicillin and 10 µg/ml streptomycin at 37° C. and 5% CO2.

Tissue samples. Fresh tumor tissues and adjacent normal tissues were obtained from patients with non-small cell lung cancer (NSLC) who were undergoing surgical resection of the primary tumor. The study was approved by the University of California, San Francisco, institutional review board (CHR#H8714-11647-14). We obtained written informed consents from all participants involved in our study. Tissue samples were kept at −180° C. liquid nitrogen freezers before use, and final pathologic diagnosis was confirmed by a pathologist at the University of California, San Francisco (UCSF), USA. Normal adult genomic DNA form peripheral blood was purchased from BioChain (Hayward, Calif.).

Fluorescence-in situ hybridization. The fluorescence-in situ hybridization (FISH) probe for CSNK2A1P(RP11-567I13, chromosome 11p15.3) was purchased from BACPAC Resources (Oakland, Calif.). The chromosome 11 centromere was labeled by Vysis CEP 11 SpectrumGreen™ probe (Abbott Molecular, Abbott Park, Ill.). Metaphase slides were prepared using standard protocols of the UCSF Molecular Pathology Core facility. All hybridizations were done by the UCSF Molecular Pathology Core facility. The CSNK2A1P BAC probe was labeled with Cy3 red by nick translation. Probe mixture was prepared according to the standard protocol.

DNA and cDNA sequencing analysis. Genomic DNA or total RNA was isolated from cell lines and tissue samples using the DNeasy Blood & Tissue Kit or the RNeasy Mini Kit (Qiagen Valencia, Calif.), respectively. The CSNK2A1P gene was PCR amplified using its gene-specific primers. The forward and reverse primers used for PCR and sequencing were: 5'-AGAAAATTGCTCCCCACTCC-3' and 5'-GTGCTGC-CAGAGAATGA CAA-3' respectively. The PCR products were gel-purified using the QIAquick Gel Extraction kit (Qiagen Valencia, Calif.) and were subsequently sequenced at MCLab (South San Francisco, Calif.).

Semi-quantitative reverse transcription-PCR(RT-PCR) analysis. Total RNA from cell lines and tissues was isolated using an extraction kit, and DNA was eliminated by on-column treatment with DNase (RNeasy Mini kit; Qiagen, Valencia, Calif., USA). Semiquantitative RT-PCR was performed by using SuperScript One-step RT-PCR with Platinum Taq kit (Invitrogen, Carlsbad, Calif.) according to the manufacturer's protocol. One-step RT-PCR was performed using pairs of CSNK2A1P-specific primers (Forward: 5'-AGAAAATTGCTCC CCACTCC-3' and Reverse: 5'-GTGCTGCCAGAGA ATGACAA-3'), CSNK2A1-specific primers (Forward: 5'-TGGGGACAGAAGATTTATATGA-3' and Reverse: 5'-CTGAAGAAATCCCTGACA TCAT-3') and CSNK2B-specific primers (Forward: 5'-CAGGTCCCT-CACTACCGACA-3' and Reverse: 5'-CAGCTGGTAGGC-CATCGGAT-3'). The PCR products were verified by direct DNA sequencing. Glyceraldehyde-3-phosphatedehydrogenase (GAPDH) was used as an internal control. Amplification conditions for CSNK2A1P, CSNK2A1 and CSNK2B were as follows: 1 cycle of 45° C. for 30 min, followed by 1 cycle of 95° C. for 5 min, and 35 cycles of 95° C. for 1 min, 56° C. for 1 min, 72° C. for 1 min and 1 cycle of 72° C. for 10 min then 4° C.

Cloning of SCNK2A1P cDNAs. The full-length cDNA of CSNK2A1P gene from A549 cells was cloned using TOPO TA Cloning Kit (Invitrogen Carlsbad, Calif.), and then was subcloned into the HindIII and BamHI sites of the pcDNA3.1/myc-His vector (Invitrogen, Carlsbad, Calif.). The forward and reverse primers used for cloning were 5'-CCT- TAAAAGCTTGACCATGTCGG GACCCGTGCCAAG-3' and 5'-CCTTAAGGA TCCGACTGCTGAGCGCCAGCG-GCAG-3' respectively. The CSNK2 A1pcDNA3.1/myc-His vector was a gift from Dr. L. A. Pinna. Both myc-His tagged CSNK2A1 and CSNK2A1P genes were subsequently cloned into the SnaBI site of the pBabe-puro vector. The forward and reverse primers used for cloning were 5'-GGCTAGTTTACG-TAG ACCATG TCGGGACCCGTG CCAAG-3' and 5'-AAGGCACAGT CGACGCT GATCAGCGGGTT TAAACTCA-3' respectively. All resultant vectors were verified by direct DNA sequencing.

Retroviral production and transduction. The CSNK2A1 and CSNK2A1P retroviral vectors were then transfected into the HEK 293 Phoenix ampho packaging cells (ATCC, Manassas, Va.) by using Fu-GENE6 transfection reagent (Roche, Lewes, UK) to produce retroviral supernatants. Forty-eight hours after transfection, the supernatant was filtered through a 0.45 μm syringe filter. Retroviral infection was performed by adding filtered supernatant to mesothelioma cell lines cultured on 10 cm dishes with 50% confluent in the presence 8 ug/ml of polybrene (Sigma, St. Louis, Mo.). Six hours after infection, the culture medium was replaced with fresh medium and infected cells were allowed to recover for 48 hours. Infected cells were selected by adding 1 μg/ml puromycin (Sigma, St. Louis, Mo.) to the culture medium for 48 hours and then maintained in complete medium with 0.5 μg/ml puromycin. Empty retroviral infected stable cell lines were also produced by the above protocols.

Western blot analysis. Whole protein was extracted by M-PER Mammalian Protein Extraction Reagent from cell lines added with Phosphatase Inhibitor Cocktail Set II (Calbiochem, San Diego, Calif.) and Complete Protease Inhibitor Cocktails (Roche, Lewes, UK) according to manufactures' protocols. The proteins were separated on 4-15% gradient SDS-polyacrylamide gels and transferred to Immobilon-P membranes (Millipore, Bellerica, Mass.). The following primary antibodies were used: anti-CK2α, anti-β-actin (Sigma Chemical, St. Louis, Mo.), anti-PML (Santa Cruz, Santa Cruz, Calif.), and anti-Myc tag (Cell Signaling, Danvers, Mass.). After being incubated with appropriate secondary antibodies, the antigen-antibody complexes were detected by using an ECL blotting analysis system (Amersham Pharmacia Biotech, Piscataway, N.J.).

Colony formation assay. NIH3T3 cells stably transfected with CSNK2A1 or CSNK2A1P ($5 \times 10^2$) were plated in 10 cm culture dishes and incubated in complete medium for 14 days. The colonies were then stained with 0.1% crystal violet, and colonies greater then 50 cells were counted. Results were expressed as relative colony formation: percentage of the number of colonies relative to the empty vector transfected controls. Three independent experiments were performed.

Soft agar growth assay. For experiments using the pcDNA3.1/myc-His vectors expressing CSNK2A1 and CSNK2A1P, NIH3T3 cells were transfected with these vectors or control empty vector and then selected in 100 ug/ml of G418 for 1 week. Cells ($1 \times 10^3$) were then cultured in DMEM plus 15% FBS in 0.35% (w/v) low melting temperature agar between layers of 0.7% low melting temperature agar. After 4 weeks, colonies were stained with 3-(4,5-dimethylthiazol-2-yl)-2,5-diphenyltetrazolium bromide (Sigma Chemical Co.), and colonies containing >100 cells were scored. Colonies were photographed and counted after staining.

Protein degradation assay. The stable NIH3T3 cells retrovirally transfected with CSNK2A1 and CSNK2A1P were plated on 6 cm culture dishes. At 80% confluence, cells were exposed to 20 μg/ml cycloheximide and harvested at different time points (0, 2 and 6 hours). Total cellular proteins were extracted and were analyzed by western blot analysis using β-actin as the loading control.

Co-immunoprecipitation assay. 293T cells were transiently co-transfected with PML pcDNA4/V5-His (a gift from Dr. Zheng Pan) and CSNK2A1 or CSNK2A1P pcDNA3.1/myc-H is vectors with Lipofectamine 2000 transfection reagent (Invitrogen Carlsbad, Calif.). Twenty-four hours after transfection, cells were treated with 10 μM of MG132 (Sigma, St. Louis, Mo.) and then harvested in NP-40 lysis buffer (150 mM NaCl, 50 mM Tris [pH 8.0], 1% NP40), protease inhibitor, and phosphatase inhibitor cocktail (Roche, Lewes, UK) Immunoprecipitation was performed by the Catch and Release v2.0 Reversible Immunoprecipitation System (Millipore, Bellerica, Mass.) according to the manufacturer's protocols. Anti-Myc tag (Santa Cruz, Santa Cruz, Calif.) and anti-V5 tag (Invitrogen, Carlsbad, Calif.) antibodies were used for immunoprecipitation respectively.

Transfection of small interfering RNA. Pre-designed and validated CSNK2A1P and universal negative control small interfering RNAs (siRNA) were purchased from Invitrogen (Carlsbad, Calif.). Transfection was performed using Lipofectamine™ RNAiMAX Transfection Reagent (Invitrogen), according to the manufacturer's manual. Cells were plated in 60-mm dishes in antibiotic-free media and transfection was performed with cells at 60% confluence with a final concentration of 50 nM for each siRNA. At 72 hours after transfection, cells were analyzed for gene and protein expression.

Allele-specific amplification assays. The allele-specific amplification was measured using the ABI PRISM 7700 sequence detection system. PCR reactions for allele-specific expression (5 μl) contained 10 ng genomic DNA, 1× TaqMan universal PCR master mix, forward and reverse primers (900 nM), 200 nM VIC-labeled probe and 200 nM FAM-labeled probe. Amplification conditions were as follows: 1 cycle of 95° C. for 10 min, followed by 40 cycles of 95° C. for 15 s and 63° C. for 1 min. The data was analyzed using the Allelic Discrimination Sequence Detection Software (Applied Biosystems). The TaqMan primers and probes were custom designed using the Primer Express Oligo Design Software (Applied Biosystems). Probes were MGB probes were designed specifically for TaqMan Allelic Discrimination (Applied Biosystems). Primer sequences are 5'-CCGCCT-TGGTTTTTGAACAC-3' and 5'-GGCCTTCAGAATCT-CATACATGTAAA-3'; probe sequences are FAM-CACA-GACTATGACTC (398C allele specific) and VIC-TCACAGACTATGATTC (398T allele specific). PCR was done in triplicate for each sample and experiments were repeated at least three times. CT values were normalized to the average normal genomic CT difference in each experiment. The CT value differences between the two probes for the triplicates were then averaged.

Kinase assays. For determination of the kinase activity of the expressed CSNK2A1 and CSNK2A1P proteins, Casein Kinase 2 Assay Kit (Millipore, Bedford, Mass.) was used according to manufacture's protocol. Stable NIH3T3 cells transfected with the CSNK2A1 and CSNK2A1P genes were harvested in NP-40 lysis buffer (150 mM NaCl, 50 mM Tris [pH 8.0], 1% NP40), protease inhibitor, and phosphatase inhibitor cocktail (Roche, Lewes, UK). Immunoprecipitation was performed by the Catch and Release v2.0 Reversible Immunoprecipitation System (Millipore, Bellerica, Mass.) according to the manufacturer's protocols. Anti-Myc tag (Santa Cruz, Santa Cruz, Calif.) antibody was used for immunoprecipitation. Kinase assay was carried in a final volume of 50 μl containing 20 mM MOPS (pH 7.2), 25 mM β-glycerol phosphate, 5 mM EGTA, 1 mM sodium orthovanadate, 1 mM dithiothreitol, 15 mM Mgcl$_2$, 200 µM for CK2 substrate peptide: RRRDDDSDDD (Millipore, Bedford, Mass.), and [γ-33P]-ATP. After incubation in 30° C. for 20 minutes, assay was stopped by adding of 20 µl 4% trichloroacetic acid and transferred 25 µl to P81 phosphocellulose squares. After washing with 0.75% phosphoric acid for 6 times and with acetone for 1 time, phosphocellulose squares were dried and transferred to scintillation vials for counting.

Statistical analysis. The data are shown as mean values±standard deviation (SD). Student's t-test was used to compare results between control and experimental groups in the colony formation assay. Chi-square test was used to compare the frequency of the CSNK2A1P polymorphisms between lung cancer tissues and normal controls. Pearson correlation coefficient was used to access the correlation between mRNA expression and copy numbers of the CSNK2A1P gene in cancer cell lines. Statistical analysis was carried out using SPSS (version 10.0, Chicago, Ill.). A P value of less than 0.05 was considered statistically significant. All statistical tests were two-sided.

TABLE 1

DNA sequencing results of the 398 allele in cancer cell lines

| Cell line type and name | | 398T | 398T/C | 398C |
|---|---|---|---|---|
| Lung cancer | H1299 | | + | |
| Lung cancer | A549 | | + | |
| Lung cancer | A427 | + | | |
| Lung cancer | H322 | | | + |
| Lung cancer | H358 | | | + |
| Lung cancer | H441 | + | | |
| Lung cancer | H460 | + | | |
| Lung cancer | H838 | + | | |
| Lung cancer | H1650 | | | + |
| Lung cancer | H1703 | + | | |
| Lung cancer | H1975 | | | + |
| T cell leukemia | Jurkat | + | | |
| Colon cancer | HCT116 | | | + |
| Cervical cancer | Hela | + | | |
| Mesothelioma | MS-1 | + | | |
| Mesothelioma | H28 | + | | |
| Mesothelioma | H2052 | + | | |
| Mesothelioma | H290 | + | | |

TABLE 2

DNA sequencing results of the 398 allele in 101 lung cancer tissues samples and genomic DNA from 48 normal adults

| Sequencing results | Lung cancer samples Sample numbers (%) | Normal genomic DNA Sample numbers (%) |
|---|---|---|
| CC/T | 2 (2%) | 0 (0%) |
| TT/C or TTT/C | 18 (17.8%) | 0 (0%) |
| T | 35 (34.6%) | 12 (25%) |
| C/T or T/C | 36 (35.6%) | 24 (50%) |
| C | 10 (10%) | 12 (25%) |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of providing a prognosis for lung cancer in a human subject with lung cancer, the method comprising:
   (a) measuring the expression level of CSNK2A1P mRNA in a biological sample from the subject using a RT-PCR or quantitative PCR assay, wherein the assay comprises the use of a CSNK2A1P primer comprising the nucleotide sequence of SEQ ID NO: 7, SEQ ID NO: 8, SEQ ID NO: 9, or SEQ ID NO:10, and wherein the biological sample comprises lung tissue, and
   (b) providing a prognosis for lung cancer in the subject, wherein the prognosis for lung cancer is based on the expression level of CSNK2A1P mRNA in the sample, wherein a higher level of CSNK2A1P mRNA expression as compared to control lung tissue indicates a lower overall mortality rate, wherein a lower level of CSNK2A1P mRNA expression as compared to control lung tissue indicates a higher overall mortality rate, and wherein the CSNK2A1P mRNA encodes for a polypeptide comprising SEQ ID NO: 4.

2. The method of claim 1, wherein a lower level of CSNK2A1P is indicative of an increased risk of cancer recurrence, a reduced likelihood of long term survival, or a reduced likelihood of long term disease free survival in the subject.

3. The method of claim 1, wherein the lung cancer is Stage I, Stage II, Stage IIIA, Stage IIIB, or Stage IV lung cancer.

4. The method of claim 1, wherein the lung cancer is non-small cell lung cancer (NSCLC).

5. The method of claim 1, wherein a higher level of CSNK2A1P is indicative of a decreased risk of cancer recurrence, an increased likelihood of long term survival, or an increased likelihood of long term disease free survival in the subject.

6. A method of diagnosing lung cancer in a human subject, the method comprising:
   (a) measuring the expression level of CSNK2A1P mRNA in a biological sample from the subject using a RT-PCR or quantitative PCR assay, wherein the assay comprises the use of a CSNK2A1P primer comprising the nucleotide sequence of SEQ ID NO: 7, SEQ ID NO: 8, SEQ ID NO: 9, or SEQ ID NO:10, and wherein the biological sample comprises lung tissue, and
   (b) diagnosing lung cancer in the subject, wherein the diagnosis is based on the expression level of CSNK2A1P mRNA in the sample, wherein over-expression of CSNK2A1P mRNA as compared to control lung tissue indicates a diagnosis of lung cancer, and wherein the CSNK2A1P mRNA encodes for a polypeptide comprising SEQ ID NO: 4.

7. The method of claim 6, wherein the lung cancer is Stage I, Stage II, Stage IIIA, Stage IIIB, or Stage IV lung cancer.

8. The method of claim 6, wherein the lung cancer is non-small cell lung cancer (NSCLC).

9. The method of claim 1 wherein the method comprises the use of two CSNK2A1P primers.

10. The method of claim 9 wherein the method comprises the use of CSNK2A1P primers comprising the nucleotide sequences of SEQ ID NO: 7 and SEQ ID NO: 8.

11. The method of claim 9 wherein the method comprises the use of CSNK2A1P primers comprising the nucleotide sequences of SEQ ID NO: 9 and SEQ ID NO: 10.

12. The method of claim 6 wherein the method comprises the use of two CSNK2A1P primers.

13. The method of claim 12 wherein the method comprises the use of CSNK2A1P primers comprising the nucleotide sequences of SEQ ID NO: 7 and SEQ ID NO: 8.

14. The method of claim 12 wherein the method comprises the use of CSNK2A1P primers comprising the nucleotide sequences of SEQ ID NO: 9 and SEQ ID NO: 10.

* * * * *